US007215811B2

(12) United States Patent
Moselhi et al.

(10) Patent No.: US 7,215,811 B2
(45) Date of Patent: May 8, 2007

(54) METHOD AND APPARATUS FOR THE AUTOMATED DETECTION AND CLASSIFICATION OF DEFECTS IN SEWER PIPES

(75) Inventors: Osama Moselhi, 3 PL. Colbert, Kirkland, Que. (CA) H9H-358; Tariq Shehab-Eldeen, Montreal (CA)

(73) Assignees: Osama Moselhi, Montreal (CA); Tariq Shebab-Eldeen, Long Beach, CA (US)

( * ) Notice: Subject to any disclaimer, the term of this patent is extended or adjusted under 35 U.S.C. 154(b) by 752 days.

(21) Appl. No.: 09/990,572

(22) Filed: Nov. 23, 2001

(65) Prior Publication Data
US 2003/0023404 A1 Jan. 30, 2003

Related U.S. Application Data

(60) Provisional application No. 60/252,484, filed on Nov. 22, 2000.

(51) Int. Cl.
*G06K 9/62* (2006.01)
(52) U.S. Cl. ............... 382/156; 382/149; 382/224; 706/15
(58) Field of Classification Search ........... 382/100, 382/156, 157, 190, 191, 192, 195, 218, 224, 382/228, 276, 173, 149; 73/587, 592, 623, 73/618, 619; 348/84, 88, 125, 91, 92, 128; 707/101, 100, 200, 6, 2; 706/1, 15, 25; 376/250, 376/251, 252; 324/219–221, 512, 753
See application file for complete search history.

(56) References Cited

U.S. PATENT DOCUMENTS
4,974,168 A * 11/1990 Marx ..................... 702/187
5,046,020 A * 9/1991 Filkin .................... 706/25
5,331,550 A * 7/1994 Stafford et al. ......... 382/128

(Continued)

OTHER PUBLICATIONS

Osama Moselhi et al., "classification of defects in Sewer pipes using Neural Networks", Sep. 2000, Journal of Infrastructure (1) system, pp. 97-104.*

(Continued)

*Primary Examiner*—Sheela Chawan
(74) *Attorney, Agent, or Firm*—Ogilvy Renault LLP

(57) ABSTRACT

In accordance with a first aspect of the present invention, there is provided a method for detecting a defect on a portion of an element comprising the steps of: acquiring an image of said portion; analyzing said image to highlight problematic regions of said portion; calculating a probability that said problematic region is a defect; if said probability is higher than a threshold value, determining a position of said defect on said element. Another method for classifying a defect on an element is provided. The method comprises: acquiring an image of said defect; calculating a probability that said defect corresponds to one of a series of types of defects; if said probability is higher than a threshold value, determining that said defect is a defect of that particular type. Another method for recommending a most suitable rehabilitation technique for a defect is provided. The method comprises: identifying a series of parameters corresponding to said defect; calculating a relative utility for each of a series of potential rehabilitation techniques using rehabilitation profiles; determining a most suitable rehabilitation technique for said defect corresponding to a highest value of said relative utility.

35 Claims, 87 Drawing Sheets

U.S. PATENT DOCUMENTS

| | | | | |
|---|---|---|---|---|
| 5,450,315 | A | * | 9/1995 | Stefanski ..................... 700/48 |
| 5,533,383 | A | * | 7/1996 | Greene et al. ........... 73/40.5 A |
| 5,604,441 | A | * | 2/1997 | Freese et al. ............... 324/663 |
| 5,701,398 | A | * | 12/1997 | Glier et al. .................... 706/41 |
| 5,742,517 | A | * | 4/1998 | Van Den Bosch .......... 382/141 |
| 6,175,380 | B1 | | 1/2001 | Van Den Bosch |
| 6,650,779 | B2 | * | 11/2003 | Vachtesvanos et al. ..... 382/228 |
| 6,757,665 | B1 | * | 6/2004 | Unsworth et al. ............ 706/15 |

OTHER PUBLICATIONS

Abraham D. Chae et al.,(2000) "Utilizing Neural Networks for Condition Assessment of Sanitary Sewer Infrastructure". Proceeding of the 17$^{th}$ Int'l Conference on Robotics and Automation in Construction, Taipei. Taiwan, pp. 423-427.

E.W. Duggan et al., (1995) Pratical Selection of Trenchless Technology "Methods for Sewerage and Drainage System Rehabilitation/Replacemen"t. Proceedings of the North American No-DIG'95, Chicago, III, SB2-pp. 2-68.

Abraham D. Gokhale et al., (1998) Intelligent Systems Evaluation Technologies "An Analysis of Three Promising Options". Proceedings of the North American No DIG 98, New Mexico, pp. 254-256.

Abraham D. Gokhale et al., (2000) "Automated Assessment Technologies for Renewal of Underground Pipeline Infrastructure". Proceeding of the 17$^{th}$ International Conference on Robotics and Automation in Construction, Taipei, Taiwan, pp. 433-438.

M. Kaseco et al., (1994) "Comparison of Traditional and Neural Classification for Pavement—Crack Detection", Journal of Transportation Engineering, ASCE, 120 (4), pp. 552-569.

Moselhi et al., (1993) "Project Selection Considering Risk". Construction Managment and Economics, E & F.N. Spon, 11 (1), pp. 45-52.

Moselhi et al., (1999) "Automated Detection of Defects in Underground Sewer and Water Pipes". Journal of Automation in Construction, Elsevier Science, 8, pp. 581-588.

Moselhi et al., (1999) "An AI-Based System for Detection and Classification of Defects in Sewers". Proceedings in INFRA 99 International Conference, Center of Expertise and Research on Infrastructures In Urban Areas (CERIU), Montreal, CANADA 3B: pp. 42-54.

Moselhi et al., (2000) "Classification of Defects in Sewer Pipes Using Neural Networks". Journal of Infrastructure Systems, ASCE, 6(3) pp. 97-105.

Moselhi et al., (2000) "An Automated System for Rehabilitation of Sewe Pipesr". Canadian Civil Engineer, CSCE, 17 (3), pp. 6-8.

Moselhi et al., (2001) "Multiple Classifiers for Automated Detection of Defects in Sewer Pipes".Proceeding of 2001 International Conference on Rehabilitation of Infrastructures, Waterloo, Canada, pp. 273-278.

Moselhi et al., (1998) "Rehab Select: A decision Support System for Selecting Trenchless Pipeline Rehabilitation Techniques". Proceedings of the North American No-DIG'98, New Mexico, pp. 14-23.

Frederick, Md. (1996) "NeuroShell-2 reference manual". Ward Systems Group Inc.

Ritchie S., (1989) "Digital Image Concepts and Application in Pavement Management", Journal of Transportation Engineering, ASCE, 116 (3), pp. 287-298.

Richie et al., (1991), "Development of an Intelligent System for Automated Pavement Evaluation". Transportation Research Record, National Research Council, 1311, pp. 112-119.

Frederick, Md. (1998) "Scion Image for Windows reference manual". Scion Corporation, Maryland, USA.

Sinha, S. (2001) "Development of an Automated Pipeline Inspection System", Proceeding of the International Symposium on Underground Infrastructure Research, Waterloo, Canada, pp. 279-286.

Shehab-Eldeen, T. et al., 2000, "A database System for Rehabilitation Techniques of Sewer Pipes". Proceedings of the 17th International Conference on Automation and Robotics in Construction., Taipei, Taiwan, pp. 1085-1090.

Shehab-Eldeen (2001) "A decision Support System for Rehabilitation of Sewer Pipes". Canadian Journal of Civil Engineering, CSCE 28(3), pp. 394-401.

Wirahadikusumah R., et al., (1998) "Assessment Technology for Sewer Rehabilitation". Journal of Automation in Construction, Elsevier Science, 7 (4), pp. 259-270.

US 5,870,314, 02/1999, Van Den Bosch (withdrawn)

* cited by examiner

| | Area | Mean | S.D. | X | Y | Length | Major |
|---|---|---|---|---|---|---|---|
| 1. | 10298.00 | 190.81 | 66.39 | 53.65 | 71.71 | 1524.50 | 158.94 |
| 2. | 243.00 | 128.24 | 43.82 | 219.07 | 7.41 | 104.81 | 28.39 |
| 3. | 136.00 | 111.10 | 21.24 | 244.56 | 4.30 | 65.70 | 17.86 |
| 4. | 2159.00 | 188.20 | 70.57 | 282.51 | 35.62 | 368.13 | 61.65 |
| 5. | 292.00 | 131.72 | 32.81 | 202.45 | 17.68 | 89.01 | 31.38 |
| 6. | 192.00 | 109.64 | 23.06 | 202.17 | 51.82 | 118.71 | 24.13 |
| 7. | 241.00 | 130.94 | 42.37 | 178.54 | 59.96 | 101.64 | 23.34 |
| 8. | 1345.00 | 168.22 | 65.38 | 259.09 | 87.75 | 399.50 | 95.43 |
| 9. | 185.00 | 140.76 | 49.97 | 205.39 | 84.36 | 68.87 | 17.46 |
| 10. | 356.00 | 143.15 | 44.28 | 176.45 | 103.95 | 96.43 | 29.89 |
| 11. | 177.00 | 137.53 | 39.02 | 201.72 | 105.62 | 56.63 | 18.03 |
| 12. | 591.00 | 142.98 | 50.42 | 37.24 | 123.74 | 175.10 | 51.35 |
| 13. | 4009.00 | 145.72 | 47.10 | 281.45 | 174.64 | 761.11 | 88.82 |
| 14. | 251.00 | 136.23 | 42.46 | 186.72 | 144.71 | 90.08 | 30.47 |
| 15. | 136.00 | 119.99 | 31.48 | 88.65 | 158.98 | 59.84 | 22.41 |

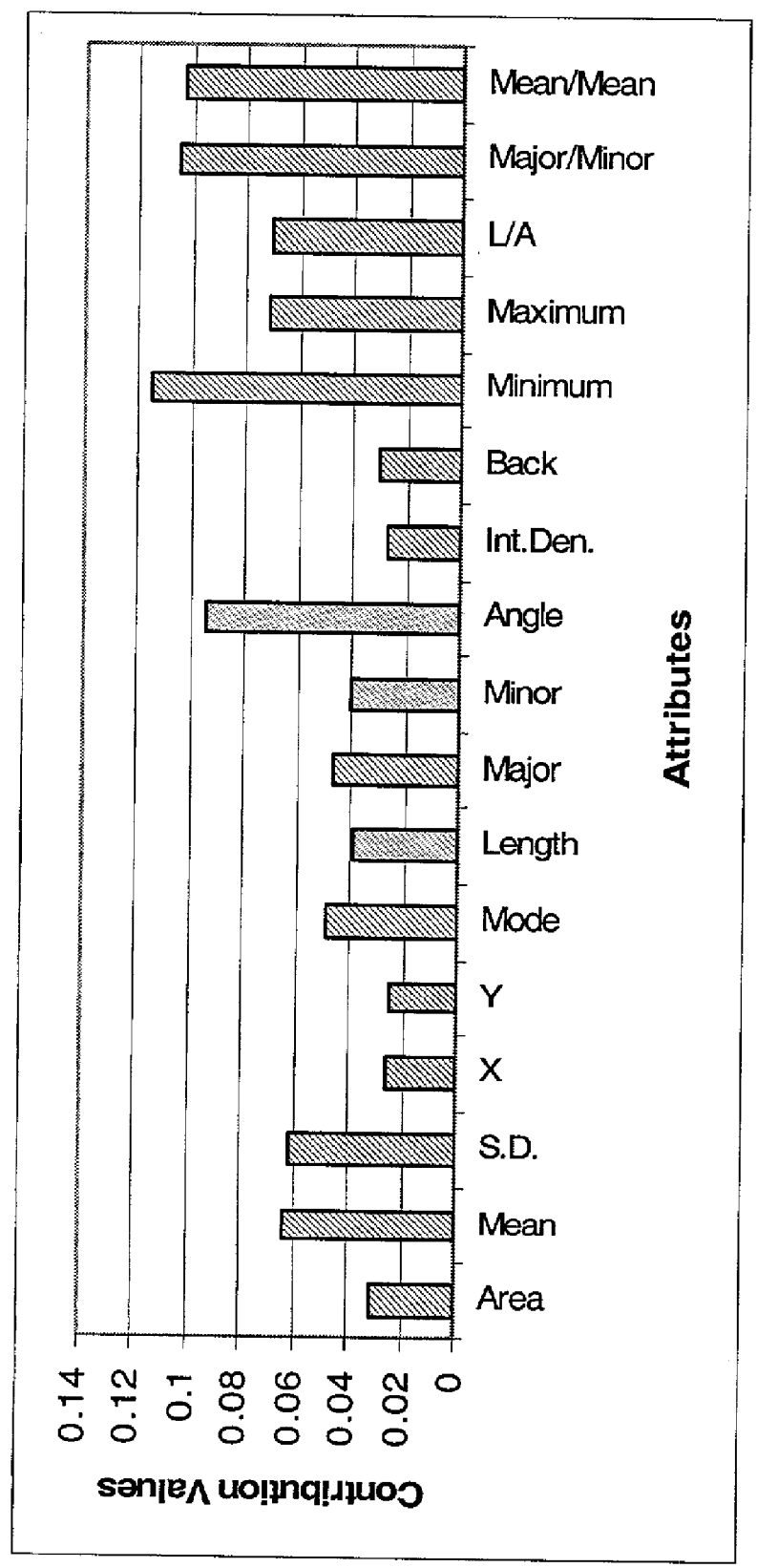
TABLE 49

| Results | Area | Mean | S.D. | X | Y | Length | Major |
|---|---|---|---|---|---|---|---|
| 1. | 2661.00 | 47.26 | 8.76 | 45.90 | 42.65 | 940.85 | 92.06 |
| 2. | 75.00 | 46.45 | 12.18 | 158.67 | 5.32 | 49.36 | 12.07 |
| 3. | 73.00 | 46.25 | 9.46 | 171.18 | 3.55 | 48.28 | 15.81 |
| 4. | 6979.00 | 65.86 | 23.03 | 254.26 | 56.42 | 1431.09 | 127.44 |
| 5. | 151.00 | 50.42 | 10.84 | 234.46 | 6.10 | 76.77 | 16.84 |
| 6. | 63.00 | 42.86 | 3.46 | 24.00 | 7.59 | 43.46 | 14.36 |
| 7. | 147.00 | 52.41 | 17.64 | 148.17 | 18.16 | 73.60 | 16.54 |
| 8. | 315.00 | 49.34 | 12.66 | 113.77 | 25.18 | 172.99 | 22.07 |
| 9. | 77.00 | 45.30 | 10.39 | 166.31 | 20.26 | 51.46 | 11.32 |
| 10. | 524.00 | 61.37 | 24.96 | 181.44 | 75.00 | 212.65 | 46.55 |
| 11. | 77.00 | 44.99 | 6.90 | 47.45 | 72.77 | 49.46 | 16.56 |
| 12. | 51.00 | 43.12 | 3.41 | 34.14 | 92.31 | 34.97 | 11.00 |
| 13. | 96.00 | 61.27 | 22.01 | 303.91 | 113.18 | 44.73 | 15.06 |
| 14. | 61.00 | 44.38 | 3.60 | 2.20 | 112.74 | 31.90 | 12.69 |
| 15. | 186.00 | 51.23 | 16.69 | 52.42 | 129.34 | 115.15 | 19.32 |
| 16. | 86.00 | 55.33 | 14.79 | 39.26 | 125.14 | 39.80 | 15.82 |
| 17. | 82.00 | 43.87 | 5.03 | 25.78 | 126.00 | 52.87 | 15.35 |
| 18. | 97.00 | 44.66 | 5.31 | 15.62 | 128.27 | 57.46 | 12.62 |
| 19. | 187.00 | 53.84 | 19.02 | 302.75 | 136.37 | 98.77 | 24.82 |
| 20. | 170.00 | 60.12 | 19.48 | 37.32 | 142.69 | 65.94 | 21.02 |
| 21. | 59.00 | 60.66 | 30.58 | 262.57 | 136.07 | 33.21 | 10.31 |
| 22. | 89.00 | 46.31 | 7.62 | 2.34 | 144.67 | 55.31 | 17.46 |

|   | AA | AB | AC | AD | AE | AF | AG | AH |
|---|----|----|----|----|----|----|----|----|
| 1 |    |    |    |    | Else |  |  |  |
| 2 |    |    |    |    | Else |  |  |  |
| 3 |    |    |    |    | Else |  |  |  |
| 4 |    |    |    |    | Deposits |  |  |  |
| 5 |    |    |    |    |      |  |  |  |
| 6 |    |    |    |    |      |  |  |  |
| 7 |    |    |    |    | Else |  |  |  |
| 8 |    |    |    |    | Else |  |  |  |
| 9 |    |    |    |    | Else |  |  |  |
| 10 |   |    |    |    | Else |  |  |  |
| 11 |   |    |    |    | Else |  |  |  |
| 12 |   |    |    |    | Else |  |  |  |
| 13 |   |    |    |    | Else |  |  |  |
| 14 |   |    |    |    | Else |  |  |  |
| 15 |   |    |    |    | Else |  |  |  |
| 16 |   |    |    |    | Else |  |  |  |
| 17 |   |    |    |    | Else |  |  |  |
| 18 |   |    |    |    | Else |  |  |  |
| 19 |   |    |    |    | Else |  |  |  |
| 20 |   |    |    |    | Else |  |  |  |
| 21 |   |    |    |    | Else |  |  |  |
| 22 |   |    |    |    | Else |  |  |  |
| 23 |   |    |    |    | Else |  |  |  |
| 24 |   |    |    |    | Else |  |  |  |
| 25 |   |    |    |    | Else |  |  |  |
| 26 |   |    |    |    | Else |  |  |  |
| 27 |   |    |    |    | Else |  |  |  |
| 28 |   |    |    |    | Else |  |  |  |

FIGURE 65A

|   | AA | AB | AC | AD | AE | AF | AG | AH |
|---|----|----|----|----|----|----|----|----|
| 31 |   |    |    |    | Else |  |  |  |
| 32 |   |    |    |    | Else |  |  |  |
| 33 |   |    |    |    | Else |  |  |  |
| 34 |   |    |    |    | Else |  |  |  |
| 35 |   |    |    |    | Else |  |  |  |
| 36 |   |    |    |    |      |  |  |  |
| 37 |   |    |    |    |      |  |  |  |
| 38 |   |    |    |    | Else |  |  |  |
| 39 |   |    |    |    | Else |  |  |  |
| 40 |   |    |    |    | Else |  |  |  |
| 41 |   |    |    |    | Else |  |  |  |
| 42 |   |    |    |    | Else |  |  |  |
| 43 |   |    |    |    | Else |  |  |  |
| 44 |   |    |    |    | Else |  |  |  |
| 45 |   |    |    |    | Else |  |  |  |
| 46 |   |    |    |    | Else |  |  |  |
| 47 |   |    |    |    | Else |  |  |  |
| 48 |   |    |    |    | Else |  |  |  |
| 49 |   |    |    |    | Else |  |  |  |
| 50 |   |    |    |    | Else |  |  |  |
| 51 |   |    |    |    | Else |  |  |  |
| 52 |   |    |    |    |      |  |  |  |
| 53 |   |    |    |    |      |  |  |  |
| 54 |   |    |    |    | Else |  |  |  |
| 55 |   |    |    |    | Else |  |  |  |
| 56 |   |    |    |    | Else |  |  |  |
| 57 |   |    |    |    | Else |  |  |  |
| 58 |   |    |    |    | Else |  |  |  |
| 59 |   |    |    |    | Else |  |  |  |

| | AC | AD | AE | AF | AG | AJ | AK | AL | AM |
|---|---|---|---|---|---|---|---|---|---|
| 1 | | equal | | | | | | Else | |
| 2 | | | | Cross-sectional reductions | | | | | |
| 3 | | | | | | | | | |
| 4 | | | | | | | | | |
| 5 | | | | | | | | | |
| 6 | | | | | | | | | |
| 7 | | | | | | | | | |
| 8 | | | | | | | | | |
| 9 | | | | | | | | | |
| 10 | | | | | | | | | |

FIGURE 69

| | D | E | F | G |
|---|---|---|---|---|
| 1 | ---------- | Else | | |
| 2 | ---------- | Else | | |
| 3 | ---------- | Else | | |
| 4 | ---------- | Else | | |
| 5 | ---------- | Else | | |
| 6 | ---------- | Else | | |
| 7 | | | | |
| 8 | | | | |
| 9 | ---------- | Else | | |
| 10 | ---------- | Else | | |
| 11 | ---------- | Else | | |
| 12 | ---------- | Else | | |
| 13 | ---------- | Else | | |
| 14 | ---------- | Else | | |
| 15 | ---------- | Else | | |
| 16 | | | | |
| 17 | | | | |

FIGURE 79A

| | D | E | F | G |
|---|---|---|---|---|
| 18 | ---------- | Else | | |
| 19 | ---------- | Else | | |
| 20 | ---------- | Else | | |
| 21 | ---------- | Else | | |
| 22 | Infiltration | ---------- | | |
| 23 | ---------- | Else | | |
| 24 | ---------- | Else | | |
| 25 | | | | |
| 26 | | | | |
| 27 | ---------- | Else | | |
| 28 | ---------- | Else | | |
| 29 | ---------- | Else | | |
| 30 | | | | |
| 31 | | | | |
| 32 | Infiltration | ---------- | | |
| 33 | Infiltration | ---------- | | |
| 34 | ---------- | Else | | |
| 35 | ---------- | Else | | |
| 36 | | | | |

FIGURE 79B

| | D | E | F | G |
|---|---|---|---|---|
| 1 | ------------------ | Else | | |
| 2 | ------------------ | Else | | |
| 3 | ------------------ | Else | | |
| 4 | Infiltration | ------------------ | | |
| 5 | ------------------ | Else | | |
| 6 | ------------------ | Else | | |
| 7 | | | | |
| 8 | | | | |
| 9 | ------------------ | Else | | |
| 10 | ------------------ | Else | | |
| 11 | ------------------ | Else | | |
| 12 | ------------------ | Else | | |
| 13 | ------------------ | Else | | |
| 14 | ------------------ | Else | | |
| 15 | ------------------ | Else | | |
| 16 | | | | |

FIGURE 80A

| | D | E | F | G |
|---|---|---|---|---|
| 17 | | | | |
| 18 | ------------------ | Else | | |
| 19 | ------------------ | Else | | |
| 20 | ------------------ | Else | | |
| 21 | ------------------ | Else | | |
| 22 | ------------------ | Else | | |
| 23 | ------------------ | Else | | |
| 24 | ------------------ | Else | | |
| 25 | | | | |
| 26 | | | | |
| 27 | ------------------ | Else | | |
| 28 | Infiltration | ------------------ | | |
| 29 | ------------------ | Else | | |
| 30 | | | | |
| 31 | | | | |
| 32 | Infiltration | ------------------ | | |
| 33 | Infiltration | ------------------ | | |
| 34 | ------------------ | Else | | |
| 35 | ------------------ | Else | | |
| 36 | | | | |
| 37 | | | | |

FIGURE 80B

| | D | E | F | G |
|---|---|---|---|---|
| | File Edit Format Help | | | |
| | Number of row with variable names (blank if none): | | ☒ left/right arrow keys end edit | |
| | First row containing actual training data: | 1 | Size: 100 rows 20 columns | |
| | Note: This is not a commercial spreadsheet and may not load fast enough for large files. The NeuroShell 2 Options men "datagrid" for details. | | | |
| 1 | Infiltration | ------------------ | | |
| 2 | ------------------ | Else | | |
| 3 | ------------------ | Else | | |
| 4 | ------------------ | Else | | |
| 5 | ------------------ | Else | | |
| 6 | ------------------ | Else | | |
| 7 | | | | |
| 8 | | | | |
| 9 | ------------------ | Else | | |
| 10 | ------------------ | Else | | |
| 11 | ------------------ | Else | | |
| 12 | ------------------ | Else | | |
| 13 | ------------------ | Else | | |
| 14 | ------------------ | Else | | |
| 15 | ------------------ | Else | | |
| 16 | | | | |
| 17 | | | | |

FIGURE 81A

| | D | E | F | G |
|---|---|---|---|---|
| 18 | ------------------ | Else | | |
| 19 | ------------------ | Else | | |
| 20 | ------------------ | Else | | |
| 21 | ------------------ | Else | | |
| 22 | ------------------ | Else | | |
| 23 | ------------------ | Else | | |
| 24 | ------------------ | Else | | |
| 25 | | | | |
| 26 | | | | |
| 27 | ------------------ | Else | | |
| 28 | ------------------ | Else | | |
| 29 | ------------------ | Else | | |
| 30 | | | | |
| 31 | | | | |
| 32 | Infiltration | ------------------ | | |
| 33 | Infiltration | ------------------ | | |
| 34 | ------------------ | Else | | |
| 35 | ------------------ | Else | | |
| 36 | | | | |
| 37 | | | | |
| 38 | | | | |

FIGURE 81B

| | AC | AD | AE | AF | AG | AH | AI | AJ | AK | AL |
|---|---|---|---|---|---|---|---|---|---|---|
| 1 | | | Else | | | | | | | |
| 2 | | | Else | | | | | | | |
| 3 | | | Else | | | | | | | |
| 4 | | equal | | | | Else | | | | |
| 5 | | | Else | | | | | | | |
| 6 | | | Else | | | | | | | |
| 7 | | | | | | | | | | |
| 8 | | | | | | | | | | |
| 9 | | | Else | | | | | | | |
| 10 | | | Else | | | | | | | |
| 11 | | | Else | | | | | | | |
| 12 | | | Else | | | | | | | |
| 13 | | | Else | | | | | | | |
| 14 | | | Else | | | | | | | |
| 15 | | | Else | | | | | | | |
| 16 | | | | | | | | | | |
| 17 | | | | | | | | | | |

FIGURE 82A

| | AC | AD | AE | AF | AG | AH | AI | AJ | AK | AL |
|---|---|---|---|---|---|---|---|---|---|---|
| 18 | | | Else | | | | | | | |
| 19 | | | Else | | | | | | | |
| 20 | | | Else | | | | | | | |
| 21 | | | Else | | | | | | | |
| 22 | | equal | | | | | | | | Else |
| 23 | | | Else | | | | | | | |
| 24 | | | Else | | | | | | | |
| 25 | | | | | | | | | | |
| 26 | | | | | | | | | | |
| 27 | | | Else | | | | | | | |
| 28 | | equal | | | | Else | | | | |
| 29 | | | Else | | | | | | | |
| 30 | | | | | | | | | | |
| 31 | | | | | | | | | | |
| 32 | | | Infiltration | | | | | | | |
| 33 | | | Infiltration | | | | | | | |
| 34 | | | Else | | | | | | | |
| 35 | | | Else | | | | | | | |
| 36 | | | | | | | | | | |

| | D | E | F | G |
|---|---|---|---|---|
| 1 | ---------------- | Else | | |
| 2 | ---------------- | Else | | |
| 3 | ---------------- | Else | | |
| 4 | ---------------- | Else | | |
| 5 | ---------------- | Else | | |
| 6 | ---------------- | Else | | |
| 7 | ---------------- | Else | | |
| 8 | Crack | ---------------- | | |
| 9 | ---------------- | Else | | |
| 10 | ---------------- | Else | | |
| 11 | ---------------- | Else | | |
| 12 | Crack | ---------------- | | |
| 13 | ---------------- | Else | | |
| 14 | ---------------- | Else | | |
| 15 | Crack | ---------------- | | |
| 16 | | | | |
| 17 | | | | |
| 18 | ---------------- | Else | | |
| 19 | ---------------- | Else | | |
| 20 | ---------------- | Else | | |
| 21 | ---------------- | Else | | |
| 22 | | | | |
| 23 | | | | |

FIGURE 89A

| | D | E | F | G |
|---|---|---|---|---|
| 24 | Crack | ---------------- | | |
| 25 | ---------------- | Else | | |
| 26 | | | | |
| 27 | | | | |
| 28 | ---------------- | Else | | |
| 29 | ---------------- | Else | | |
| 30 | | | | |
| 31 | | | | |
| 32 | ---------------- | Else | | |
| 33 | Crack | ---------------- | | |
| 34 | ---------------- | Else | | |
| 35 | ---------------- | Else | | |
| 36 | ---------------- | Else | | |
| 37 | ---------------- | Else | | |
| 38 | ---------------- | Else | | |
| 39 | ---------------- | Else | | |
| 40 | ---------------- | Else | | |
| 41 | | | | |
| 42 | | | | |

FIGURE 89B

| | D | E | F | G |
|---|---|---|---|---|
| 1 | ------------------ | Else | | |
| 2 | ------------------ | Else | | |
| 3 | ------------------ | Else | | |
| 4 | ------------------ | Else | | |
| 5 | ------------------ | Else | | |
| 6 | ------------------ | Else | | |
| 7 | ------------------ | Else | | |
| 8 | Crack | ------------------ | | |
| 9 | ------------------ | Else | | |
| 10 | ------------------ | Else | | |
| 11 | ------------------ | Else | | |
| 12 | Crack | ------------------ | | |
| 13 | ------------------ | Else | | |
| 14 | ------------------ | Else | | |
| 15 | Crack | ------------------ | | |
| 16 | | | | |
| 17 | | | | |
| 18 | ------------------ | Else | | |
| 19 | ------------------ | Else | | |
| 20 | ------------------ | Else | | |
| 21 | ------------------ | Else | | |

FIGURE 90A

| | D | E | F | G |
|---|---|---|---|---|
| 22 | | | | |
| 23 | | | | |
| 24 | ------------------ | Else | | |
| 25 | ------------------ | Else | | |
| 26 | | | | |
| 27 | | | | |
| 28 | ------------------ | Else | | |
| 29 | ------------------ | Else | | |
| 30 | | | | |
| 31 | | | | |
| 32 | ------------------ | Else | | |
| 33 | Crack | ------------------ | | |
| 34 | ------------------ | Else | | |
| 35 | ------------------ | Else | | |
| 36 | ------------------ | Else | | |
| 37 | ------------------ | Else | | |
| 38 | ------------------ | Else | | |
| 39 | ------------------ | Else | | |
| 40 | ------------------ | Else | | |
| 41 | | | | |
| 42 | | | | |

FIGURE 90B

|   | AB | AC | AD | AE | AF | AG | AH | AI | AJ | AK | AL |
|---|---|---|---|---|---|---|---|---|---|---|---|
| 1 |   |   |   | Else |   |   |   |   |   |   |   |
| 2 |   |   |   | Else |   |   |   |   |   |   |   |
| 3 |   |   |   | Else |   |   |   |   |   |   |   |
| 4 |   |   |   | Else |   |   |   |   |   |   |   |
| 5 |   |   |   | Else |   |   |   |   |   |   |   |
| 6 |   |   |   | Else |   |   |   |   |   |   |   |
| 7 |   |   |   | Else |   |   |   |   |   |   |   |
| 8 |   |   |   | Crack |   |   |   |   |   |   |   |
| 9 |   |   |   | Else |   |   |   |   |   |   |   |
| 10 |   |   |   | Else |   |   |   |   |   |   |   |
| 11 |   |   |   | Else |   |   |   |   |   |   |   |
| 12 |   |   |   | Crack |   |   |   |   |   |   |   |
| 13 |   |   |   | Else |   |   |   |   |   |   |   |
| 14 |   |   |   | Else |   |   |   |   |   |   |   |
| 15 |   | equal |   |   |   |   |   |   |   | Crack |   |
| 16 |   |   |   |   |   |   |   |   |   |   |   |
| 17 |   |   |   |   |   |   |   |   |   |   |   |
| 18 |   |   |   | Else |   |   |   |   |   |   |   |
| 19 |   |   |   | Else |   |   |   |   |   |   |   |
| 20 |   |   |   | Else |   |   |   |   |   |   |   |
| 21 |   |   |   | Else |   |   |   |   |   |   |   |
| 22 |   |   |   |   |   |   |   |   |   |   |   |

FIGURE 91A

|   | AB | AC | AD | AE | AF | AG | AH | AI | AJ | AK | AL |
|---|---|---|---|---|---|---|---|---|---|---|---|
| 23 |   |   |   |   |   |   |   |   |   |   |   |
| 24 |   |   | equal |   |   |   | Else |   |   |   |   |
| 25 |   |   |   | Else |   |   |   |   |   |   |   |
| 26 |   |   |   |   |   |   |   |   |   |   |   |
| 27 |   |   |   |   |   |   |   |   |   |   |   |
| 28 |   |   | equal |   |   |   |   |   |   |   | Else |
| 29 |   |   |   | Else |   |   |   |   |   |   |   |
| 30 |   |   |   |   |   |   |   |   |   |   |   |
| 31 |   |   |   |   |   |   |   |   |   |   |   |
| 32 |   |   |   | Else |   |   |   |   |   |   |   |
| 33 |   |   |   | Crack |   |   |   |   |   |   |   |
| 34 |   |   |   | Else |   |   |   |   |   |   |   |
| 35 |   |   |   | Else |   |   |   |   |   |   |   |
| 36 |   |   |   | Else |   |   |   |   |   |   |   |
| 37 |   |   |   | Else |   |   |   |   |   |   |   |
| 38 |   |   |   | Else |   |   |   |   |   |   |   |
| 39 |   |   |   | Else |   |   |   |   |   |   |   |
| 40 |   |   |   | Else |   |   |   |   |   |   |   |
| 41 |   |   |   |   |   |   |   |   |   |   |   |

FIGURE 91B

| Field Name | Data Type | Description |
|---|---|---|
| ProductID | AutoNumber | Database serial number |
| Method of repair | Text | Commercial name of rehabilitation technique |
| Maximum distance between access points | Number | Maximum allowable distance between access points to the host pipe |
| Maximum degree of bends | Number | Maximum degree of bends of the host pipe |
| Average cost | Number | Cost of product |
| Average duration | Number | Duration to install 500 (m) of pipe in weeks |
| Number of years in business | Number | Years in business of supplier |
| Life expectency | Number | Design life of new pipe |
| Local experience | Text | Does the supplier have an Office in Canada |
| Access type | Text | Type of access required to the host pipe |
| Length of product installed | Number | Number of KM of product installed by the supplier |
| Inovation | Number | Ability of supplier to accomodate none standard designs |
| Coordinates | Number | Phone number |

Field Properties

General | Lookup
Field Size: Long Integer
New Values: Increment
Format:
Caption: Product ID
Indexed: Yes (No Duplicates)

A field name can be up to 64 characters long, including spaces. Press F1 for help on field names.

METHOD AND APPARATUS FOR THE AUTOMATED DETECTION AND CLASSIFICATION OF DEFECTS IN SEWER PIPES

CROSS-REFERENCE TO RELATED APPLICATIONS

The application claims priority of U.S. provisional application No. 60/252,484 filed Nov. 22, 2000.

FIELD OF THE INVENTION

The invention relates to the automated detection and classification of defects. More specifically, it relates to the automatic detection and classification of surface defects in underground sewer pipes, utilizing image analysis techniques and artificial intelligence technology. It also relates to a suitable trenchless rehabilitation technique for sewer pipes.

BACKGROUND OF THE INVENTION

Deterioration of underground infrastructure facilities such as sewer pipes poses a serious problem to most developed urban centers today. Sewer pipes form one of the six most capital intensive infrastructure systems in North America. Their poor status has been reported by many researchers, revealing the presence of many defects that impact their performance. It has been documented that the condition of 40% of the total Canadian sewer system has declined over the last ten years. It has also been documented that 68% of the sewer networks of all Canadian municipalities are described as either in need of repair or not acceptable. It has been estimated that Canada needs to spend $5–7 Billion to restore the condition of its sewer network. The decline in the condition of sewer pipes could, generally, be attributed to two main factors: 1) inadequate preventive maintenance and inspection programs and 2) deterioration of pipes. Inadequate maintenance and inspection is mainly attributed to high cost and inadequate funds received from the governmental agencies. Interviews conducted with several municipal engineers and consultants in Quebec and Ontario revealed that the cost of sewer inspection is about CDN $1.5 per linear meter. The breakdown of this cost is about CDN $1.08/m for the production of the video tape and CDN $0.42/m for the inspection of the video tape. Therefore, about 30% of the total cost is spent on inspection of videotapes. This high percentage is attributed to the current inspection practice that is followed by all municipalities. This current practice is performed manually and is fully dependent on human inspectors.

On the other hand, deterioration of pipes could be due to the aging process. As pipes age, they deteriorate and may ultimately fail to fulfill their intended functions. It has been estimated that the average useful life of most commonly used sewer pipes is about 70 years. Most sewer pipes in North America have been in use for the last 40–50 years. Inadequate inspection and maintenance programs accelerate the rate of deterioration of the pipe until it ultimately fails. But, if regular inspection and maintenance programs are conducted, then the performance and lifetime of the pipes can be significantly improved.

Rehabilitation of sewer systems poses a major challenge for most municipalities as they embark on providing quality service and preserving their infrastructure assets. Sewer rehabilitation methods are numerous and are constantly being developed, benefiting from emerging technologies. The implementation of these methods is driven by the need to improve quality, reduce cost and project's duration. One of the rapidly expanding fields in the sewer rehabilitation industry is trenchless technology. Due to the large number of methods associated with emerging new technologies in this field, selecting the most suitable method manually can be a challenging task. Selection in this environment may also suffer from the limited knowledge and/or experience of the decision-maker, and could result in overlooking some of the suitable methods that could do the job at less cost.

Clearly, if sewer pipes inspection process can be automated, then significant time and money can be saved. Automating this process can also provide an incentive for checking this class of pipes more regularly; this will help municipality engineers to plan ahead and avoid unpleasant surprises. Automating the selection process of the most suitable trenchless rehabilitation techniques will also help in saving the construction industry a considerable amount of money. It will also facilitate transfer of knowledge and experience to new engineers who are involved in sewer pipes rehabilitation projects.

Up until recently, inspection of sewer pipes has been a challenging task. The reason is that 95% of this class of pipes is too small for effective manual, i.e. walk-in, inspection. The need to assess the condition of sewer pipes led to the development of new techniques for inspection. In an effort to develop new techniques, the closed-circuit television (CCTV) camera was first introduced in the 1960s. Later on, other techniques were also introduced such as laser-based scanning and ultrasound inspection systems. Despite the development of other inspection techniques, the CCTV inspection remains to be the most commonly used technique by most municipalities.

The process of CCTV inspection is usually accomplished by mounting the camera on a small robot to facilitate its movement in a pipe, or, alternatively, it could be winched between two manholes. As the robot moves along the pipe, the camera scans its inner surface to capture and record any existing defects. This process yields a videotape. This videotape is played back using a VCR and visually inspected to check the structural and serviceability conditions of the inspected pipe. After defects have been identified and classified, a report is prepared and forwarded to an engineer who recommends, based on his own experience, the most suitable rehabilitation techniques.

To protect the investment made in sewer pipes and to safeguard them against sudden collapses, municipalities inspect them using the CCTV camera, and repair them using various techniques. As described earlier, the techniques by which pipes are inspected and methods of repair are selected are currently performed manually. Performing these activities in this manner is usually associated with a number of problems. These problems are highlighted below.

Manual CCTV Inspection Process

The manual CCTV inspection process of sewer pipes suffers from a number of limitations. The following is a description of these limitations and their effects on the overall performance of the process.

Costly: based on various interviews conducted with several municipal engineers and consultants in Quebec and Ontario, it was estimated that the cost of sewer inspection is about CDN $1.5 per linear meter. This total cost can be grouped into two main categories: 1) cost to produce the videotape and 2) cost to inspect the videotape. These categories constitute $1.08/m and $0.42/m of the total cost, respectively. The cost of producing videotapes includes robots, CCTV (closed circuit television) camera, cables, monitors operators and truck. The cost of videotape inspection includes cost of engineers or other trained personnel required to prepare a report on inspected pipes.

Time consuming: While acquiring data (i.e. producing videotapes) takes only few hours, analyzing them is a very time consuming process. The time needed to analyze videotapes is variable, depending on whether the process is conducted in house (i.e. at a municipality) or at a consultant's office. Various municipal engineers and practitioners revealed that if a videotape is analyzed at a consultant's office, then a typical two hour one could take up to two to three weeks to analyze and prepare a report showing types of defects encountered. But, if the analysis process is conducted in house, then one to two days are required to prepare the report of defects.

Tedious: the nature of the inspection process requires inspectors to watch videotapes for long numbers of hours. This is considered a very tedious and boring process for most engineers and practitioners.

Fertile source of diagnostic errors: the process may lead to diagnostic errors due to a lack of concentration of inspectors.

Manual selection of suitable rehabilitation techniques, i.e. not computer assisted, suffers from a number of limitations. The following is a description of these limitations.

Large pool to select from: numerous sewer rehabilitation techniques are available in the market; each is considered suitable for a certain application. Knowing the various limitations and applications of each method is considered a challenge to engineers and practitioners in this field.

Rapidly developing field: due to the rapidly developing nature of the sewer rehabilitation field, evaluating new products as they come available in the market is not performed promptly by municipal engineers and consultants. This is considered as a major drawback that leads to overlooking new products that could do a better job and/or reduce cost.

Overlooking other feasible techniques: the manual selection process, by nature, is heavily dependent on human memory. This could result in overlooking some of the suitable methods that could do the job at less cost and/or better quality.

Localized source of information: usually the decision to be made, as to which rehabilitation technique should be selected, is limited to senior engineers who have good experience in sewer rehabilitation projects. This does not give the opportunity to new engineers to be easily involved in this domain of projects.

SUMMARY OF THE INVENTION

Accordingly, an object of the present invention is It is an object of the present invention to detect and classify defects in sewer pipes and recommend the most suitable rehabilitation techniques for the detected defects.

It is an object of the present invention to use image analysis techniques, artificial intelligence (AI), database management systems (DBMS) and a decision support system (DSS) to build this detection and classification system.

Clearly, if identification and classification of defects in sewer pipes could be automated, then not only significant time and money could be saved, but also more reliable and productive working environment could be achieved.

Automating these processes could also provide an incentive for assessing sewer networks more regularly as a part of preventive maintenance programs. This could help municipality engineers to plan ahead and avoid unpleasant surprises. Providing a computer-assisting tool in selecting suitable rehabilitation techniques is expected to help new engineers to benefit from the experience and knowledge gained by others. It will also help senior and experienced engineers to be more updated about new technologies that are constantly being developed in the domain of sewer rehabilitation. It will ensure selecting the most suitable rehabilitation technique that satisfies job and user requirements.

A first object of the present invention is to detect, classify defects in sewer pipes and recommend the most suitable rehabilitation techniques for the detected defects using image analysis techniques, artificial intelligence (AI) and data-base management systems (DBMS).

A second object of the present invention is to assist infrastructure engineers in diagnosing defects in water and sewer lines.

A further object of the present invention is to use neural networks for the classification of defects in concrete and clay pipes, namely cracks, joint displacements, reduction of cross-sectional area, and spalling.

Another object of the present invention is to assist municipal engineers and contractors in selecting the most suitable trenchless rehabilitation technique that specifies job conditions and user's requirements and help new and less experienced engineers to benefit from the experience gained by others.

In accordance with a first aspect of the present invention, there is provided a method for detecting a defect on a portion of an element comprising the steps of:
  acquiring an image of said portion;
  analyzing said image to highlight problematic regions of said portion;
  calculating a probability that said problematic region is a defect;
  if said probability is higher than a threshold value, determining a position of said defect on said element.

Another method for classifying a defect on an element is provided. The method comprises:
  acquiring an image of said defect;
  calculating a probability that said defect corresponds to one of a series of types of defects;
  if said probability is higher than a threshold value, determining that said defect is a defect of that particular type.

Another method for recommending a most suitable rehabilitation technique for a defect is provided. The method comprises:
  identifying a series of parameters corresponding to said defect;
  calculating a relative utility for each of a series of potential rehabilitation techniques using rehabilitation profiles;
  determining a most suitable rehabilitation technique for said defect corresponding to a highest value of said relative utility.

Corresponding apparatus, computer products and signals are also provided according to the invention.

For the purpose of the present invention, the following terms are defined below.

The term "gray value" is intended to mean the brightness value of a pixel (0 for black, and 255 for white).

The term "pixel" is intended to the picture element.

The term "area" is intended to mean the area of defect.

The term "mean density" is intended to mean the average gray value of all pixels within the defect.

The term "standard deviation" is intended to mean the standard deviation of the gray values referred to in "mean density" above.

The term "X-Y coordinate" is intended to mean the X-Y coordinates of the center of defect.

The term "modal value" is intended to mean the most frequently occurring gray value referred to in "mean density" above.

The term "perimeter" is intended to mean the parameter of the "area" referred to above.

The term "major axis length" is intended to mean the length of the major axis of the "area" referred to above.

The term "minor axis length" is intended to mean the length of the minor axis of the "area" referred to above.

The term "angle" is intended to mean the angle between the major axis and a line parallel to the x-axis of the image.

The term "integrated density" is intended to mean N*(mean density−modal value of background), where N is the number of pixels within the area of the defect.

The term "modal value of background" is intended to mean the most common gray value of image background.

The term "minimum gray value" is intended to mean the minimum gray value within the defect.

The term "maximum gray value" is intended to mean the maximum gray value within the defect.

The term "ratio of major axis length to minor axis length" is intended to mean the major axis length (as defined above)/minor axis length (as defined above).

The term "CCTV" is intended to mean the Closed Circuit Television.

The term "M" is intended to mean the Magnitude of gradient.

The term "g (x, y)" is intended to mean the pixel locations in an image.

The term "g' x (x, y)" is intended to mean the partial derivative of an image with respect to x.

The term "g' y (x, y)" is intended to mean the partial derivative of an image with respect to y.

The term "Gray value" is intended to mean the brightness value of a pixel (0 for black, and 255 for white).

The term "Pixel" is intended to mean the picture element.

The term "Area" is intended to mean the area of defect in pixels.

The term "Mean density" is intended to mean the average gray value of all pixels within the defect.

The term "Standard deviation" is intended to mean the standard deviation of the gray values referred to in "Mean density" above.

The term "X-Y coordinate" is intended to mean the X-Y coordinates of the center of defect.

The term "Perimeter" is intended to mean the Parameter of the "area" referred to above.

The term "Modal value" is intended to mean the most frequent occurring gray level value referred to in the "mean density" above The term "Major axis length" is intended to mean the length of the major axis of the "area" referred to above.

The term "Minor axis length" is intended to mean the length of the minor axis of the "area" referred to above.

The term "Angle" is intended to mean the angle between the major axis and a line parallel to the x-axis of the image.

The term "Integrated density " is intended to mean the N*(mean density−modal value of background), where N is the number of pixels within the area of the defect.

The term "Modal value of background" is intended to mean the most common gray value of image background.

The term "Minimum gray value" is intended to mean the minimum gray value within the defect.

The term "Maximum gray value" is intended to mean the maximum gray value within the defect.

The term "Ratio of major axis length to minor axis length (Maj./Min.)" is intended to mean the major axis length (as defined above)/minor axis length (as defined above).

The term "Ratio of parameter to area (L/A)" is intended to mean the Parameter of defect (as defined above)/area of defect (as defined above).

The term "Ratio of mean to mean (Mean/Mean)" is intended to mean the mean gray level of defect/mean gray level of image.

BRIEF DESCRIPTION OF THE DRAWINGS

These and other features, aspects and advantages of the present invention will become better understood with regard to the following description and accompanying drawings wherein:

FIG. 24 shows the Output Results of a Case example on Cracks;

FIG. 25 shows the Thresholded Output Results of a Case example on Cracks;

FIG. 32 shows the Classification Results of a Case Example on Infiltration;

FIG. 40 shows the Classification Results of a Case Example on Deposits;

FIG. 48 shows the Classification Results of a Case Example on Cross-sectional Reduction;

Figure 51:
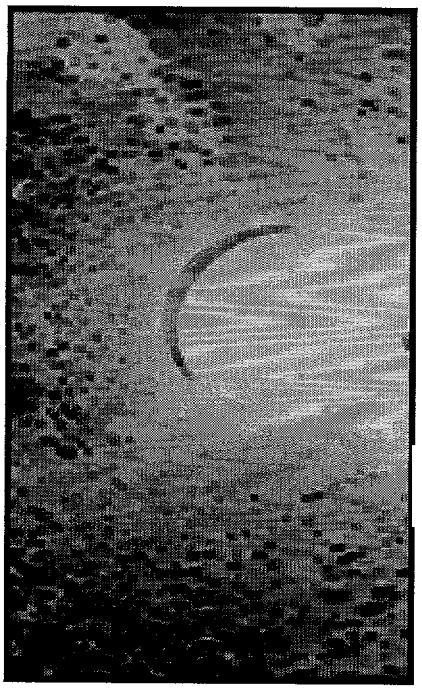
Figure 53:
Figure 50:
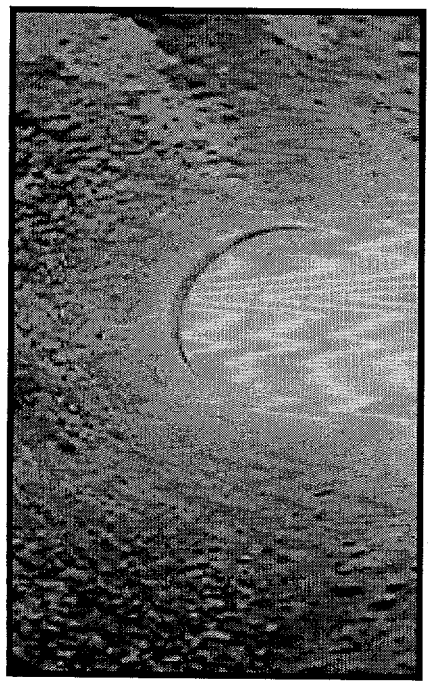
Figure 52:
Figure 54:
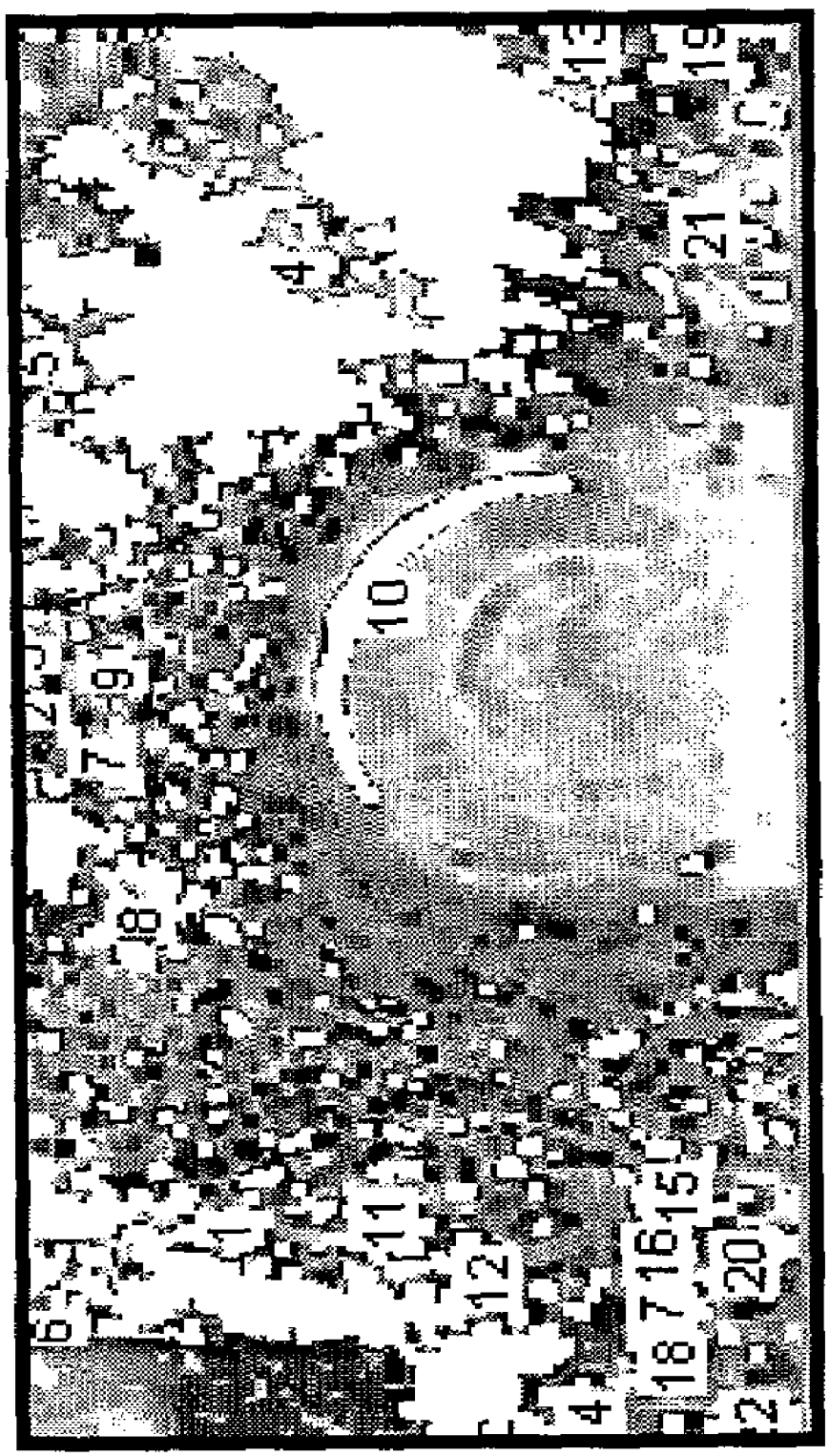
Figure 58:
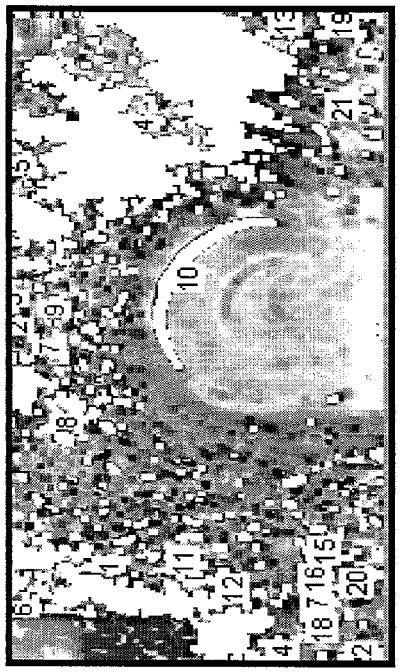
Figure 60:
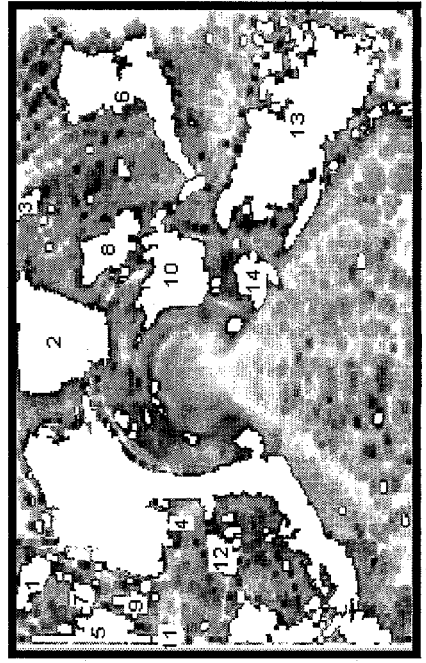
Figure 57:
Figure 59:
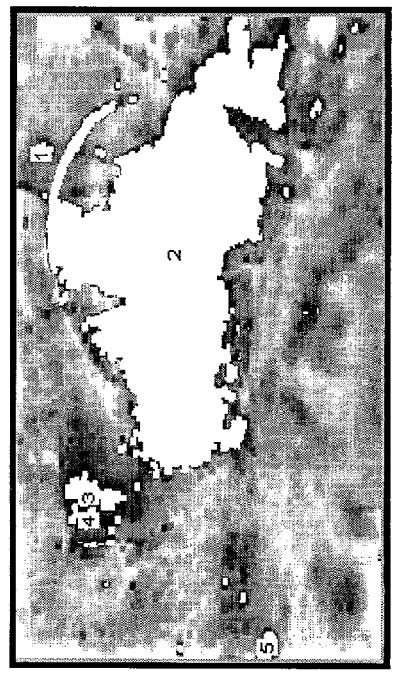
Figure 61:
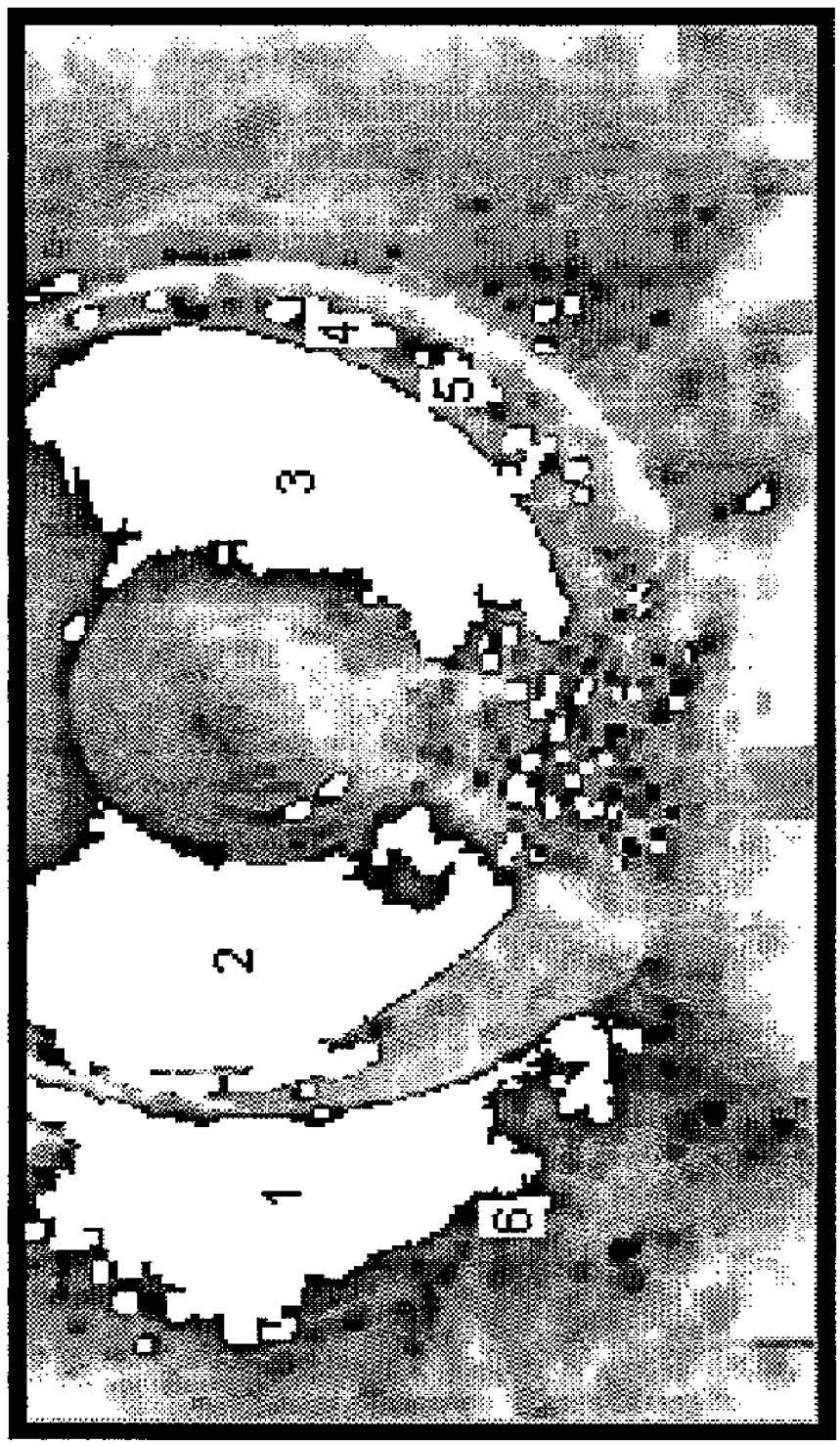
Figure 70:
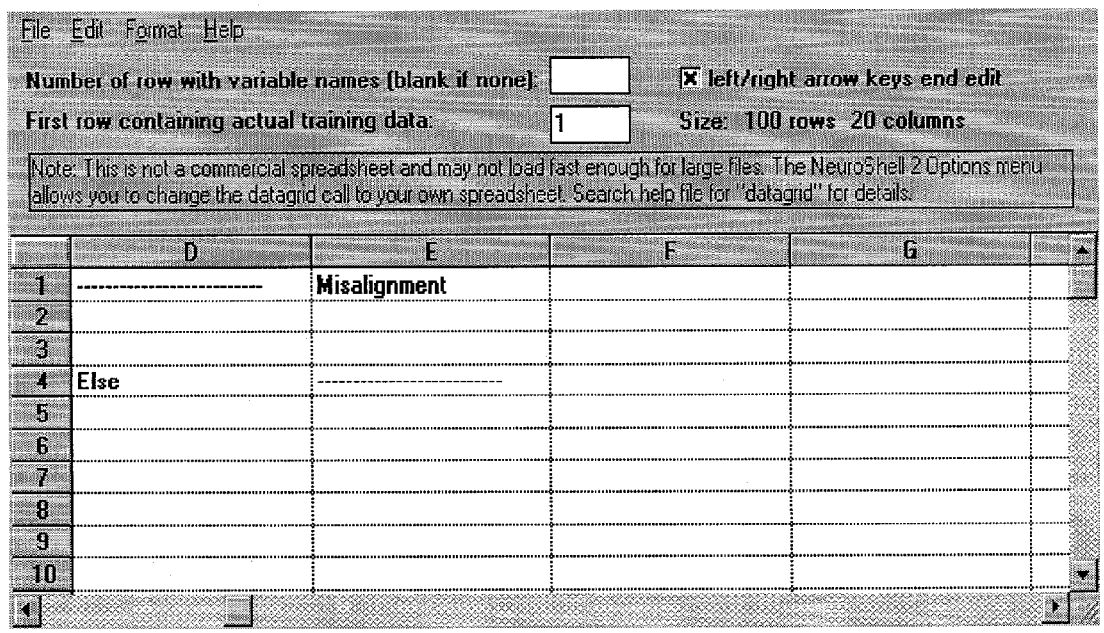
Figure 71:
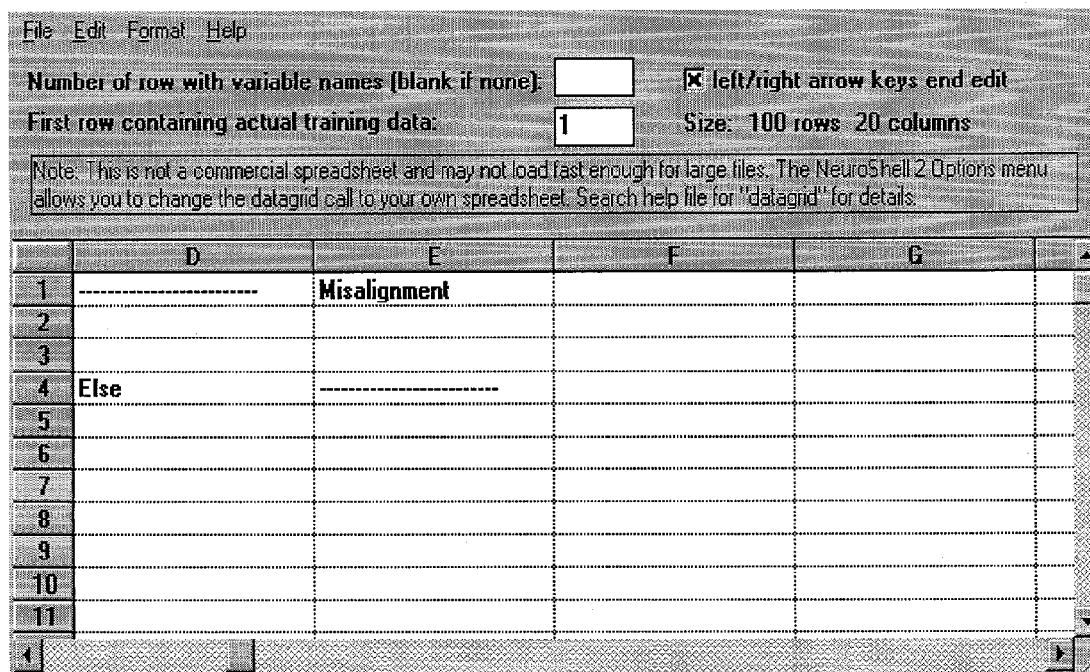
Figures 72, 73:
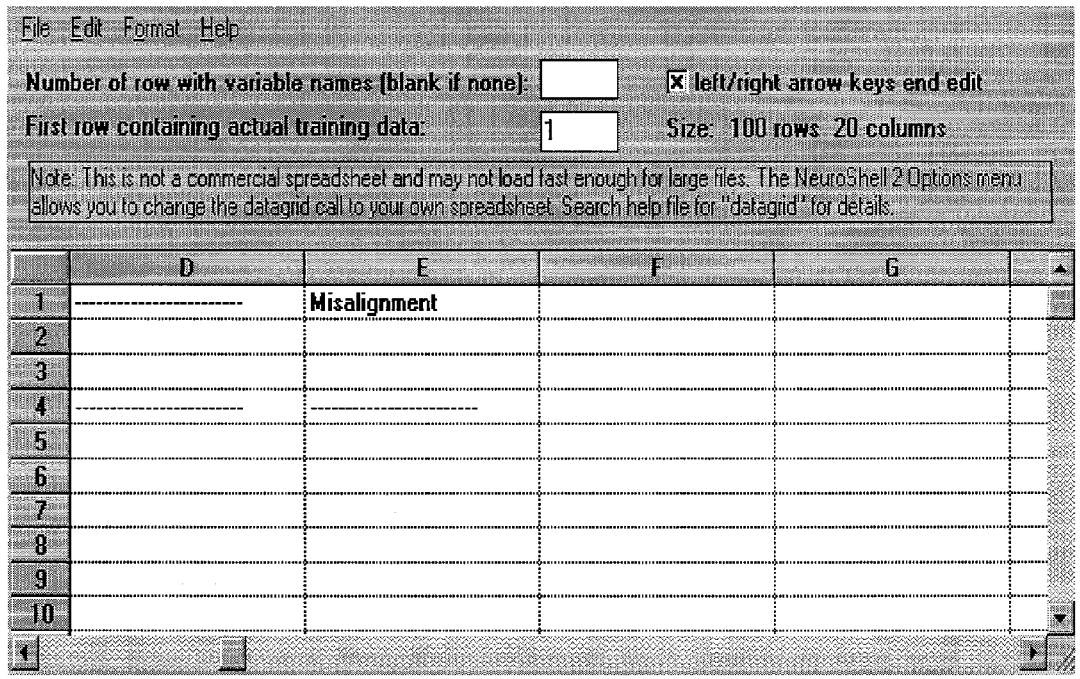
Figure 74:
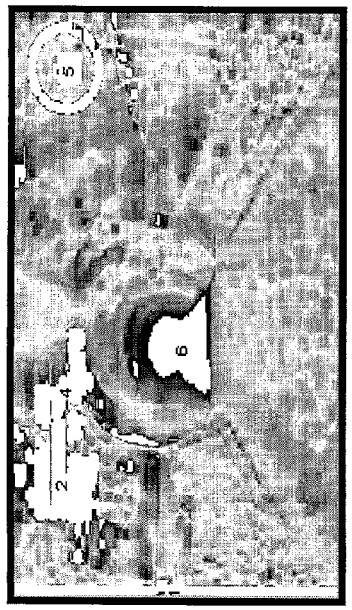
Figure 75:
Figure 76:
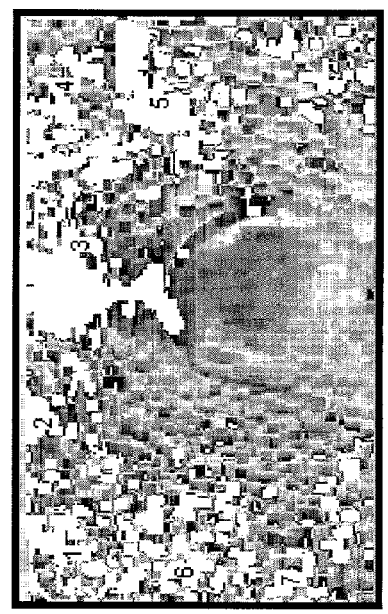
Figure 77:
Figure 78:
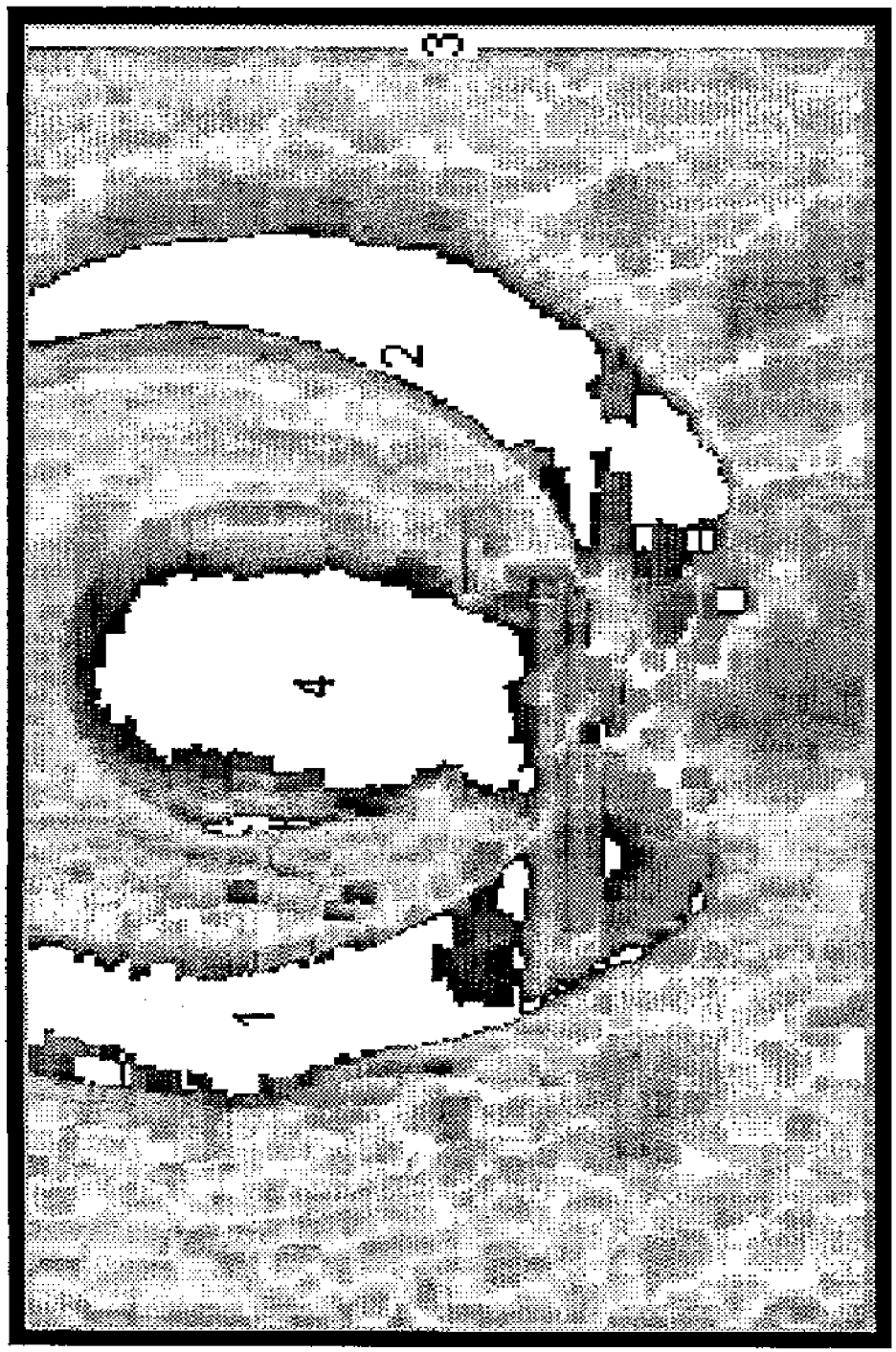
Figure 84:
Figure 83:
Figure 85:
Figure 87:
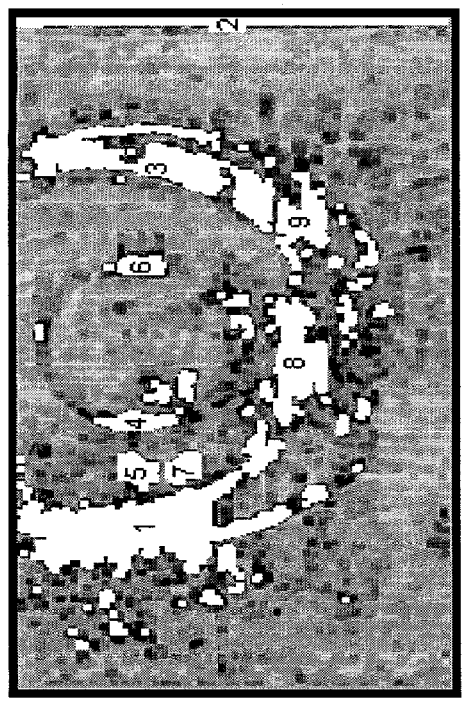
Figure 86:
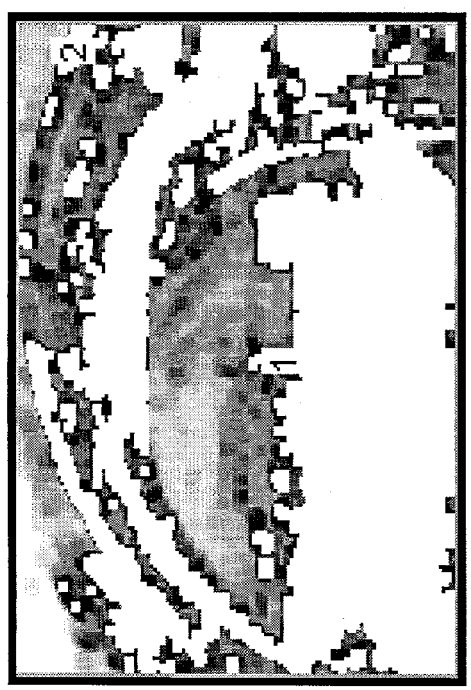
Figure 92:
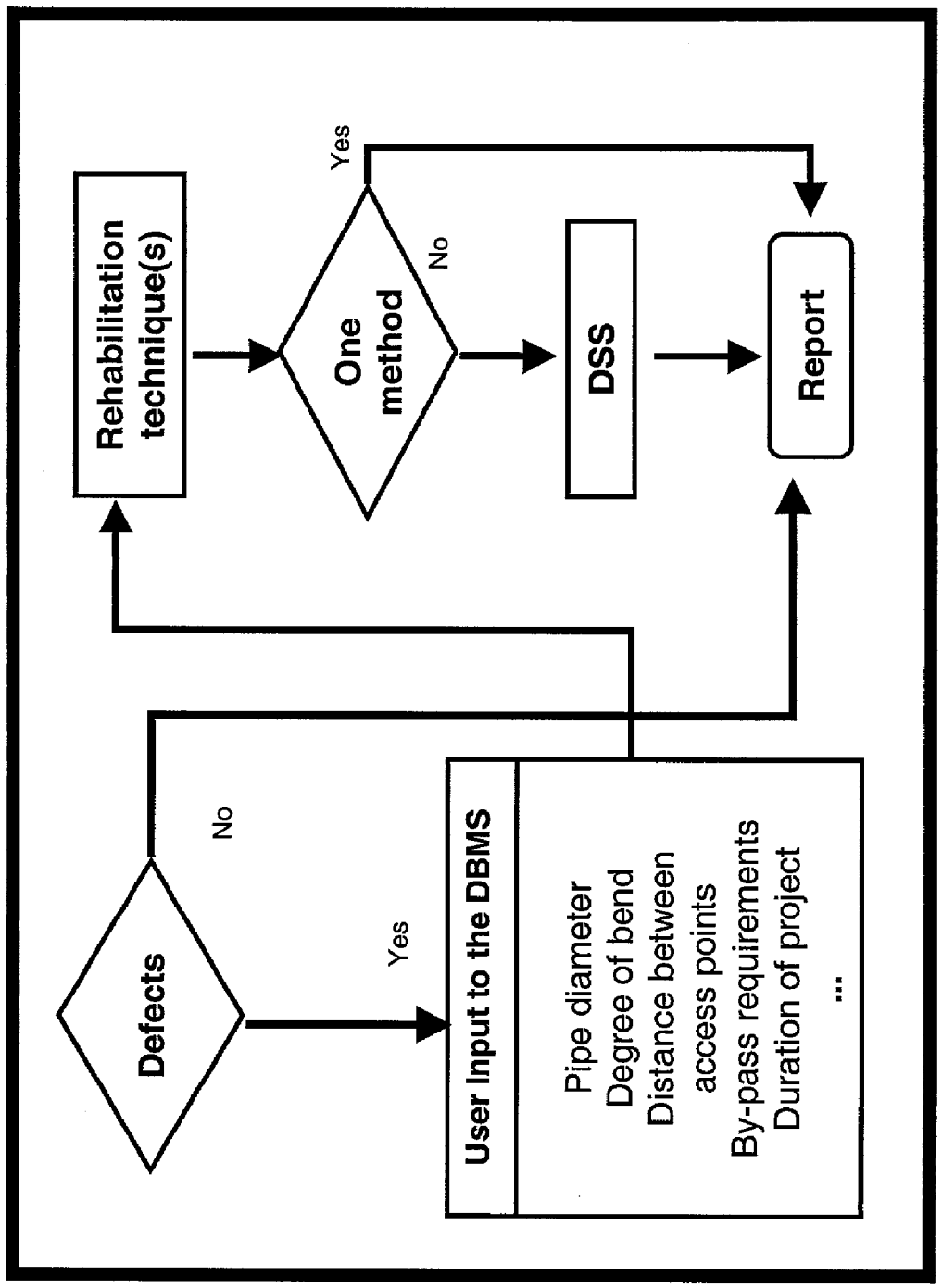
Figure 94:
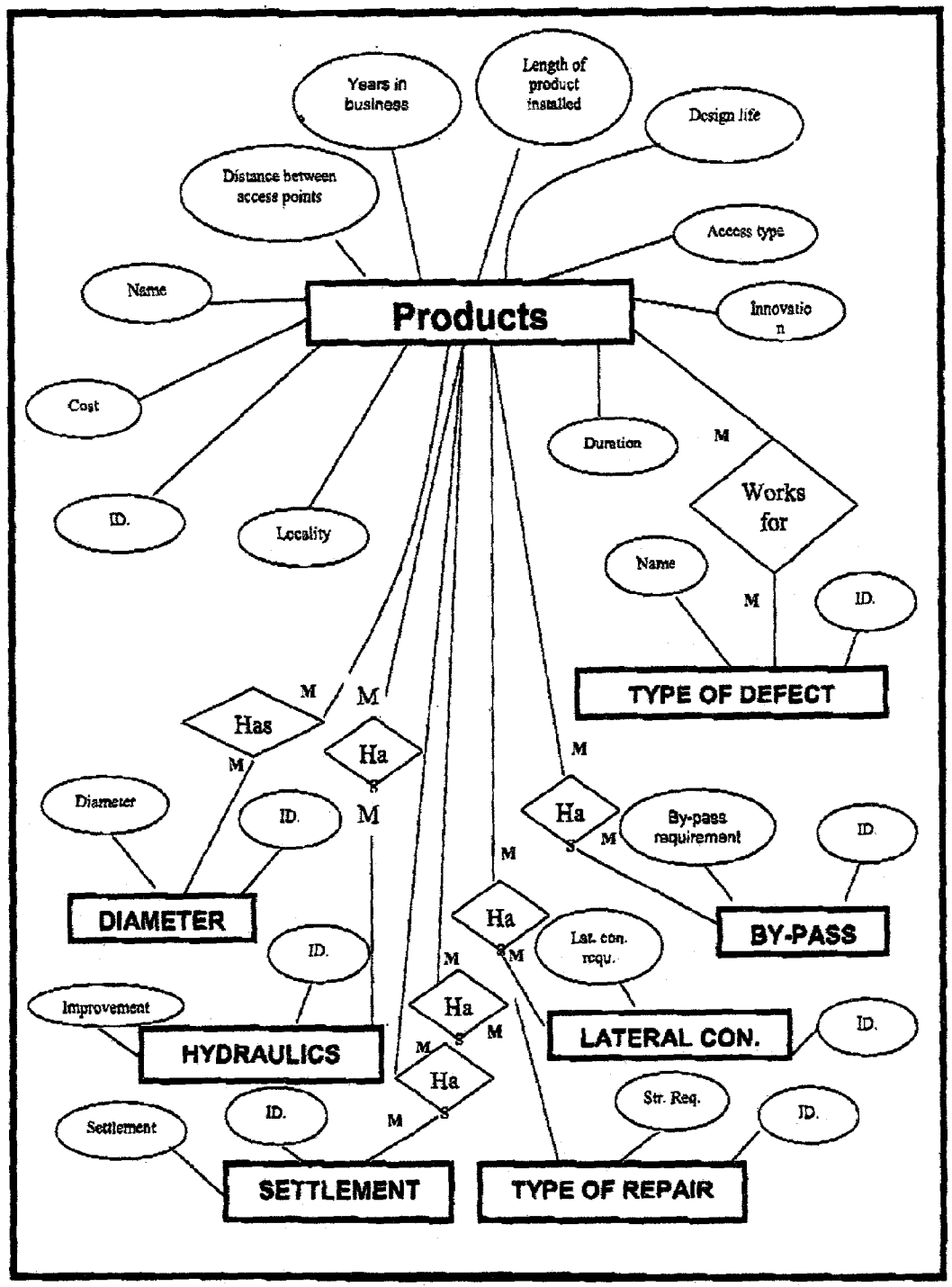
Figure 95:
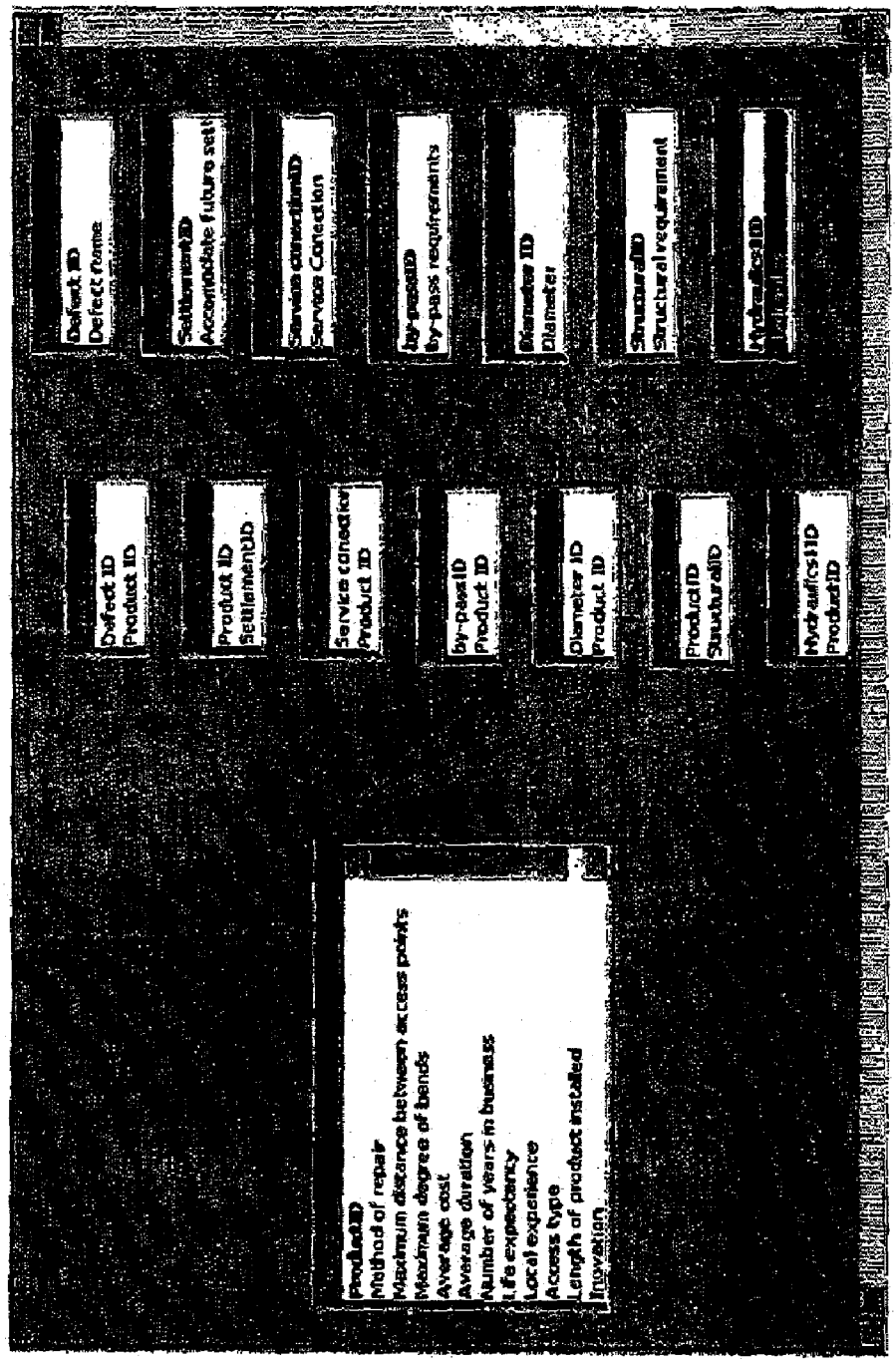
Figure 96:
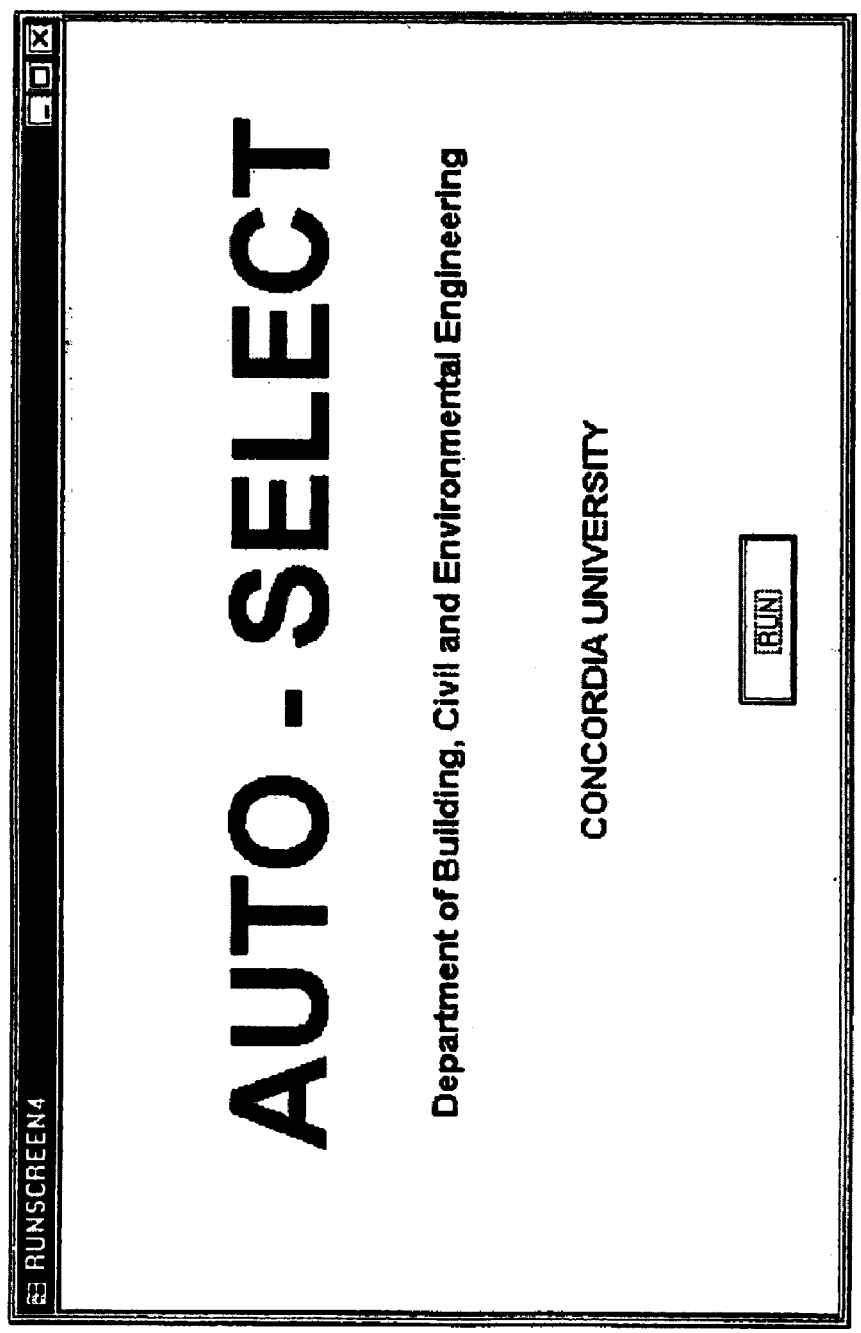
Figure 99:
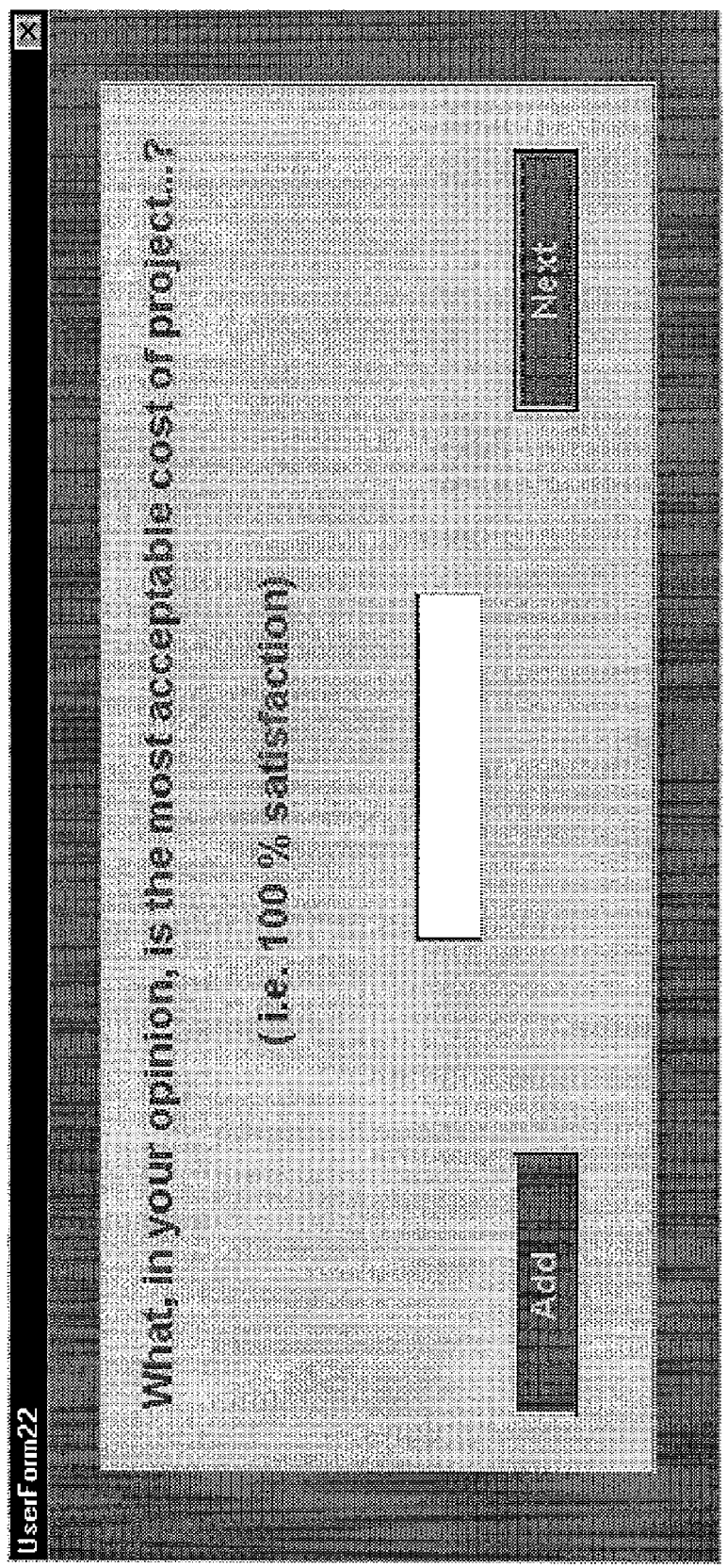
Figure 100:
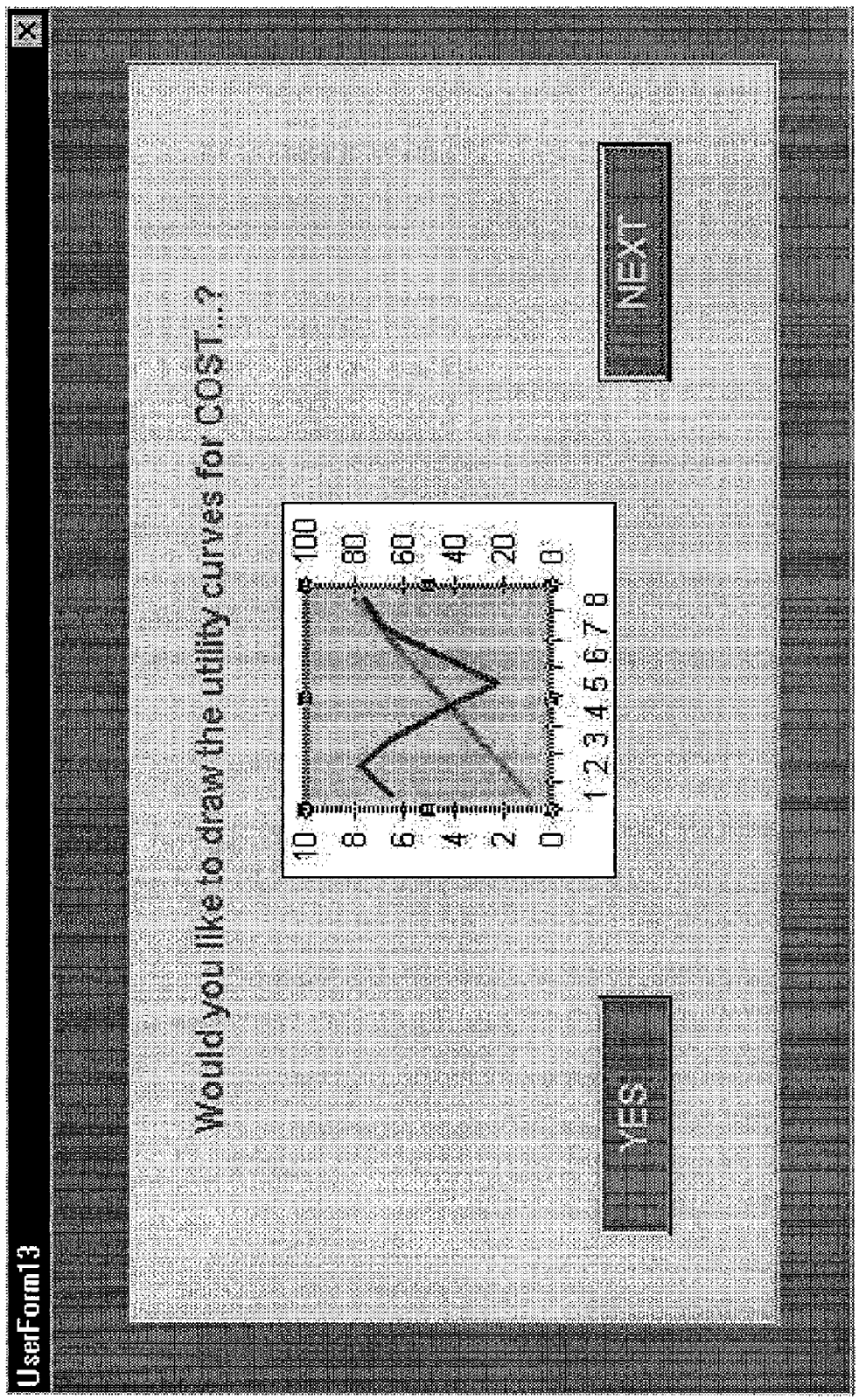
Figure 101:
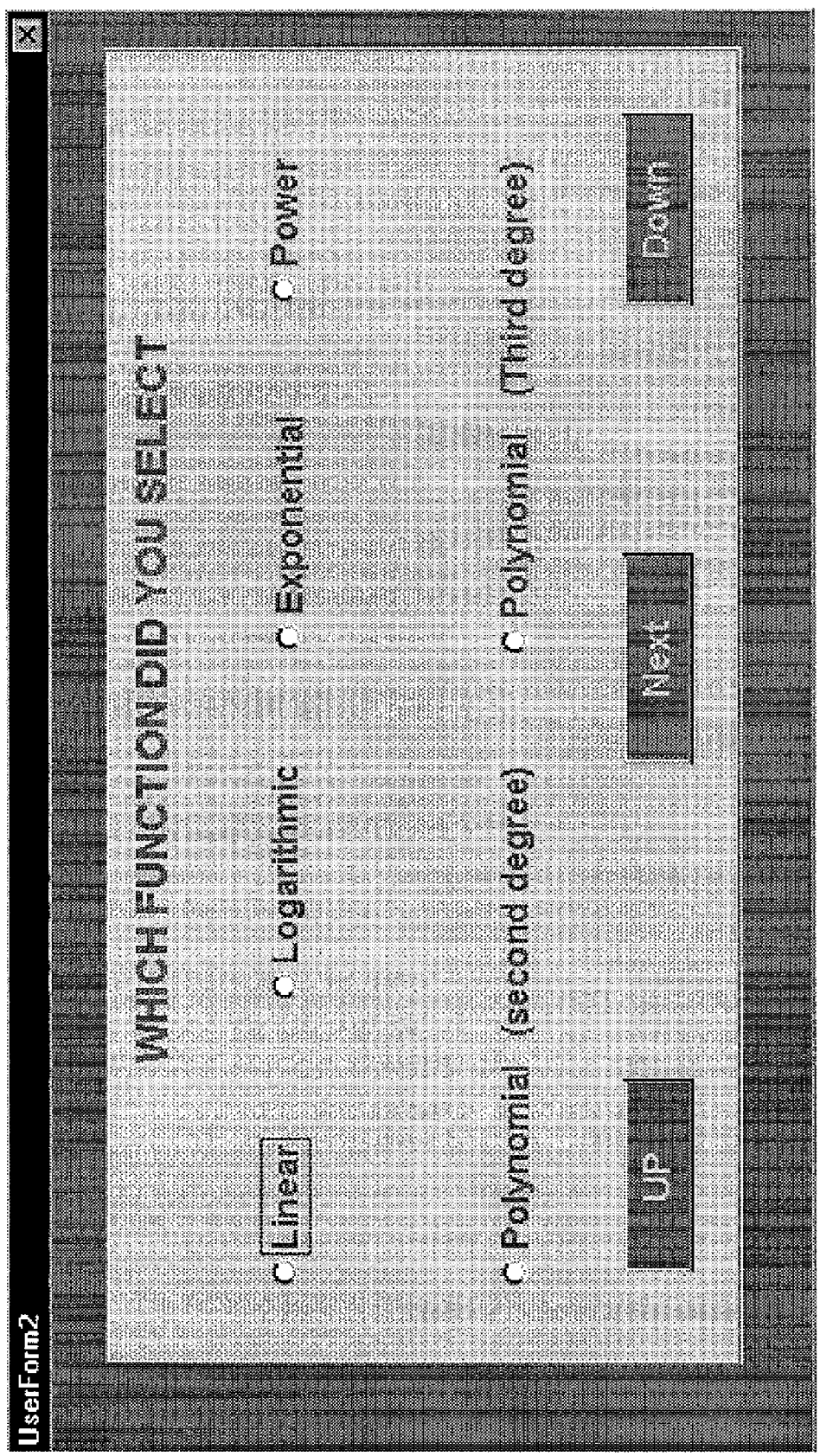
Figure 102:
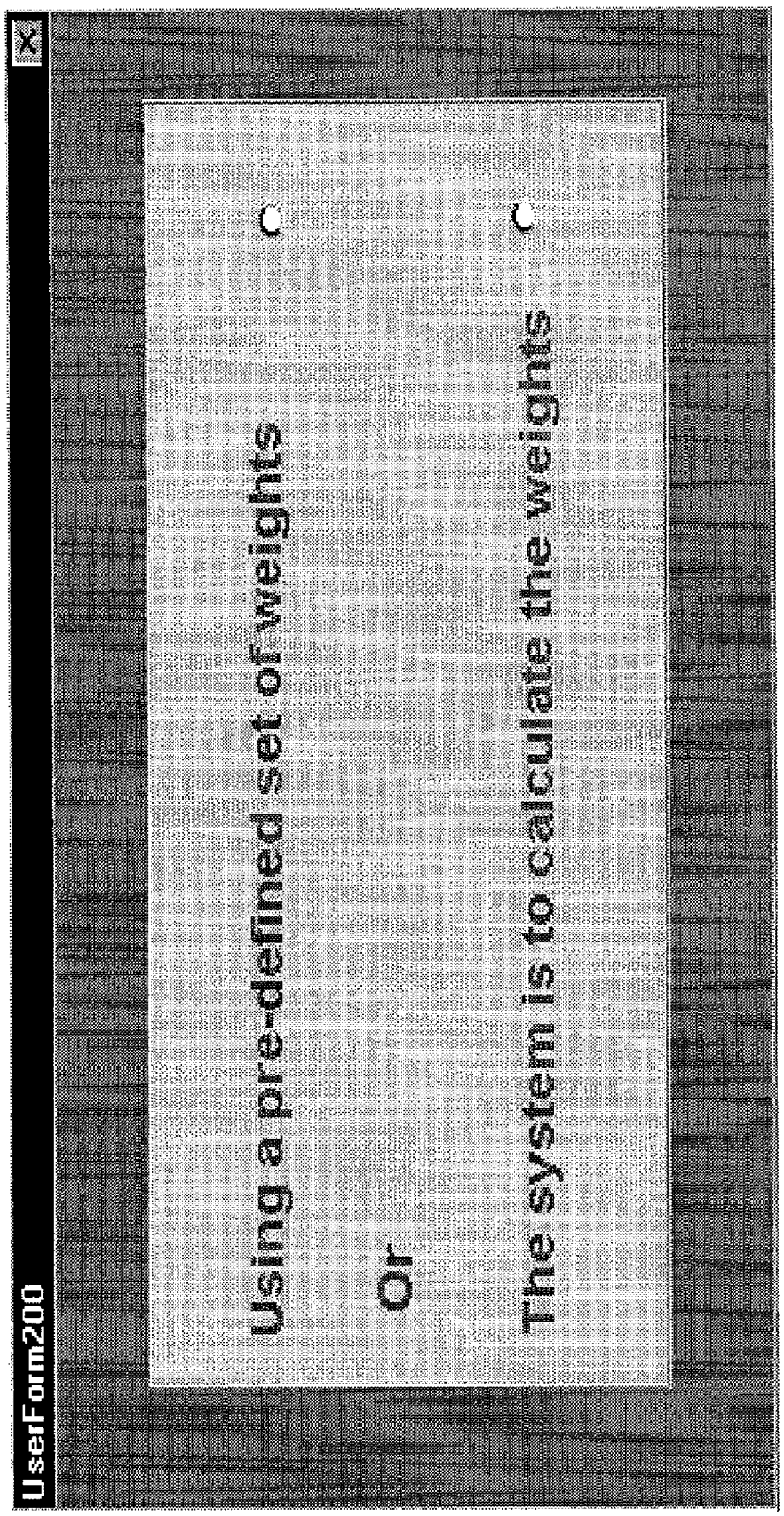
Figure 104:
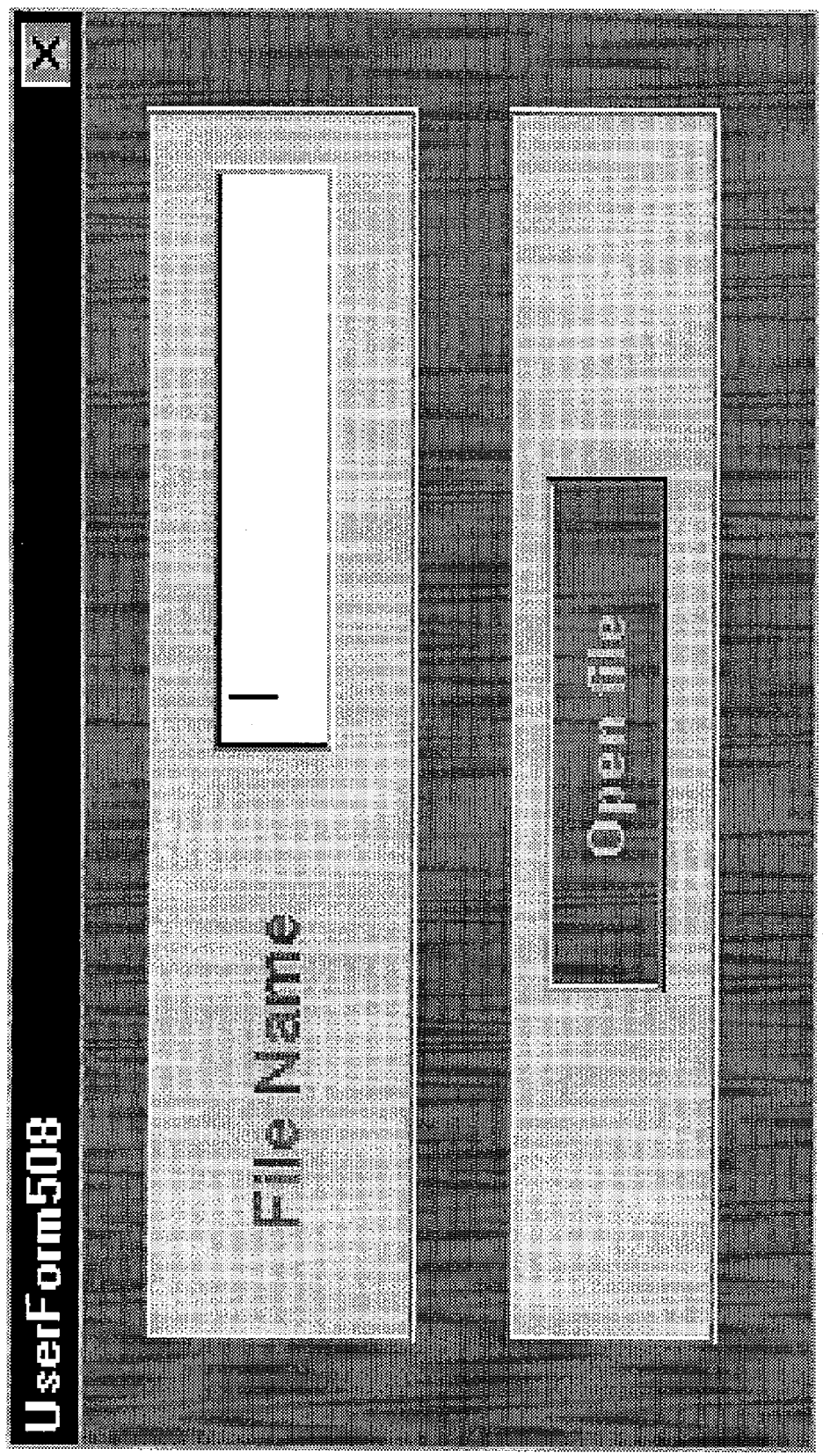
Figure 108:
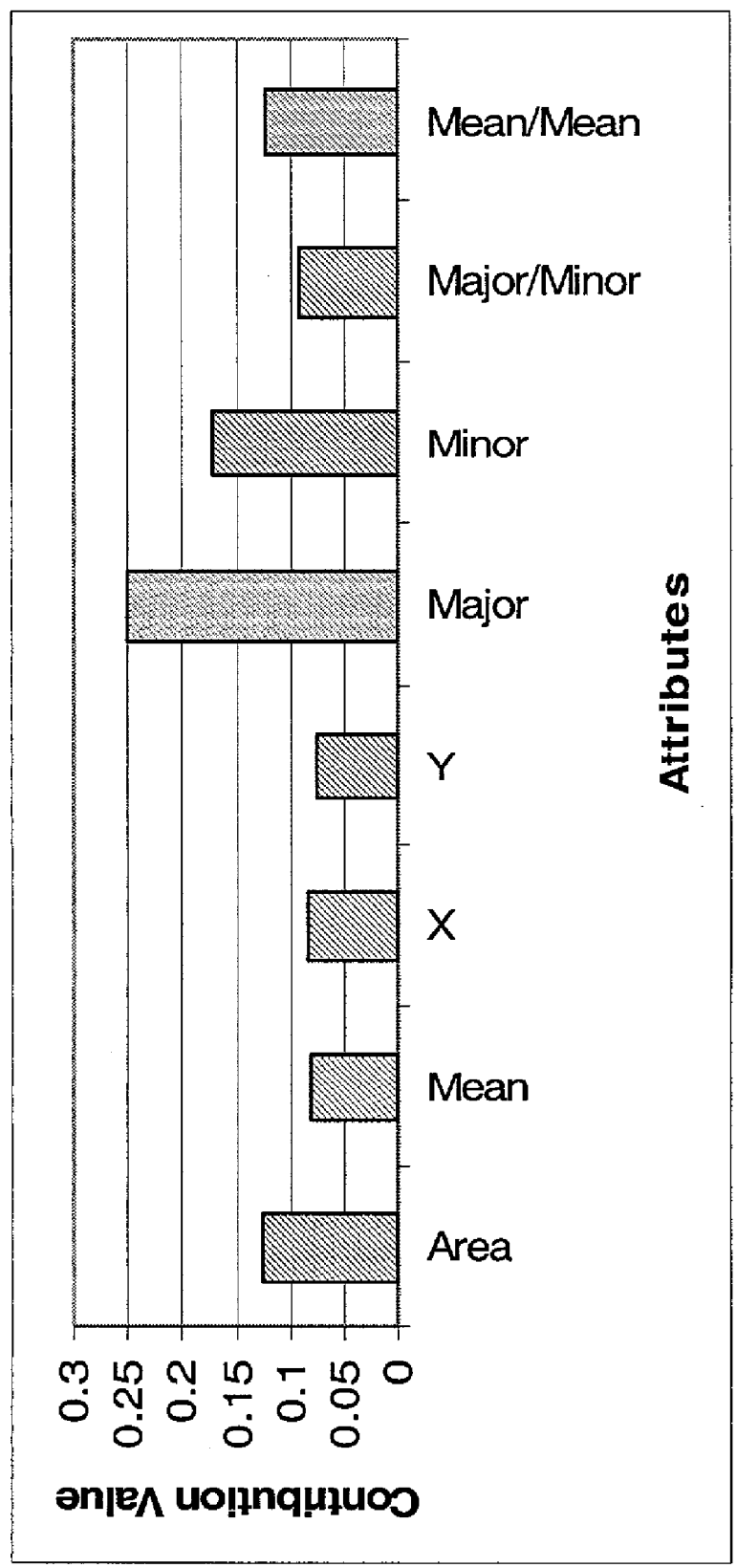
Figure 109:
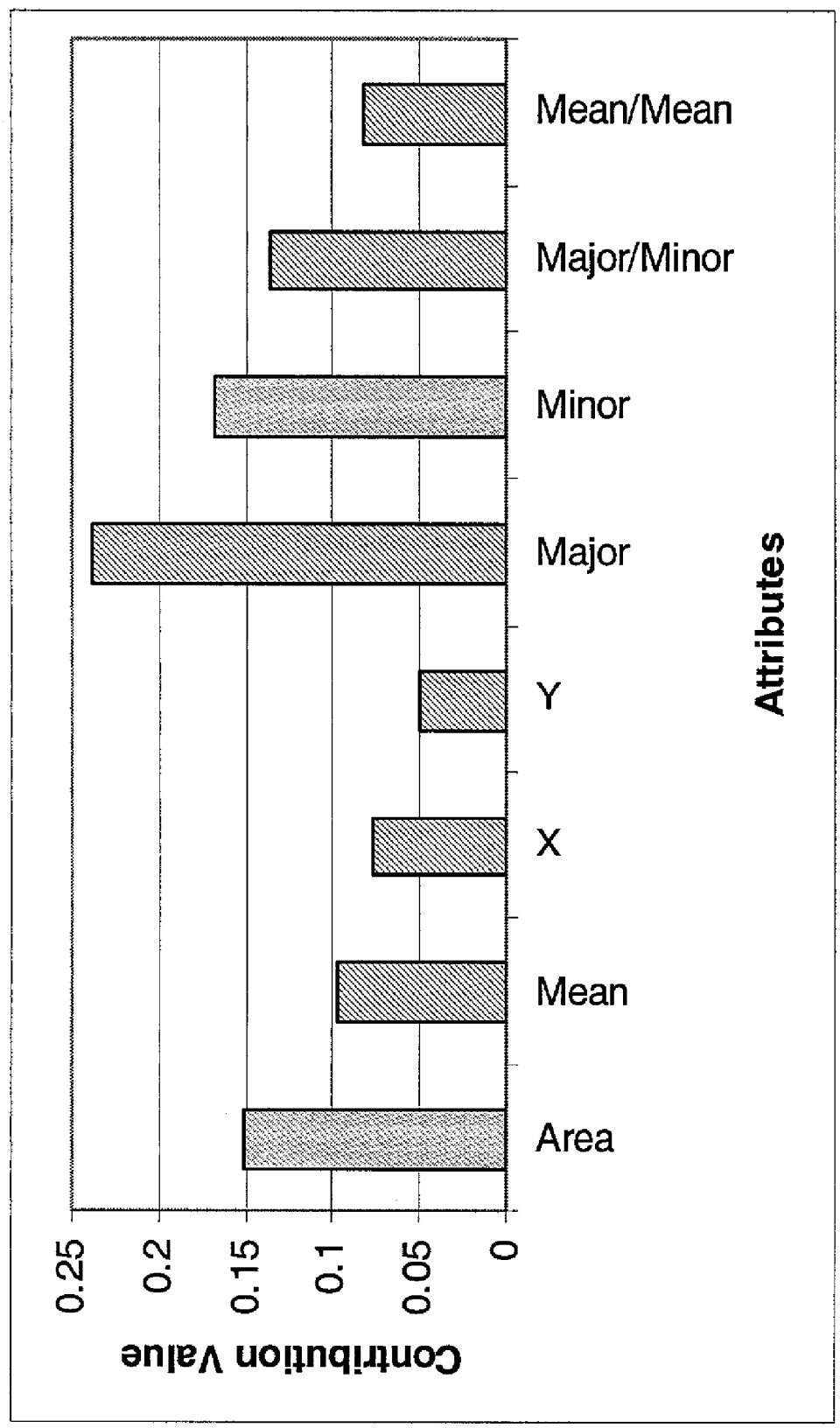
Figure 110:
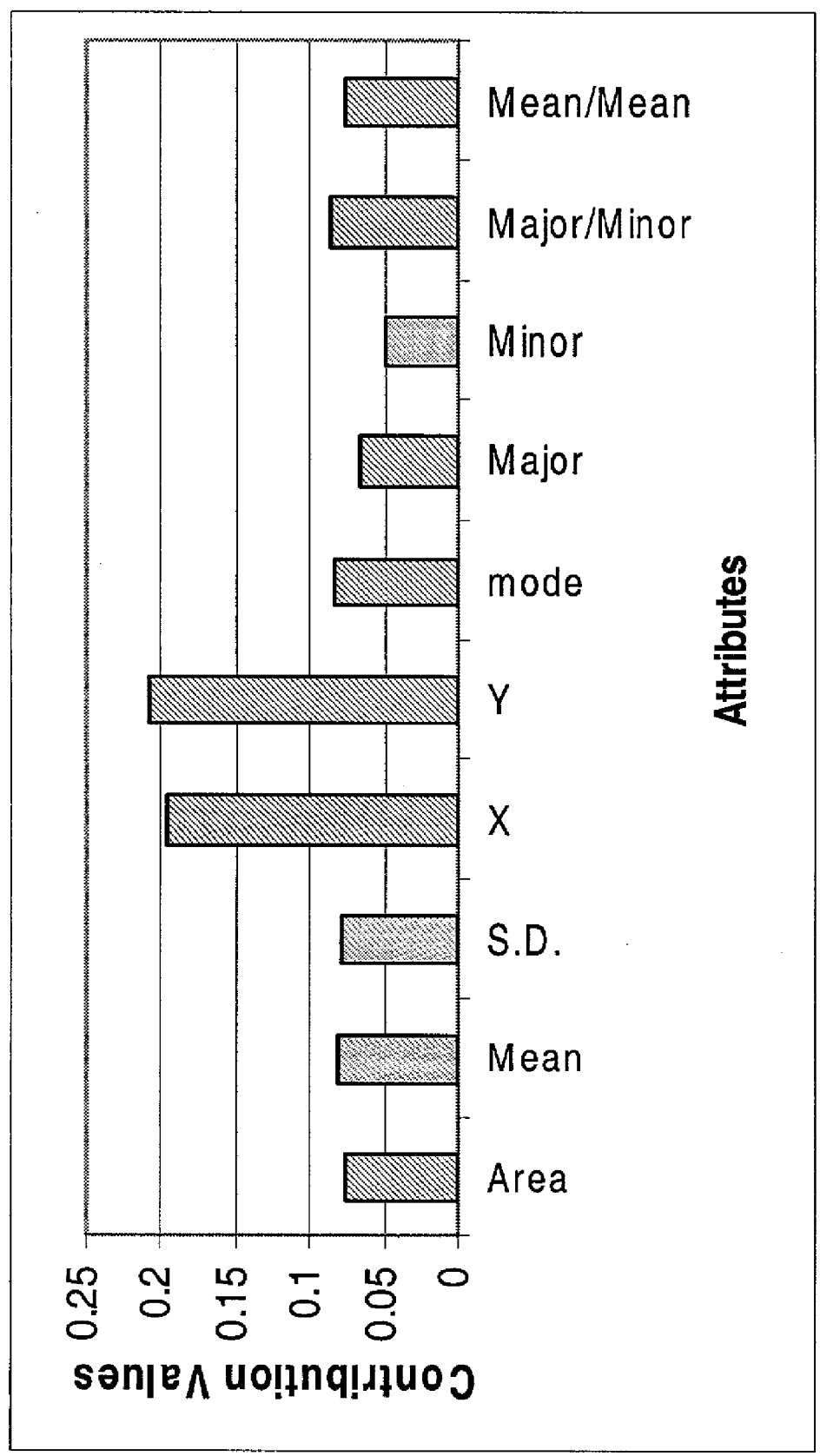
Figure 111:
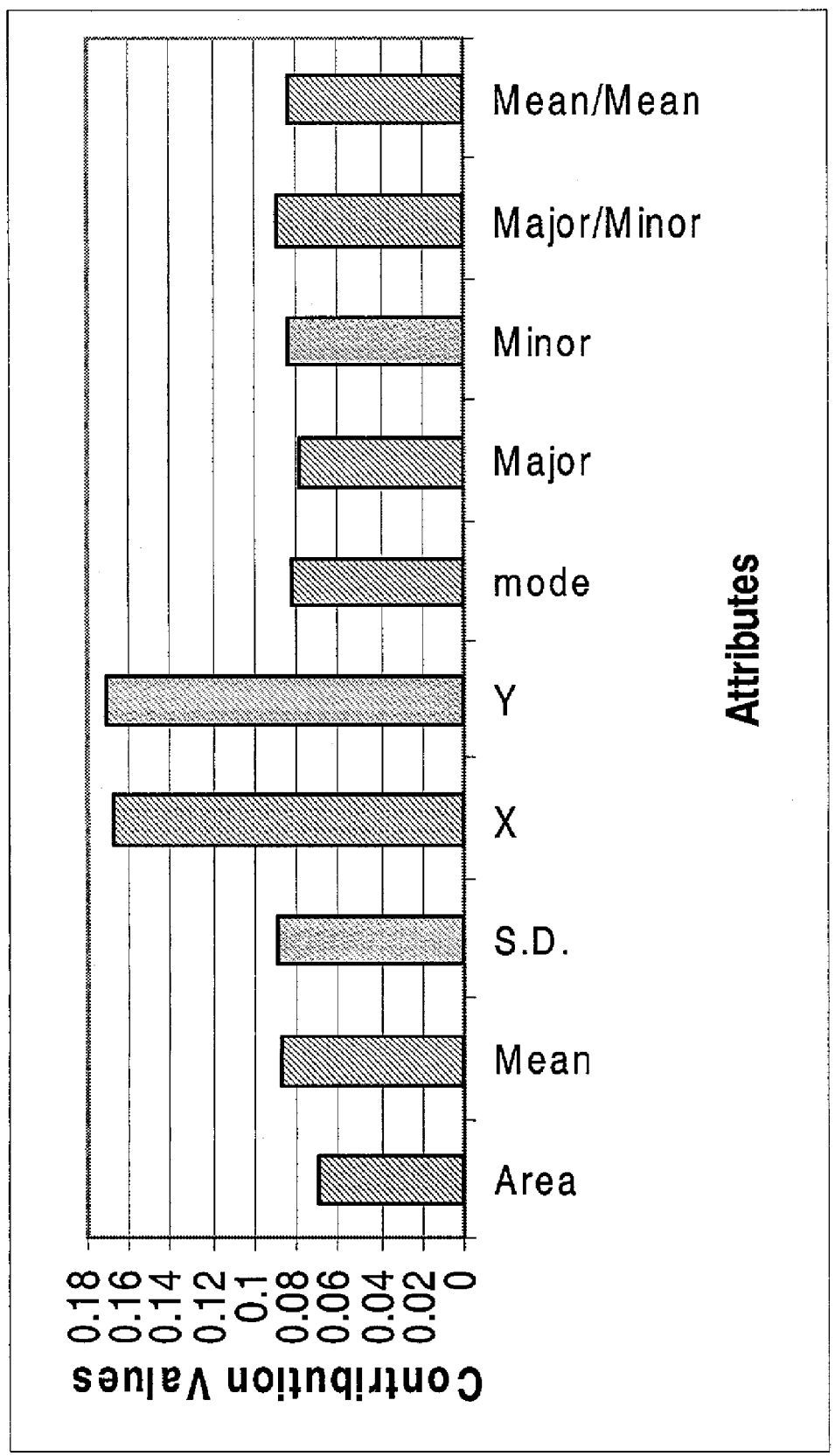
Figure 112:
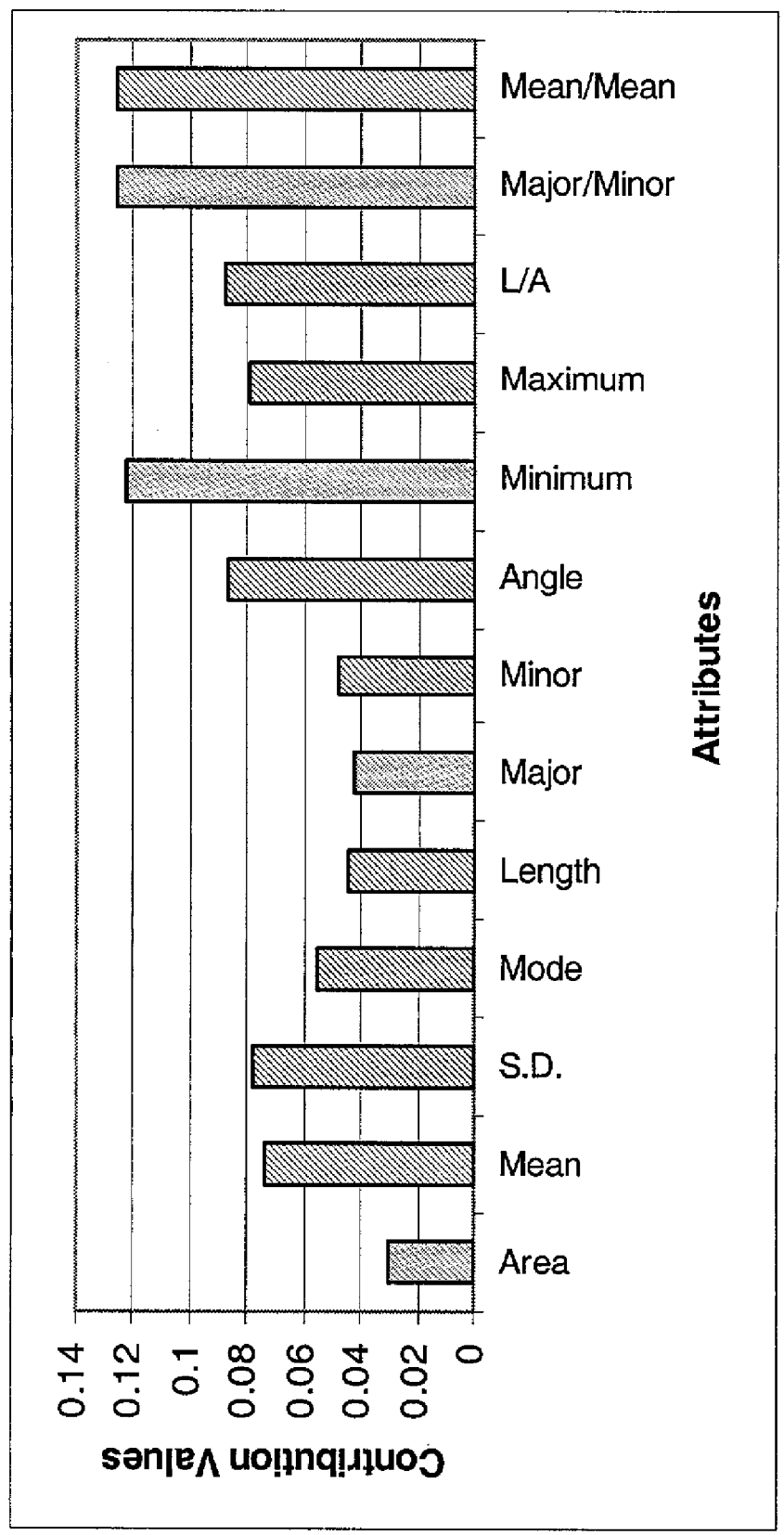
Figure 113:
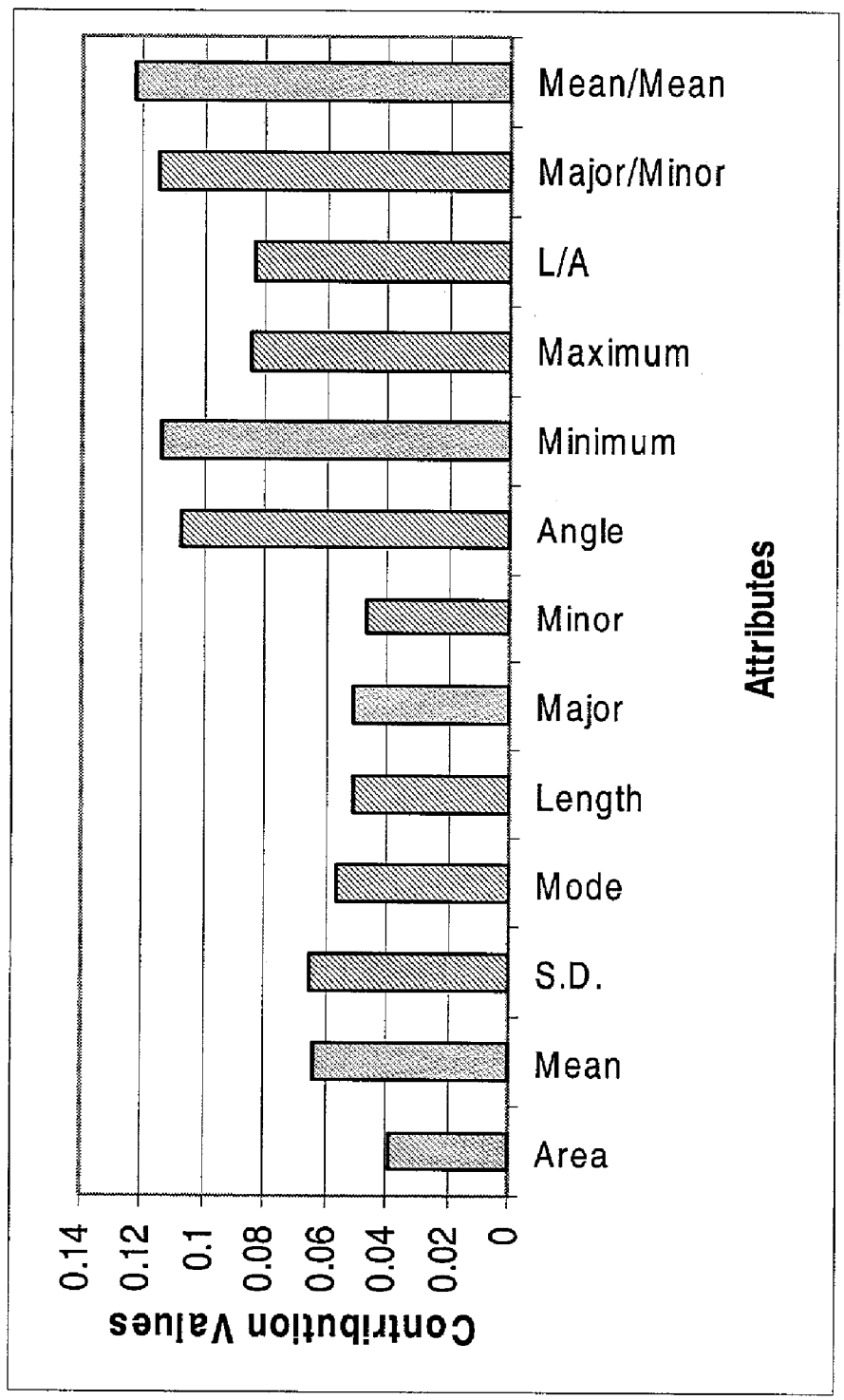

Table 49 shows the Initial Parameters Used in Designing a Preliminary Neural Network for Classification of Misalignments;

FIG. 50 is a photograph showing Inverted Image of Misalignments;

FIG. 51 is a photograph showing Dilated Image of Misalignments;

FIG. 52 is a photograph showing Background Subtracted Image of Misalignments;

FIG. 53 is a photograph showing Thresholded Image of Misalignments;

FIG. 54 is a photograph showing Segmented Image of Misalignments;

FIG. 55 shows the Analysis Results of an Image Depicting Misalignments;

Figure 56:
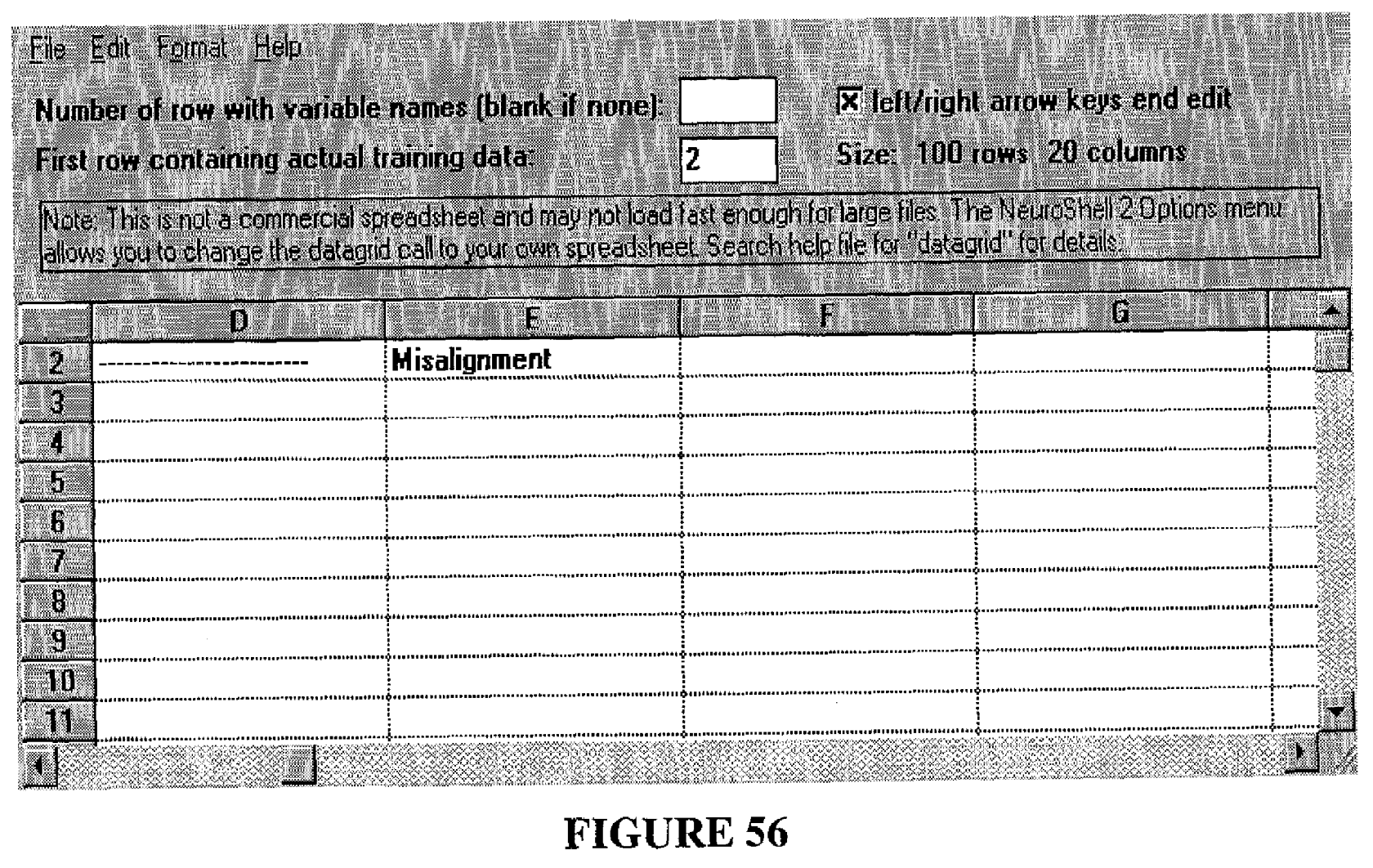

FIG. 56 shows the Classification Results of a Case example on Misalignments;

FIG. 57 is a photograph showing Segmented Image of Deposits;

FIG. 58 is a photograph showing Segmented image of Misalignments;

FIG. 59 is a photograph showing Segmented Image of Cross-sectional Reductions;

FIG. 60 is a photograph showing Segmented Image of Cracks;

FIG. 61 is a photograph showing Segmented Image of Infiltration;

Figures 62A, 62B:
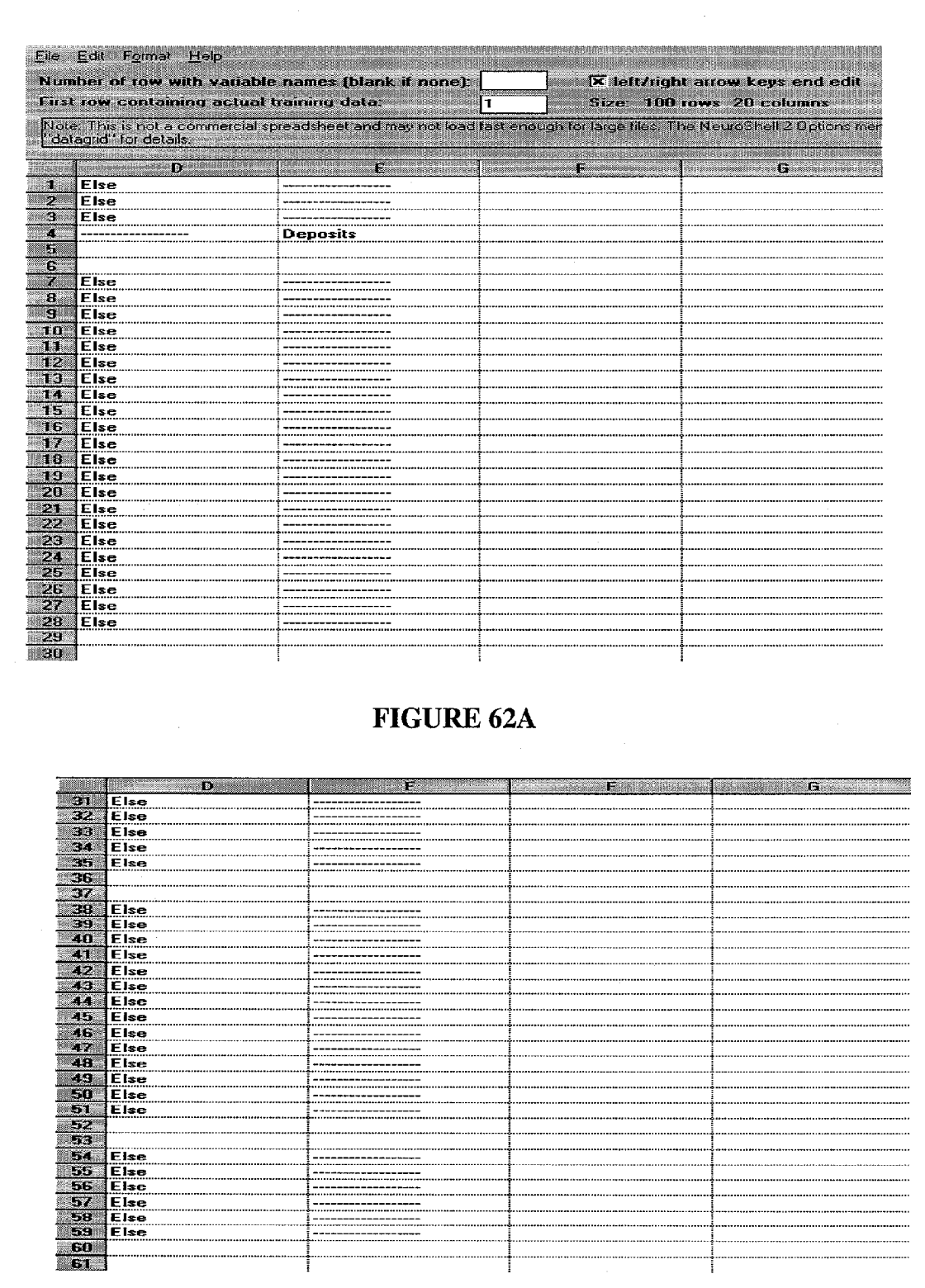

FIG. 62A and FIG. 62B show the Output Results of a Case Example on Deposits Utilizing DepositNet 1 and the Solution Strategy Module;

Figures 63A, 63B:
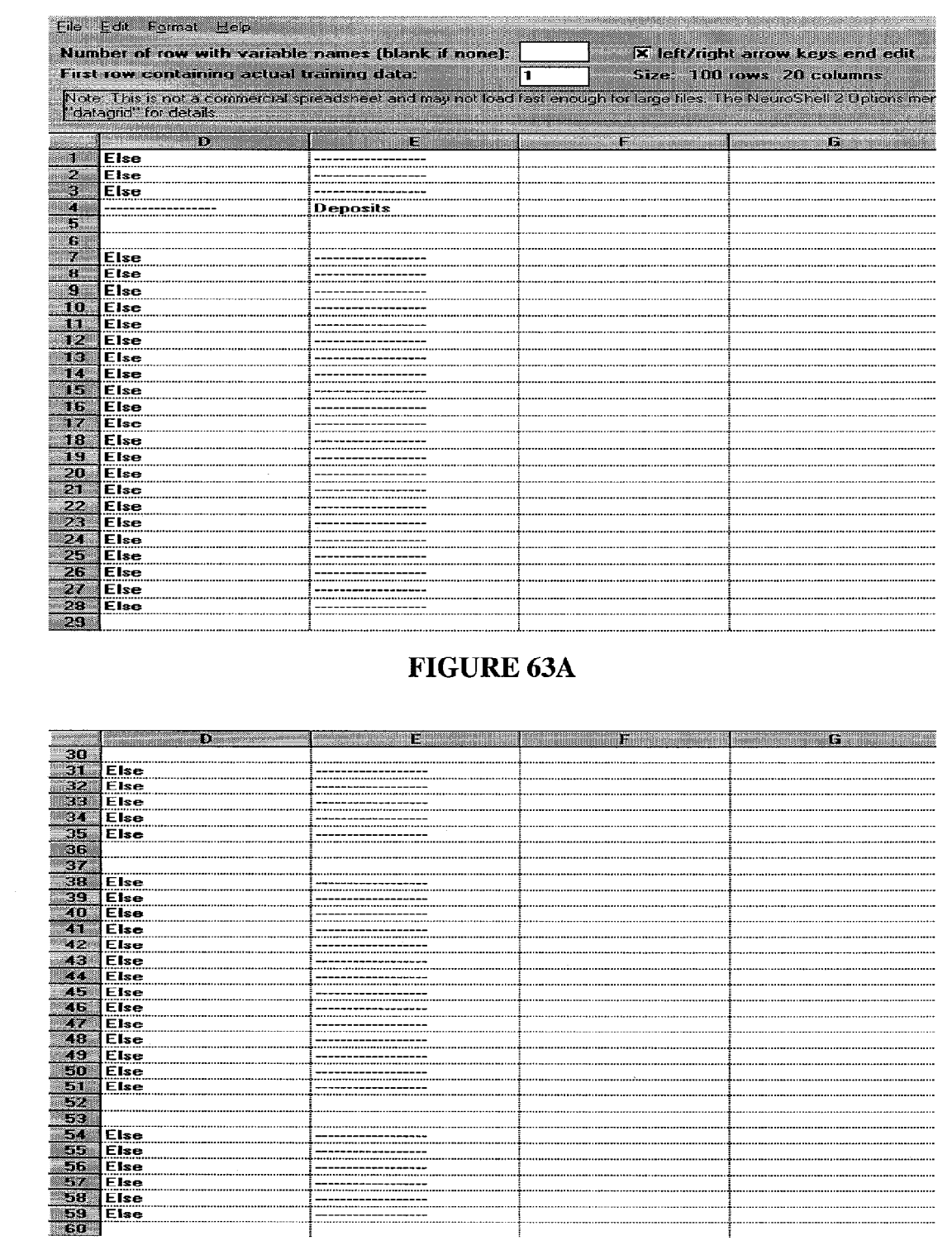

FIG. 63A and FIG. 63B show the Output Results of a Case Example on Deposits Utilizing DepositNet 2 and the Solution Strategy Module;

Figures 64A, 64B:
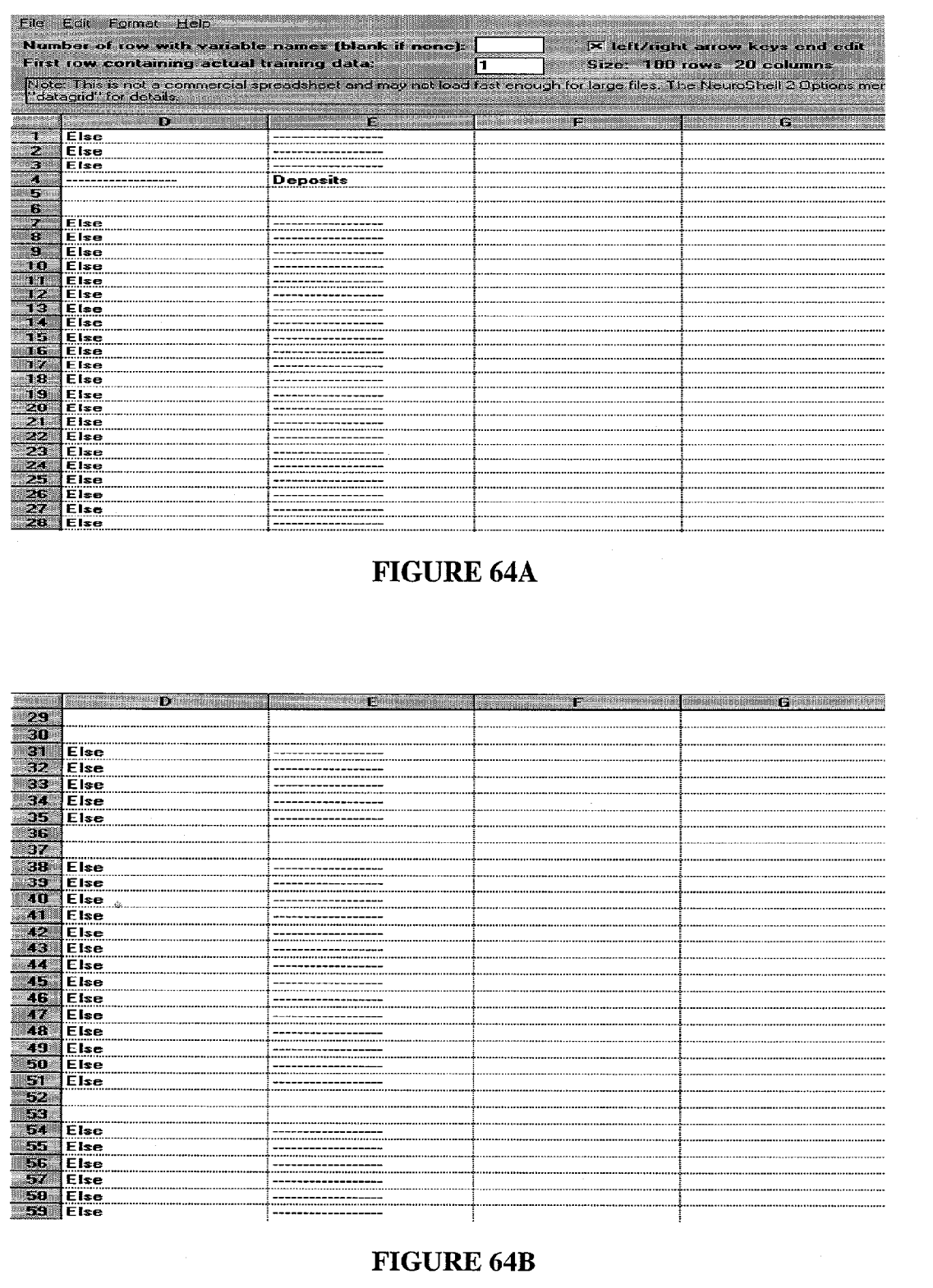

FIG. 64A and FIG. 64B show the Output Results of a Case Example on Deposits Utilizing DepositNet 3 and the Solution Strategy Module;

FIG. 65A and FIG. 65B show the Comparison of Output Results of DepositNet 1–3 Utilizing the Multiple Classifier Module;

Figure 66:
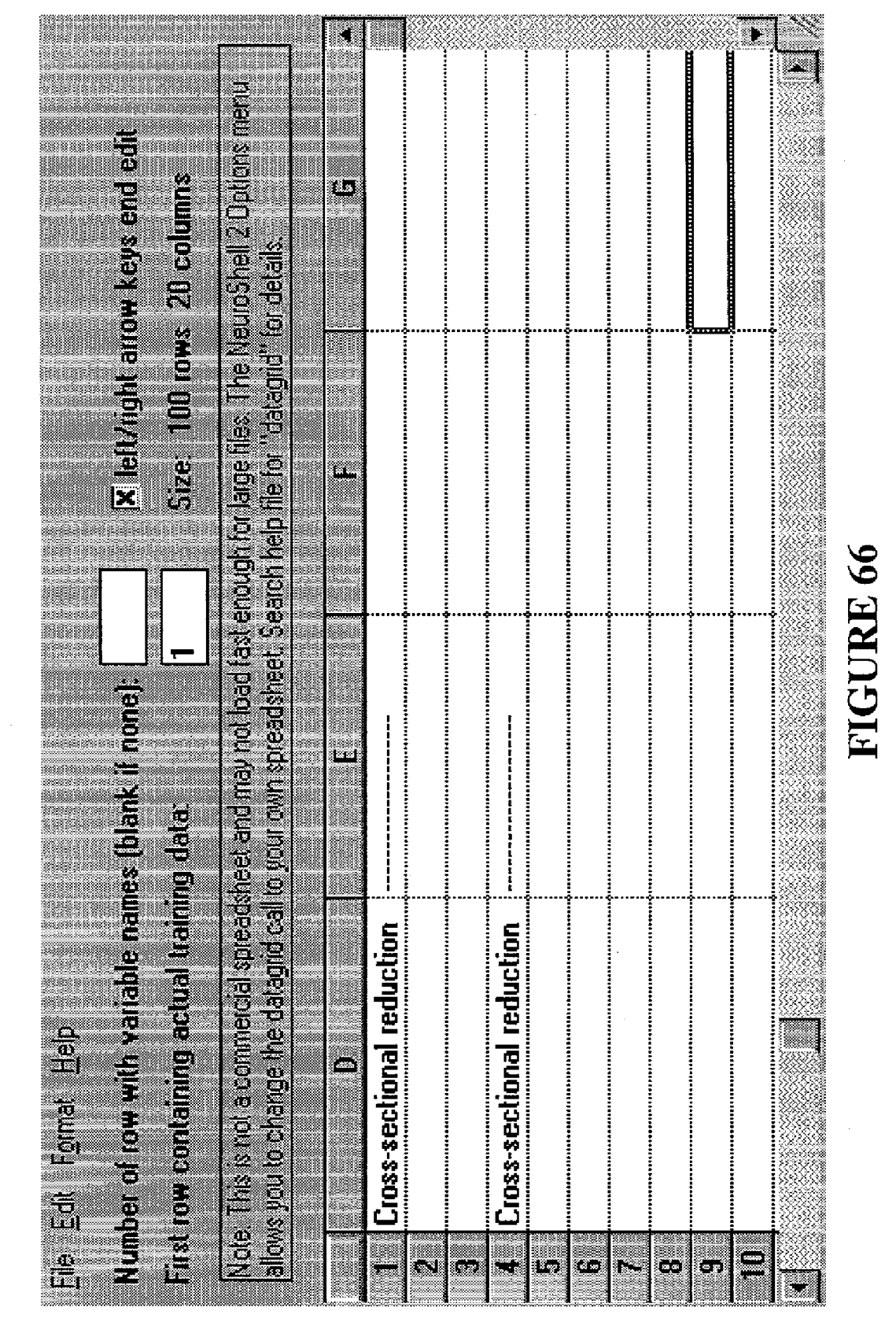

FIG. 66 shows the Output Results of a Case Example on Cross-sectional Reductions Utilizing CrossNet 1 and the Solution Strategy;

Figure 67:
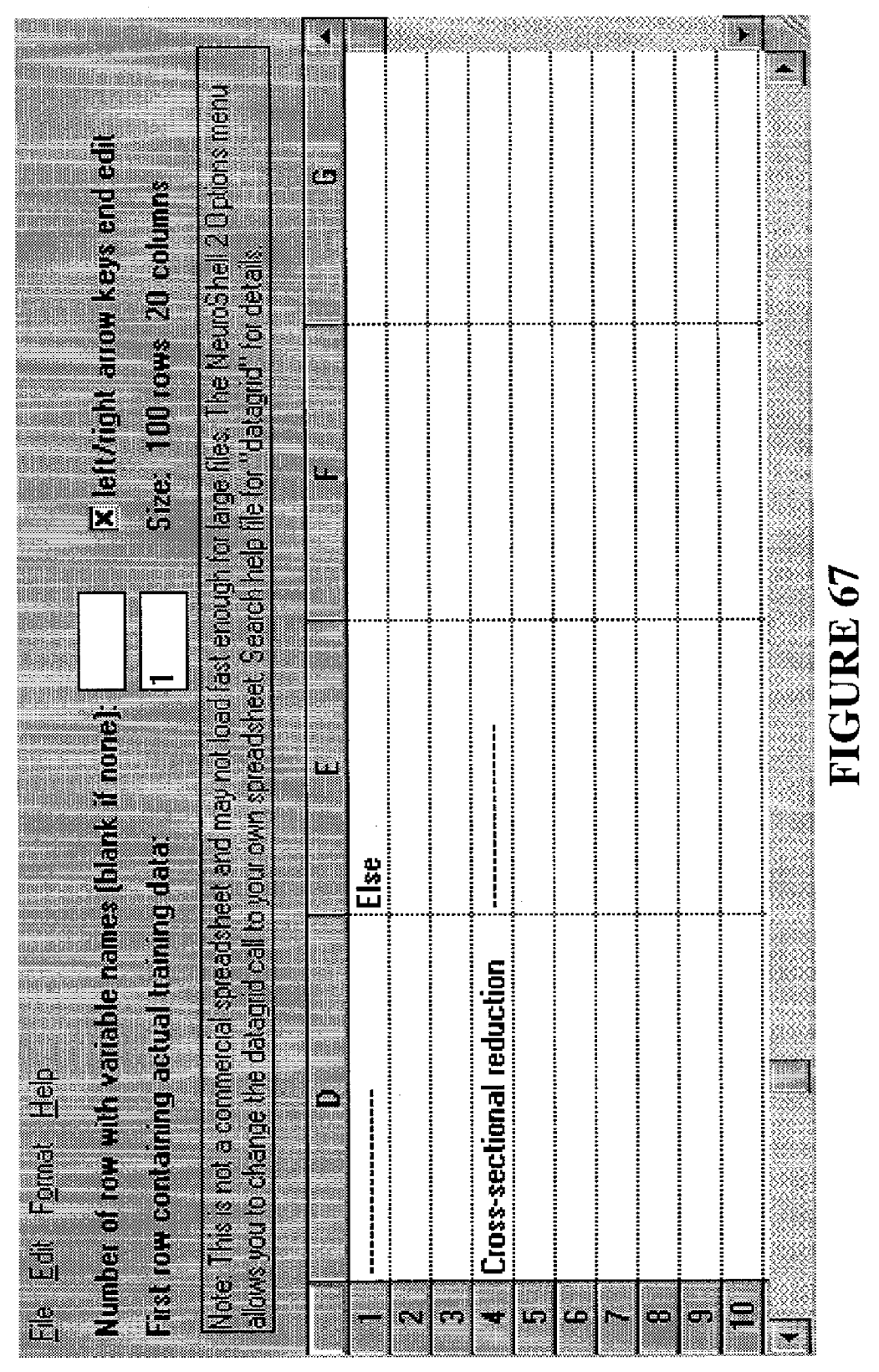

FIG. 67 shows the Output Results of a Case Example on Cross-sectional Reductions Utilizing CrossNet 2 and the Solution Strategy;

Figure 68:
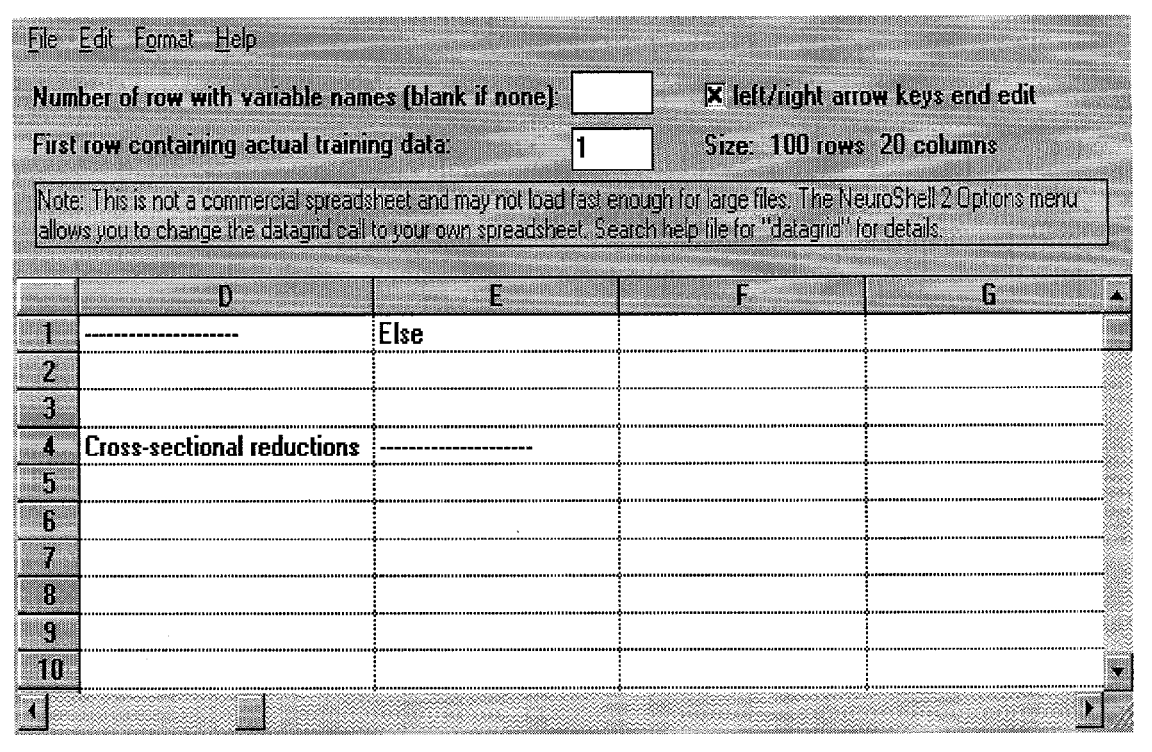

FIG. 68 shows the Output Results of a Case Example on Cross-sectional Reductions Utilizing CrossNet 3 and the Solution Strategy;

FIG. 69 shows the Comparison of Output Results of CrossNet 1–3 Utilizing the Multiple Classifier Module;

FIG. 70 shows the Output Results of a Case Example on Misalignments Utilizing MisalignmentNet 1 and the Solution Strategy Module;

FIG. 71 shows the Output Results of a Case Example on Misalignments Utilizing MisalignmentNet 2 and the Solution Strategy Module;

FIG. 72 shows the Output Results of a Case Example on Misalignments Utilizing MisalignmentNet 3 and the Solution Strategy Module;

FIG. 73 shows the Comparison of Output Results of MisalignmentNet 1–3 Utilizing the Multiple Classifier Module;

FIG. 74 is a photograph showing Segmented Image of Cracks;

FIG. 75 is a photograph showing Segmented Image of Cross-sectional Reductions;

FIG. 76 is a photograph showing Segmented Image of Misalignments;

FIG. 77 is a photograph showing Segmented image of Deposits;

FIG. 78 is a photograph showing Segmented Image of Infiltration;

FIG. 79A and FIG. 79B show the Output Results of a Case Example on Infiltration Utilizing InfiltrationNet 1 and the Solution Strategy;

FIG. 80A and FIG. 80B show the Output Results of a Case Example on Infiltration Utilizing InfiltrationNet 2 and the Solution Strategy;

FIG. 81A and FIG. 81B show the Output Results of a Case Example on Infiltration Utilizing InfiltrationNet 3 and the Solution Strategy;

FIG. 82A and FIG. 82B show the Comparison of Output Results of InfiltrationNet 1–3 Utilizing the Multiple Classifier Module;

FIG. 83 is a photograph showing Segmented Image of Cracks;

FIG. 84 is a photograph showing Segmented Image of Cross-sectional Reductions;

FIG. 85 is a photograph showing Segmented Image of Misalignments;

FIG. 86 is a photograph showing Segmented Image of Deposits;

FIG. 87 is a photograph showing Segmented Image of Infiltration;

Figures 88A, 88B:
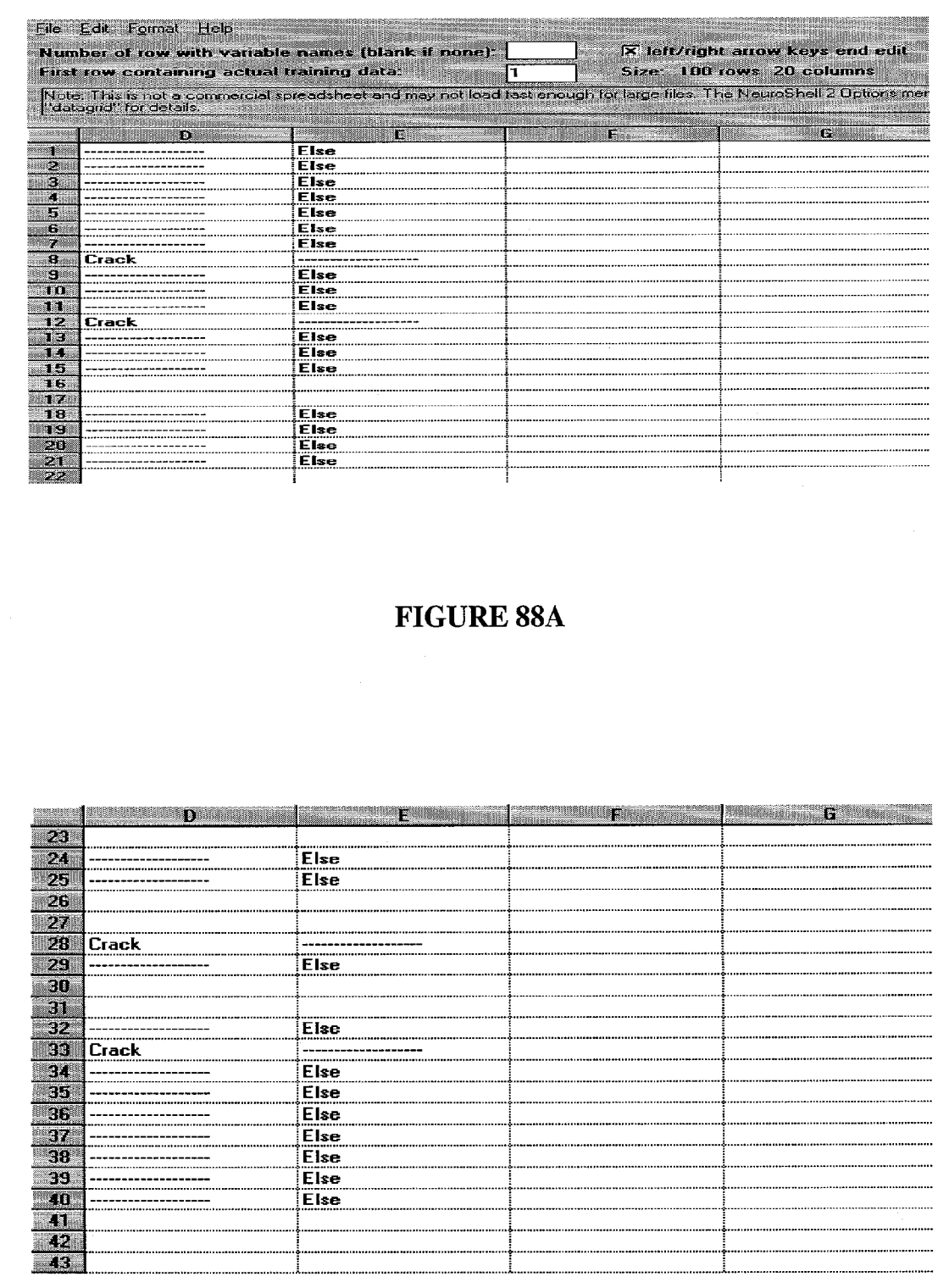

FIG. 88A and FIG. 88B show the Output Results of a Case Example on Cracks Utilizing CrackNet 1 and the Solution Strategy;

FIG. 89A and FIG. 89B show the Output Results of a Case Example on Cracks Utilizing CrackNet 2 and the Solution Strategy;

FIG. 90A and FIG. 90B show the Output Results of a Case Example on Cracks Utilizing CrackNet 3 and the Solution Strategy;

FIG. 91A and FIG. 91B show the Comparison of Output Results of CrackNet 1–3 Utilizing the Multiple Classifier Module;

FIG. 92 shows the Developed Rehabilitation system;

FIG. 93 shows the Products Table;

FIG. 94 shows the Entity Relationship Diagram;

FIG. 95 shows the Schema of the Developed Database;

FIG. 96 shows the Database Execution Form;

Figure 97:
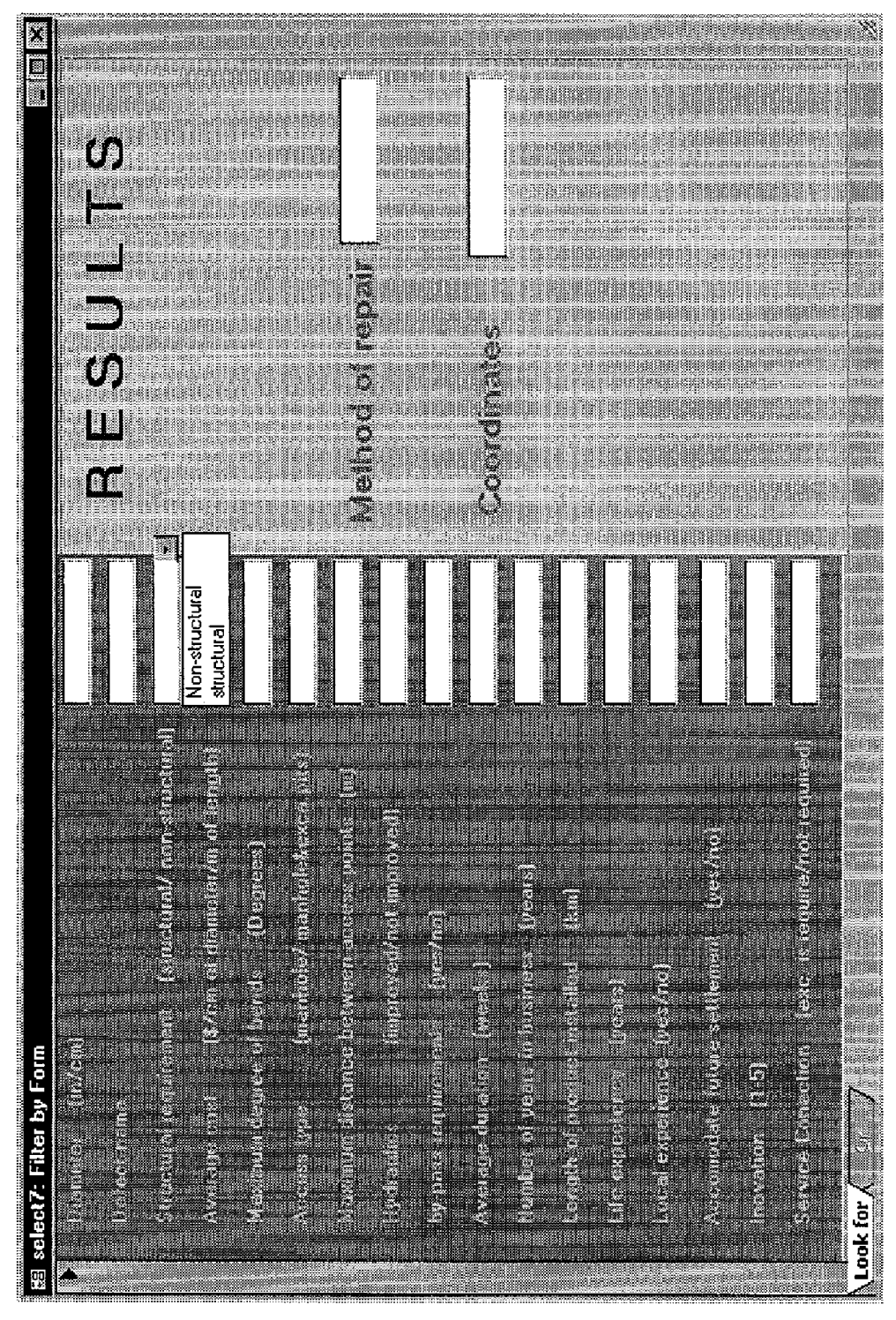

FIG. 97 shows the Data Entry and Retrieval Form;

Figure 98:
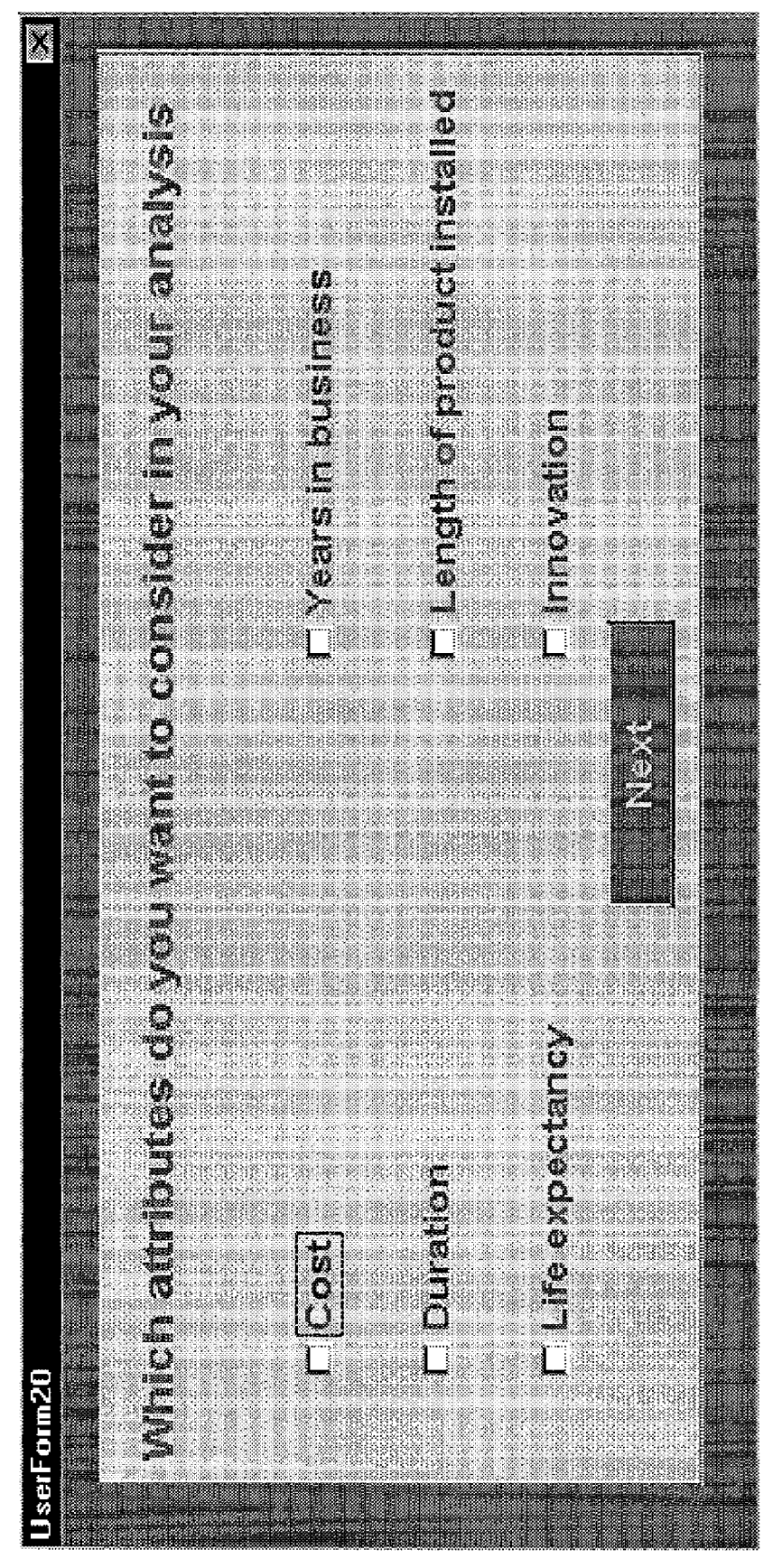

FIG. 98 shows the Available Attributes to Users;

FIG. 99 shows the Sample Dialog Screen;

FIG. 100 shows the Plotting of Utility Functions;

FIG. 101 shows the Selection of Utility Functions;

FIG. 102 shows the Steering the Program to the Required Mode of Weight Calculation;

Figure 103:
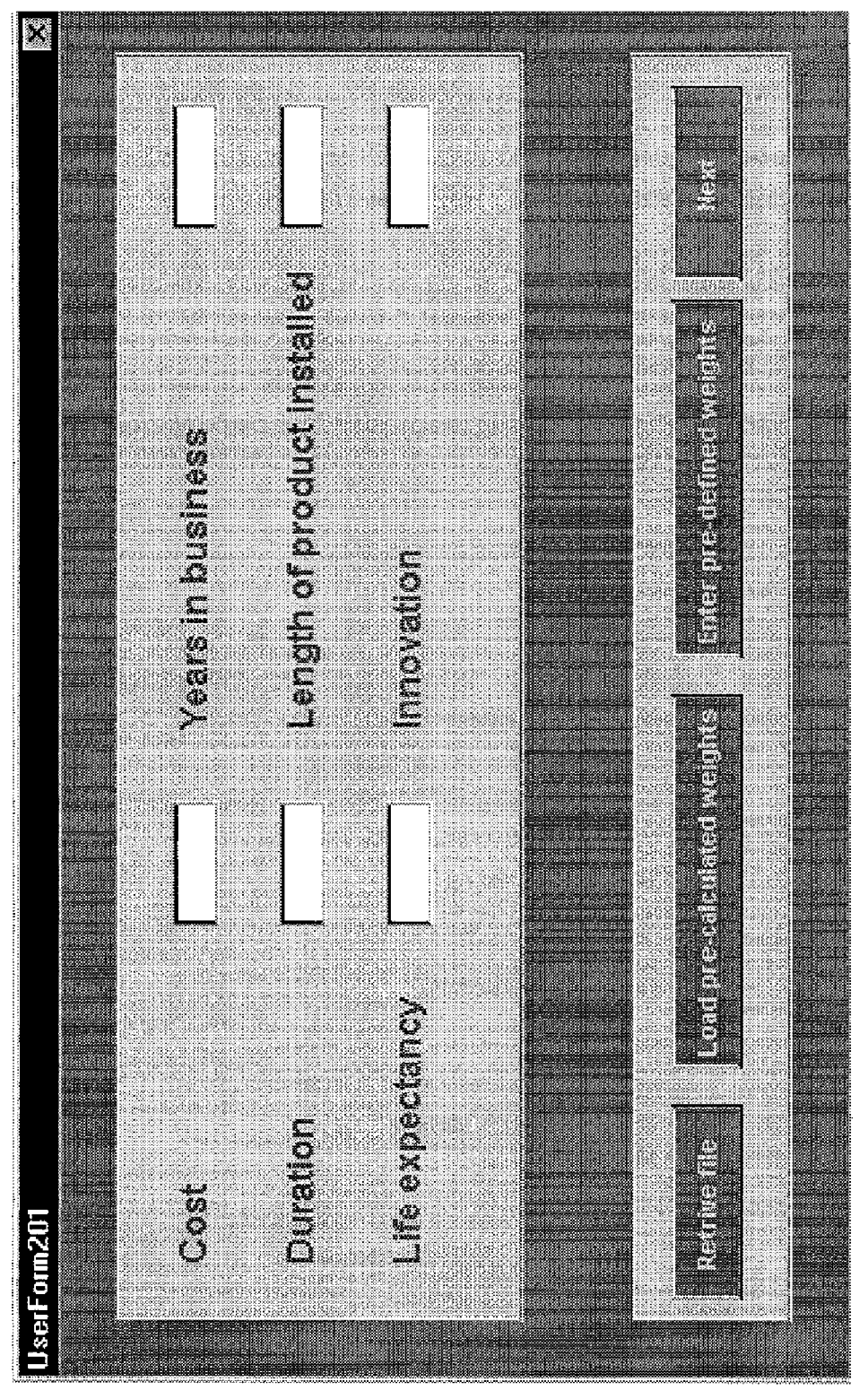

FIG. 103 shows the Feeding a Pre-Calculated Set of Weights;

FIG. 104 shows the Retrieving a Pre-Defined Set of Weights;

Figure 105:
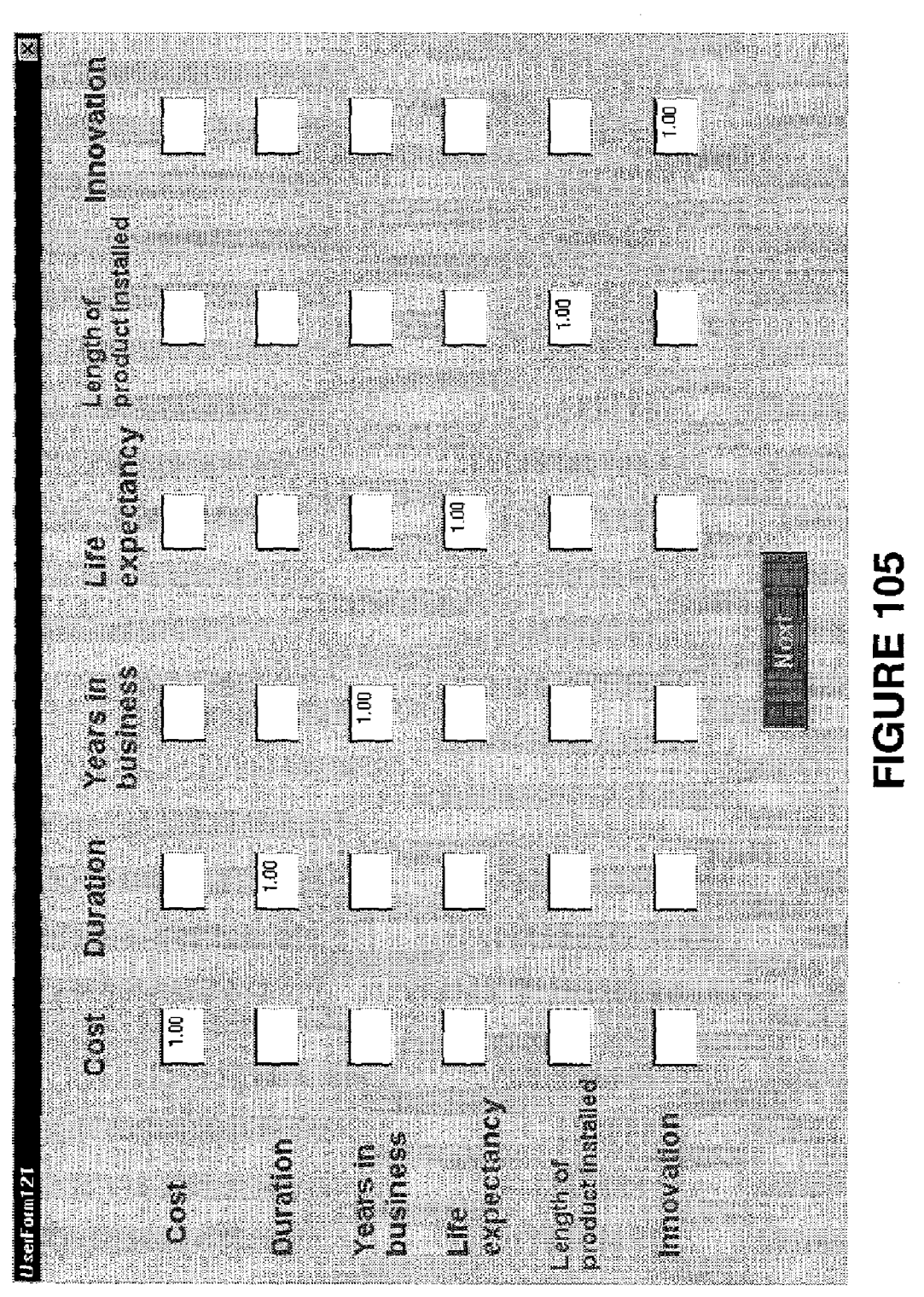

FIG. 105 shows the Relative Importance Screen;

Figure 106:
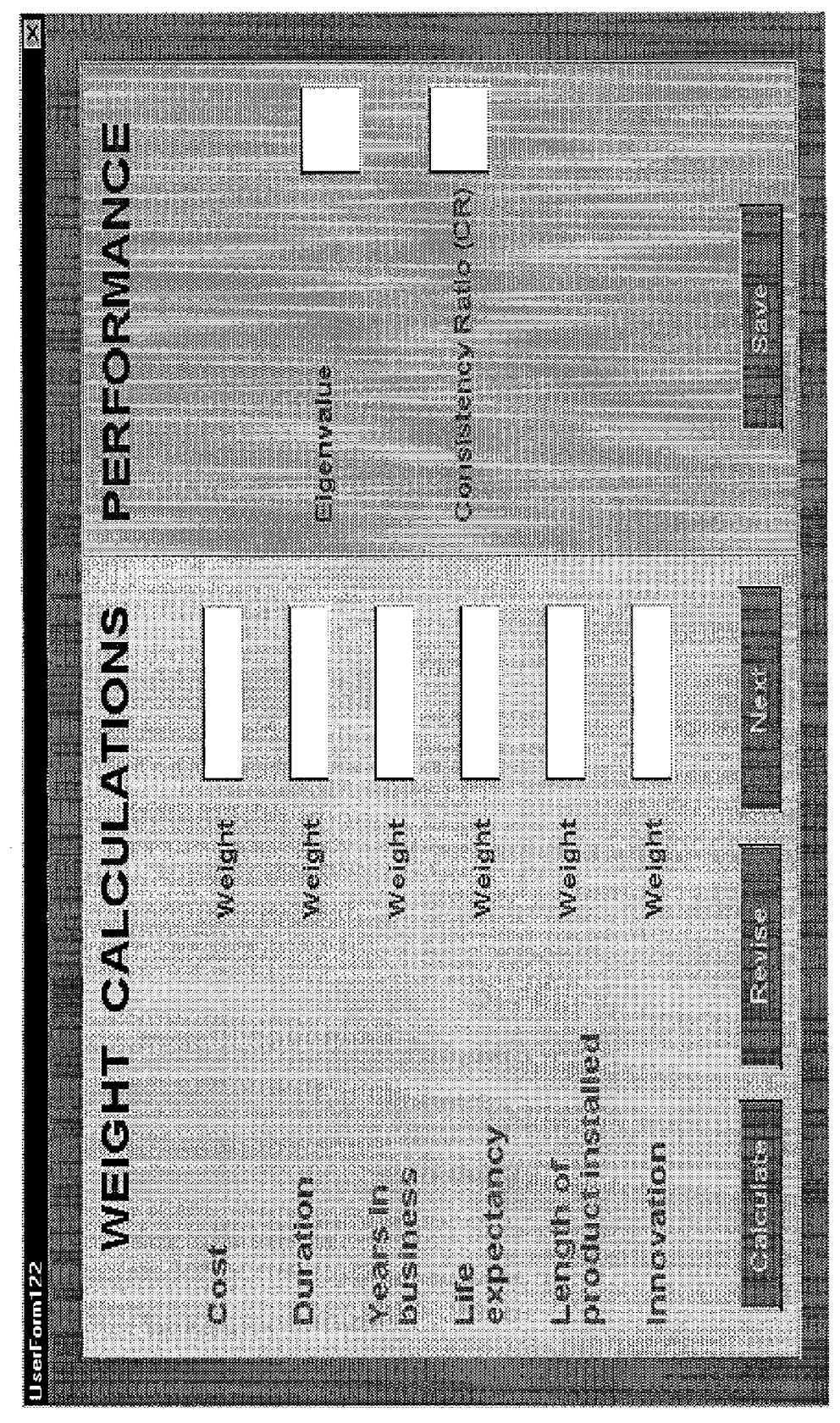

FIG. 106 shows the Weight Calculation Screen;

Figure 107:
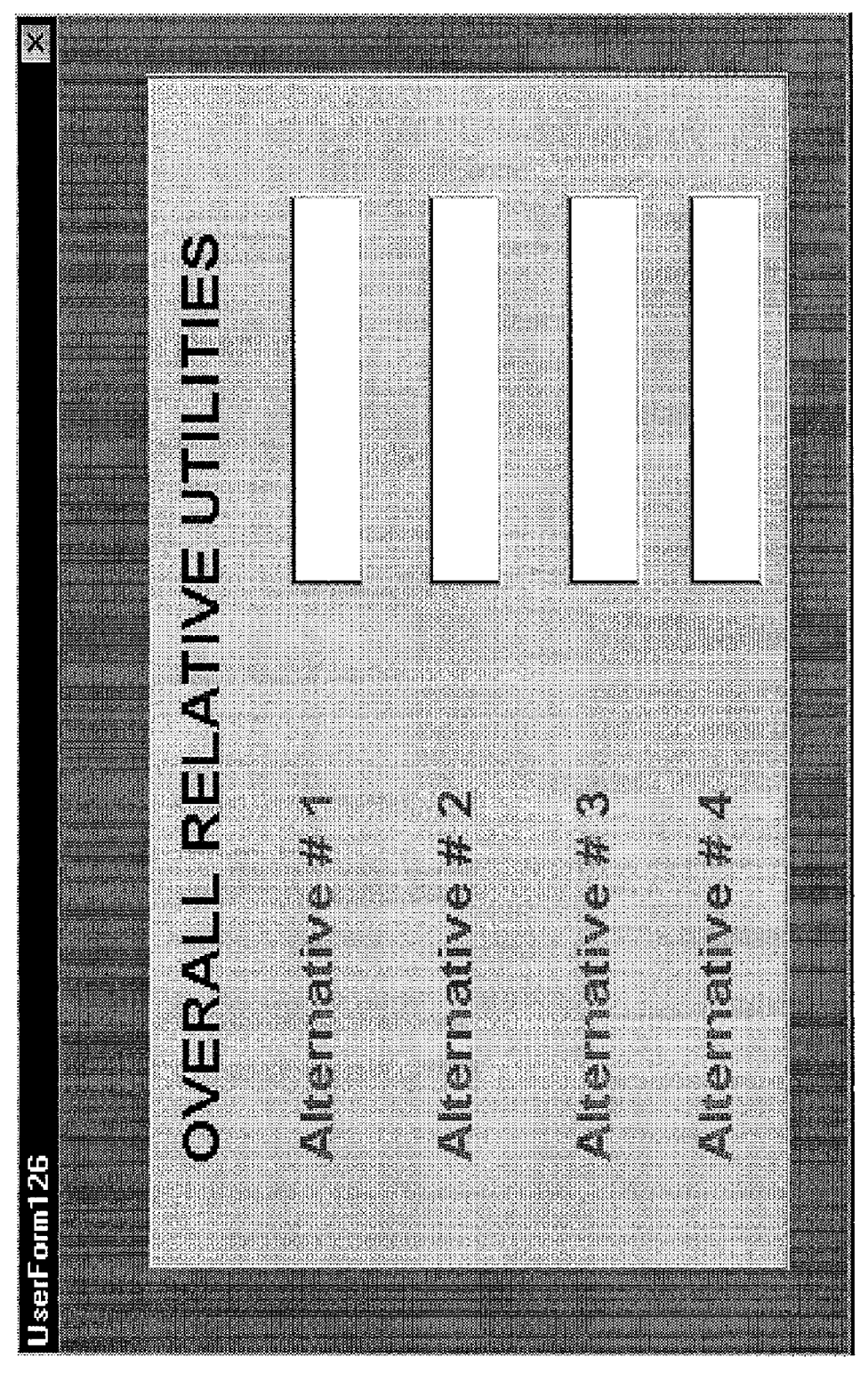

FIG. 107 shows the Overall Utility Values;

FIG. 108 shows the Contribution Values of Attributes Utilized in Designing InfiltrationNet 2;

FIG. 109 shows the Contribution Values of Attributes Utilized in Designing InfiltrationNet 3;

FIG. 110 shows the Contribution Values of Attributes Utilized in Designing DepositNet 2;

FIG. 111 shows the Contribution Values of Attributes Utilized in Designing DepositNet 3;

FIG. 112 shows the Contribution Values of Attributes Utilized in Designing CrossNet 1;

FIG. 113 shows the Contribution Values of Attributes Utilized in Designing CrossNet 2

Figure 114:
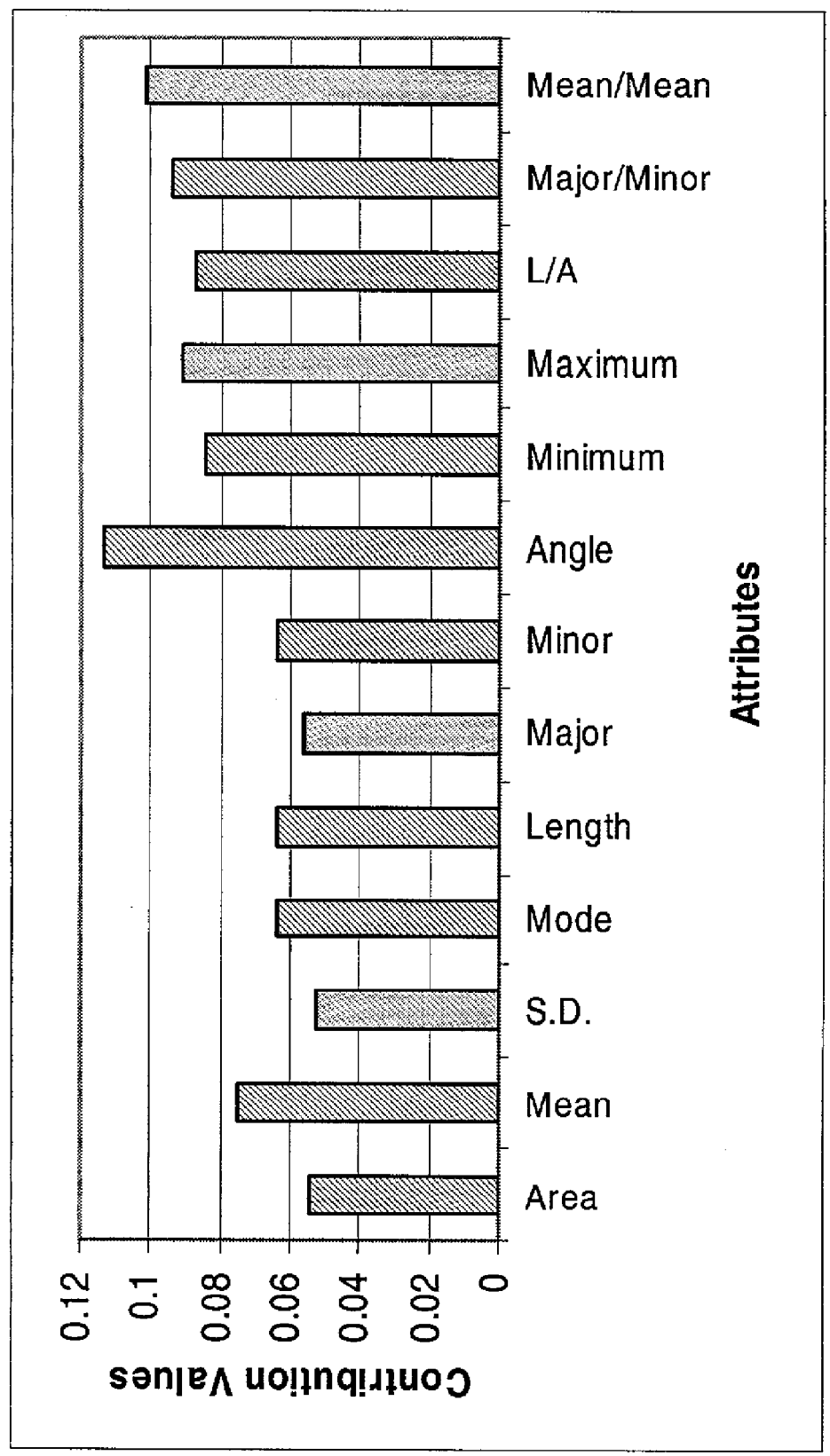
Figure 115:
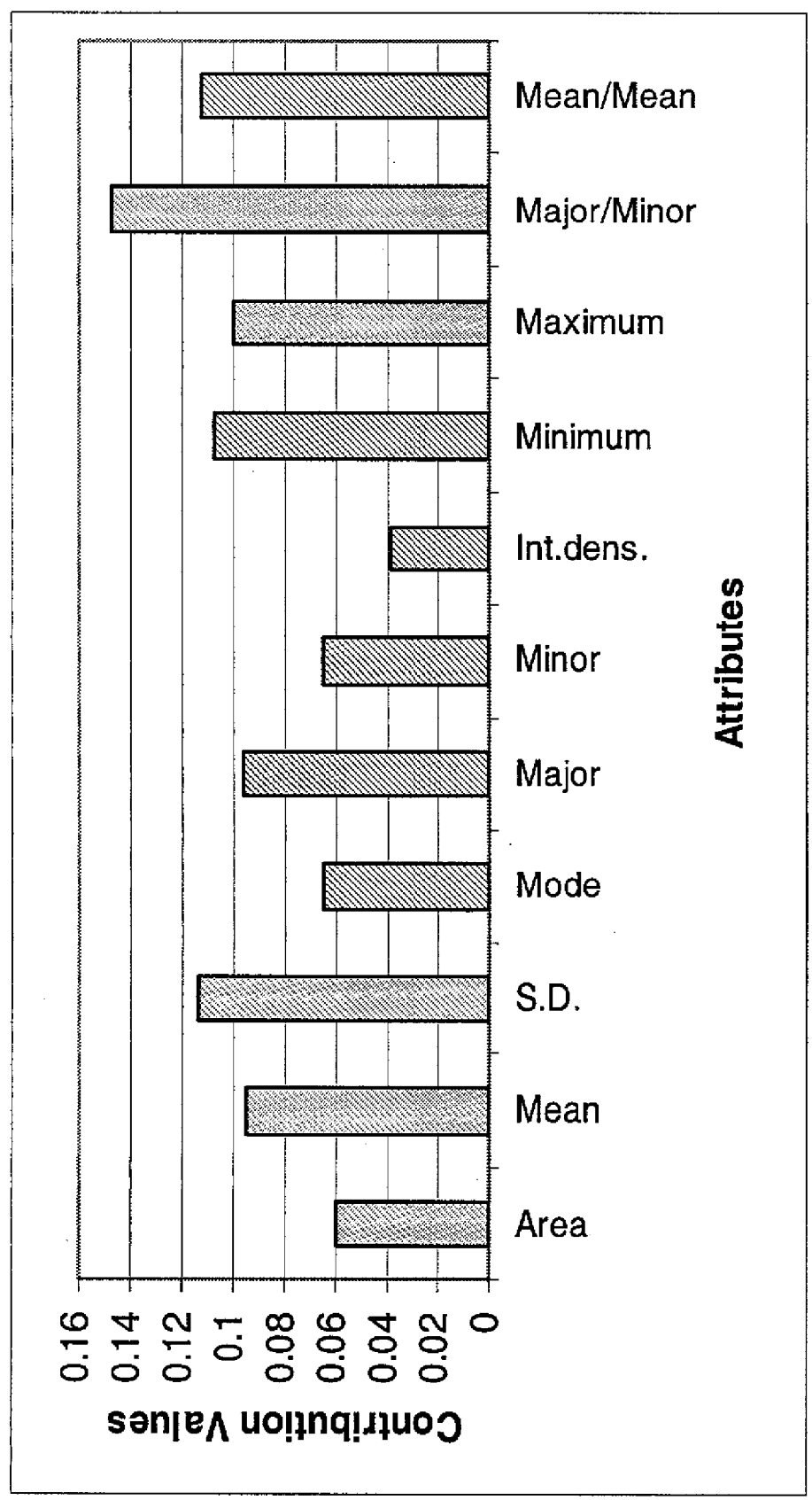
Figure 116:
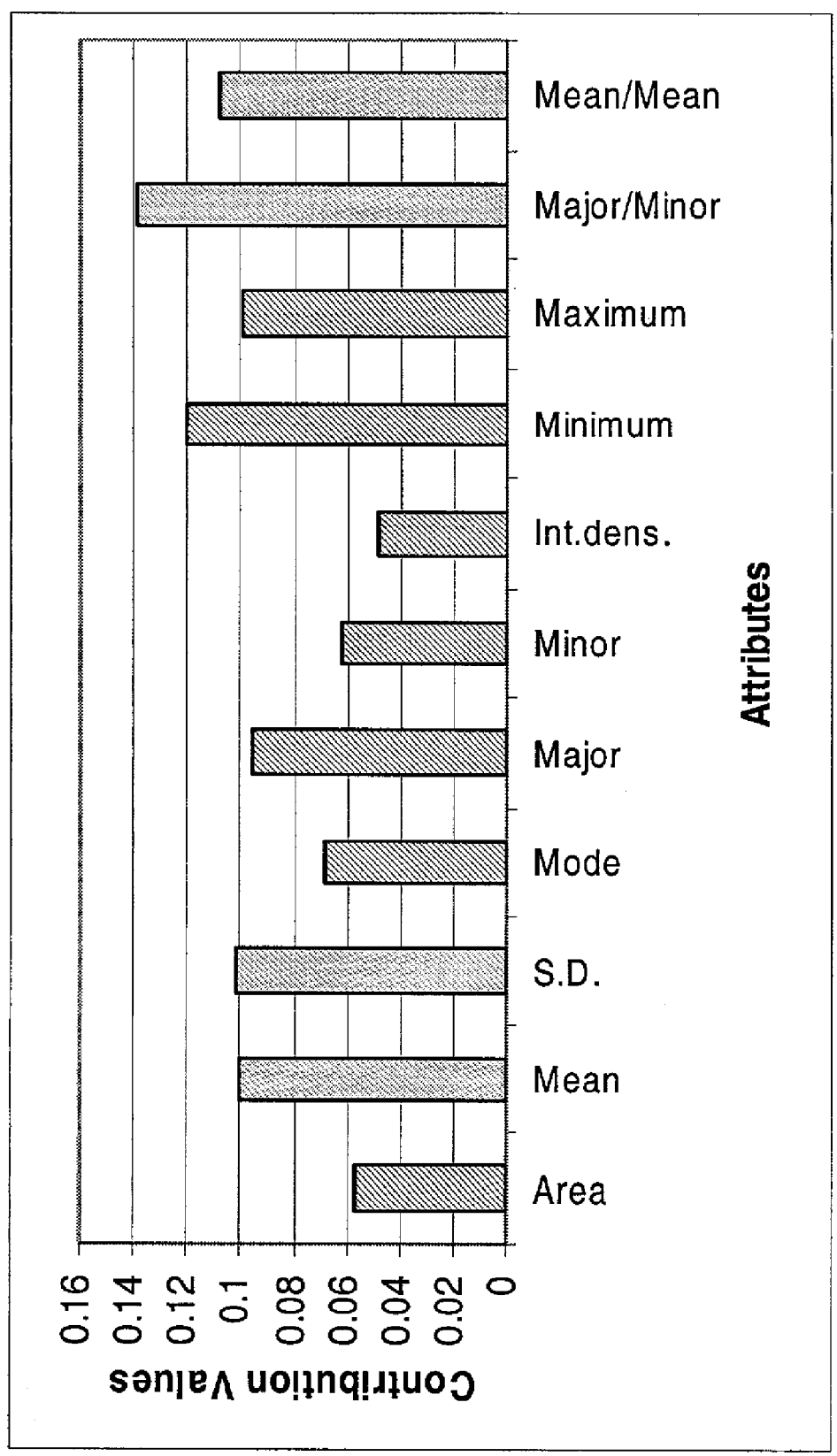
Figure 117:
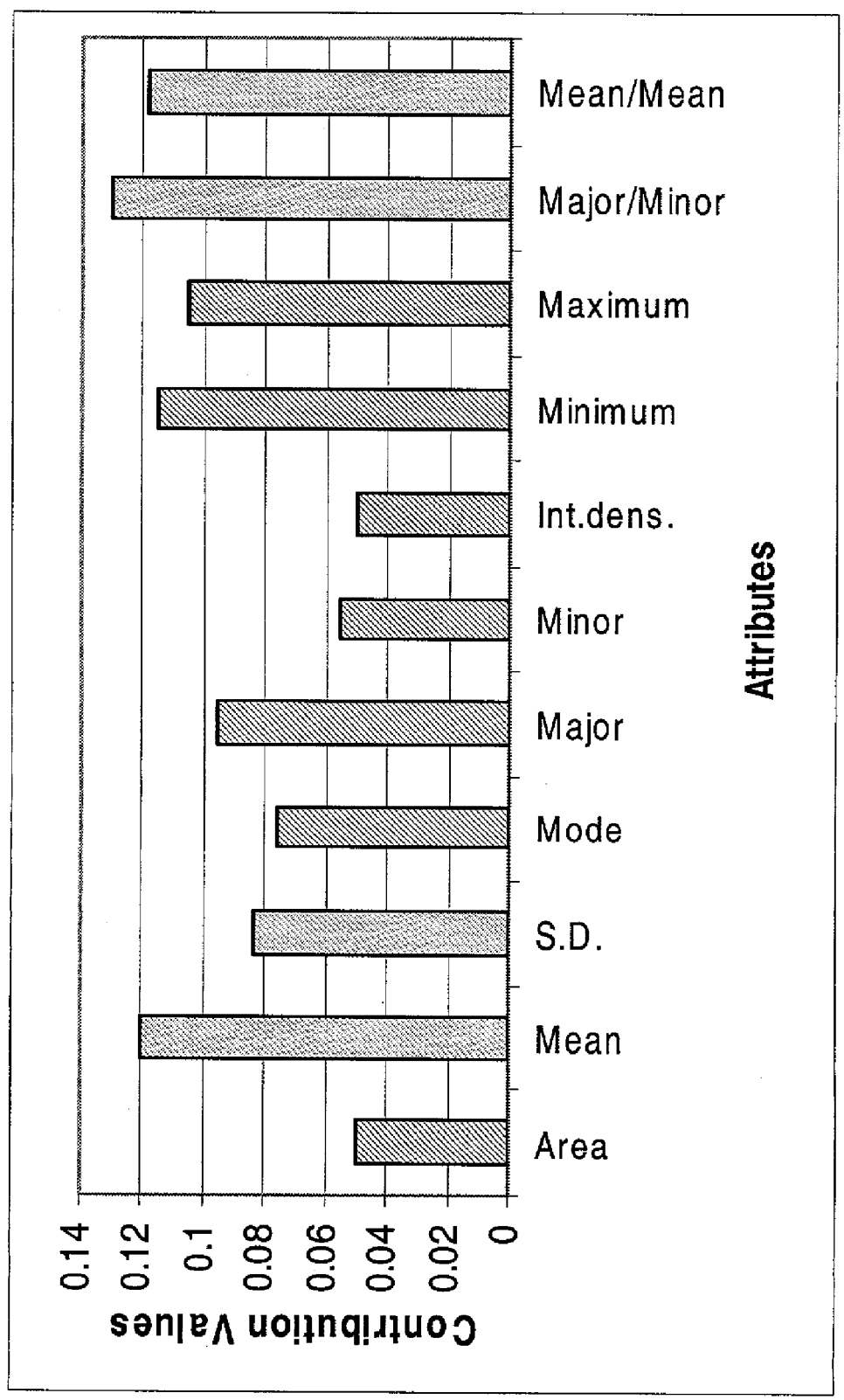
Figure 118:
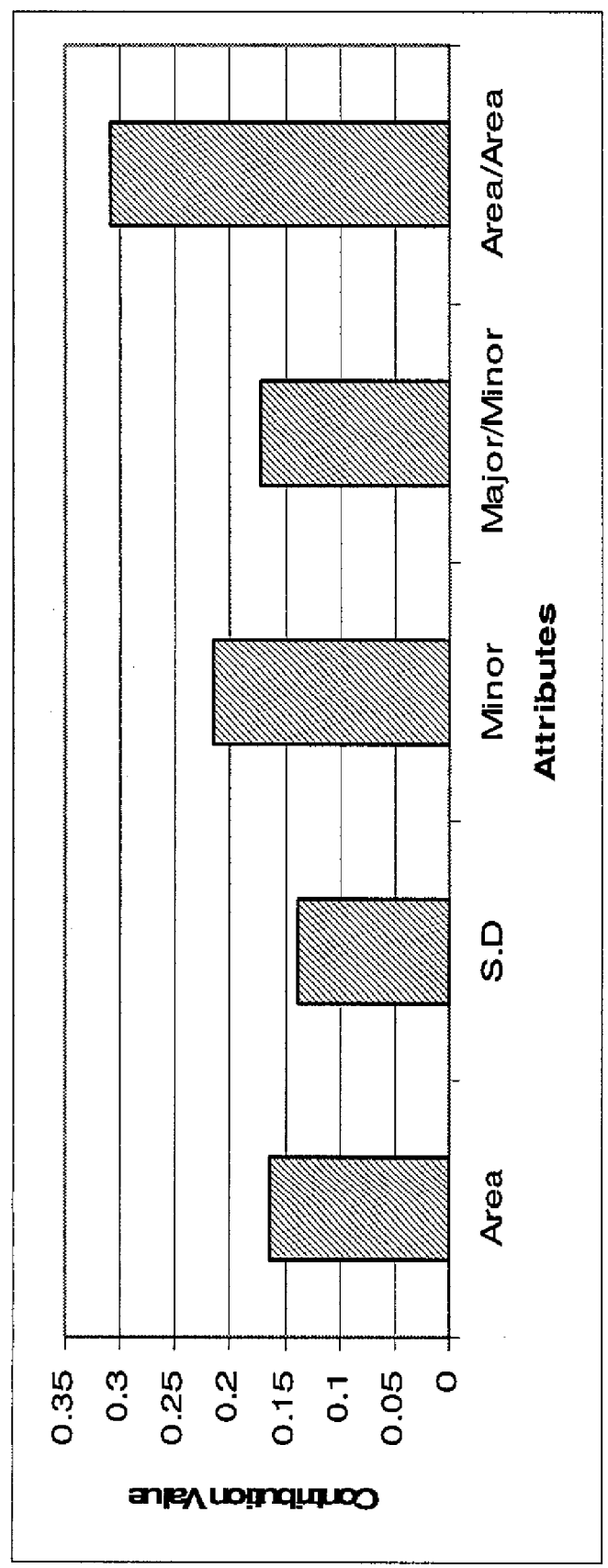
Figure 119:
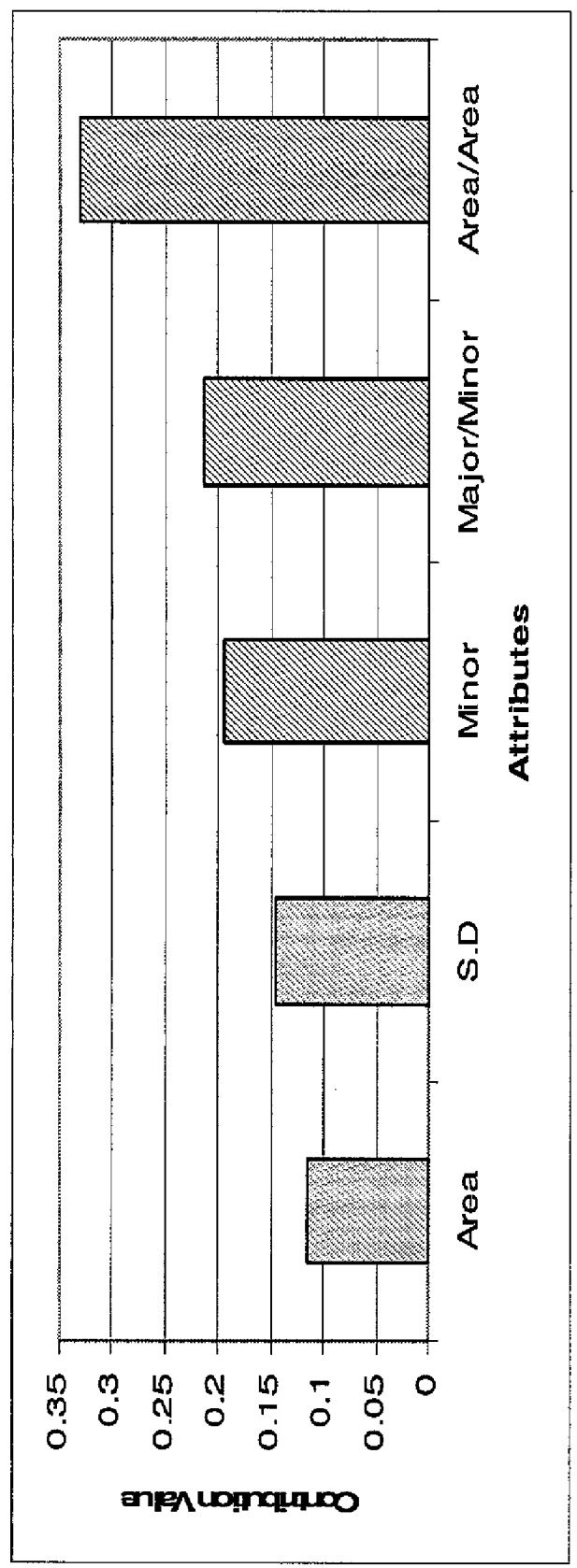
Figure 120:
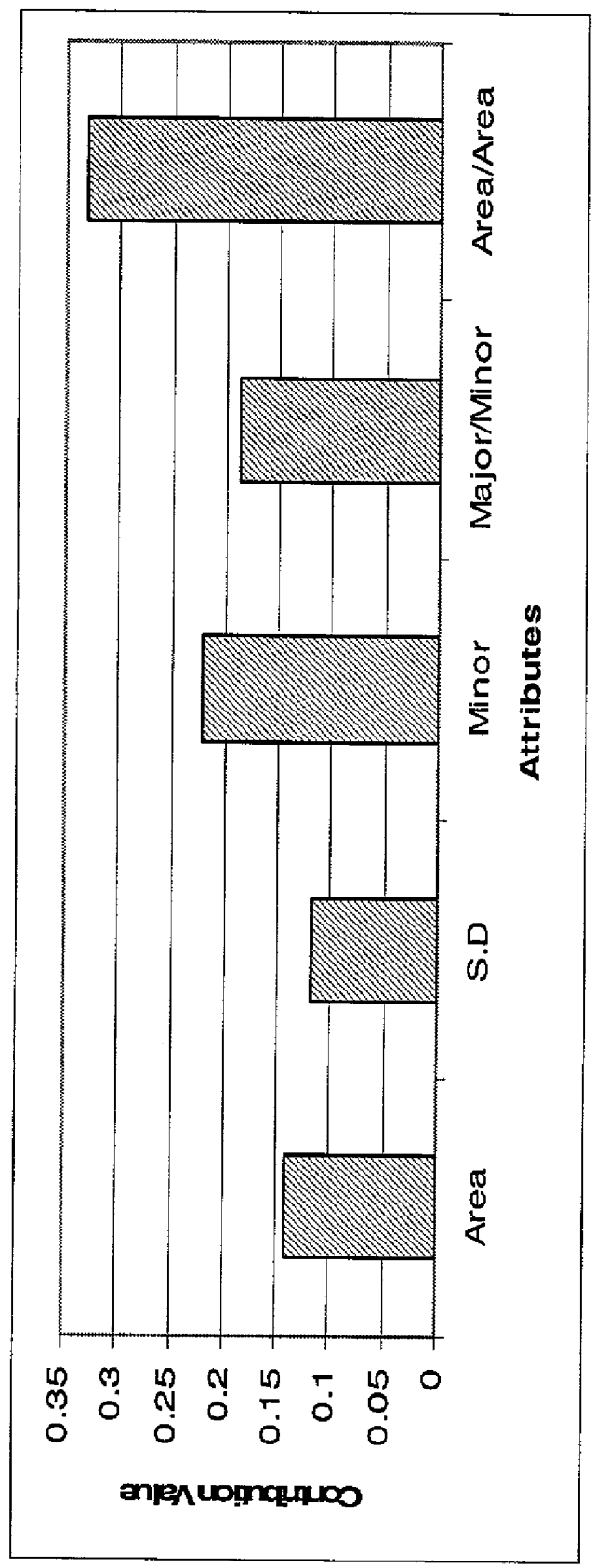

FIG. 114 shows the Contribution Values of Attributes Utilized in Designing CrossNet 2;

FIG. 115 shows the Contribution Values of Attributes Utilized in Designing AlignmentNet 1;

FIG. 116 shows the Contribution Values of Attributes Utilized in Designing AlignmentNet 2;

FIG. 117 shows the Contribution Values of Attributes Utilized in Designing AlignmentNet 3;

FIG. 118 shows the Contribution Values of Attributes Utilized in Designing ModCrossNet 1;

FIG. 119 shows the Contribution Values of Attributes Utilized in Designing ModCrossNet 2; and FIG. 120 shows the Contribution Values of Attributes Utilized in Designing ModCrossNet 3.

DETAILED DESCRIPTION OF THE PREFERRED EMBODIMENT

Types of Defects in Sewer Pipes

Knowing prior information about types, nature and frequency of occurrence of defects could probably be considered a corner stone in developing a system that detects them automatically. It helps to identify the characteristic features of defects, which will be considered as the basic criteria in classifying them automatically. A survey by the regional municipality of Hamilton, Ontario, Canada covered approximately 25% of the total sewer network in the region, which is approximately 5659 sections. Each section is about 80 m. The age of pipes ranged between 2 and 100 years, and their materials are concrete and clay. The burial depth of pipes ranged between 2 and 10 m and their diameter ranged from 250 to 1950 mm. The results of the survey are summarized in Table A. As can be noticed from this table, the most common defects are dirt deposits (23.8%) and offset joints (13.7%). Longitudinal cracks, water infiltration at the joint, sign of infiltration at the joint are also reported to have percentage occurrence of more than 5%, which are considered to be high compared to other types of defects. It should be noted that due to the fact that neither the flow nor structural soundness of pipes are adversely affected by the presence of right or left lateral deviations, they could be considered non-serious problems. It should also be noted that having a water level over 25% of pipe diameter was not considered as an independent type of defect due to the fact that it could be attributed to other defects, such as opposite slopes.

Figure 1:
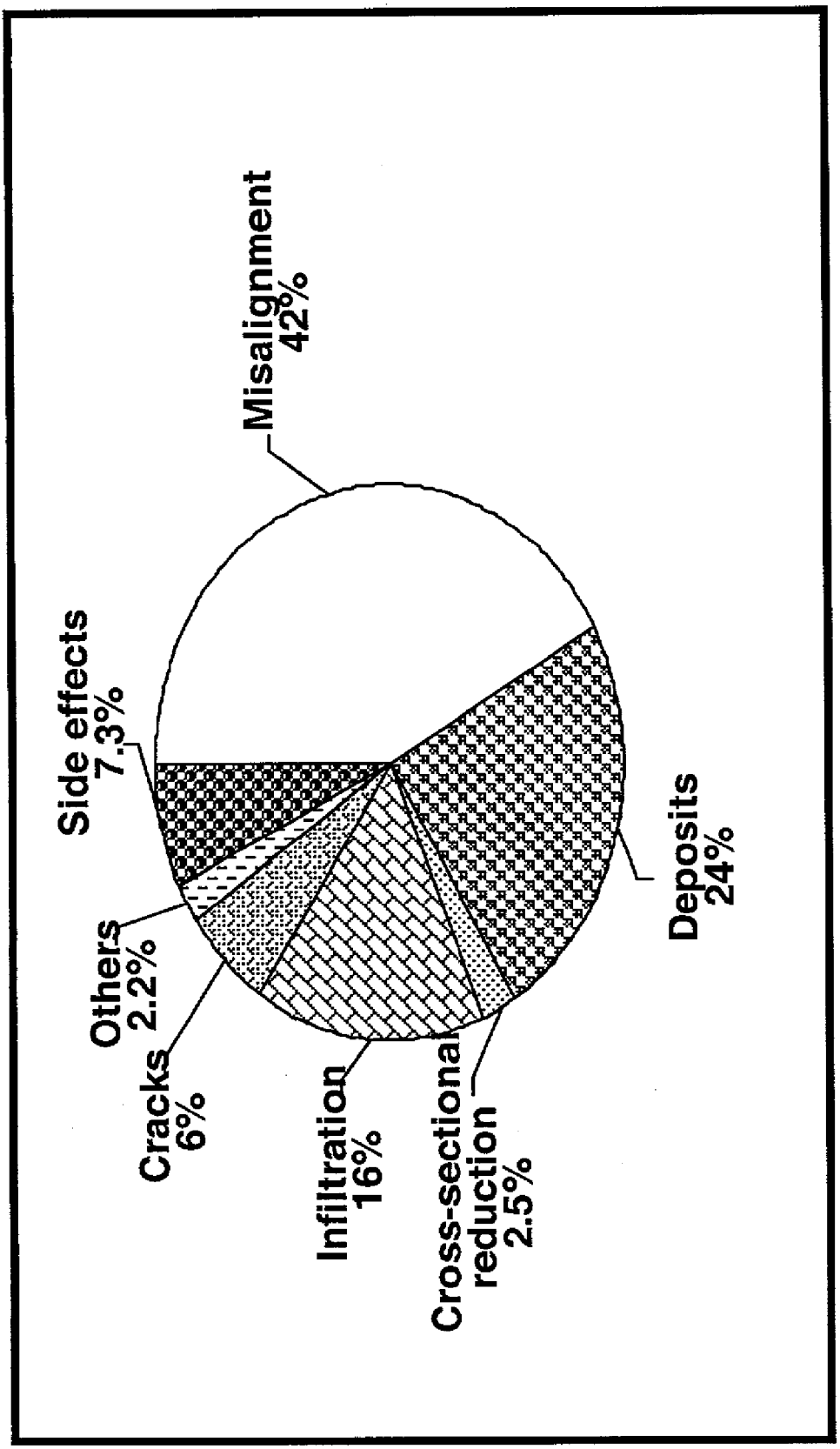
FIG. 1 shows the Categories of Defects in Sewer Pipes.

Depending on the nature, shape and common features of defects, they could be grouped into major categories as shown in FIG. 1. In this grouping scheme, the various defects were grouped into seven different categories. These categories are misalignment, roots, deposits, infiltration, cracks, side effects and others.

TABLE A

Types of Defects in Sewer Pipes

| Defect type | Nb of sections | % of existence |
| --- | --- | --- |
| Offset joint over 3 cm | 523 | 13.670 |
| Open joint over 5 cm | 1 | 0.026 |
| Broken joints | 12 | 0.314 |
| Opposite slopes | 13 | 0.340 |
| Visible soils | 25 | 0.653 |
| Visible armature along the pipe | 2 | 0.052 |
| Visible armature at joint | 3 | 0.078 |
| Broken pipes | 16 | 0.418 |
| Sagging pipes | 5 | 0.131 |
| Circular cracks | 10 | 0.261 |
| Longitudinal cracks | 218 | 5.698 |
| Multiple cracks | 60 | 1.568 |
| Water infiltration | 25 | 0.653 |
| Water infiltration at the joint | 221 | 5.776 |
| Sign of infiltration | 15 | 0.392 |
| Sign of infiltration at the joint | 311 | 8.129 |
| Right lateral deviation | 487 | 12.729 |
| Left lateral deviation | 543 | 14.192 |
| Visible rubber gasket at the joint | 15 | 0.392 |
| Grease accumulations | 9 | 0.235 |
| Light roots | 38 | 0.993 |
| Medium roots | 31 | 0.810 |
| Heavy roots | 9 | 0.235 |
| Mineral accumulations | 44 | 1.150 |
| Water level over 25% of pipe diameter | 279 | 7.292 |
| Dirt Deposits | 911 | 23.811 |
| Total | 3826 | 100 |

Defects that are included in the misalignment category are offset joints over 3 cm, open joints over 5 cm, opposite slopes, visible soil, sagging pipes, right lateral deviation, left lateral deviation and visible rubber gasket at the joint. This category is suggested due to the fact that a crescent shape is usually formed at the joint when any of the mentioned defects exists. Infiltration category includes sign of infiltration, sign of infiltration at the joint, water infiltration, water infiltration at the joint and mineral accumulation. This category is suggested due to the fact that they all share the same effect of having a wetted area around the defect. Dirt deposits result in building up of foreign materials on the bottom of a pipe, and accordingly it was considered to fall in a separate category. Cross-sectional reduction category includes all objects that obstruct the flow in pipes such as roots. Longitudinal and circular cracks were grouped in one category (i.e. Cracks) due to their common geometrical features (i.e. length and width). Defects such as broken pipes, broken joints, visible armature along the pipe, visible armature at the joint, multiple cracks and grease accumulation were grouped in one category due to the fact that their possibility of existence is very minimum. Category of side effects includes increasing of water level over 25% of pipe diameter. This is due to the fact that this phenomenon could be attributed to more than one defect. These defects are opposite slopes, existence of roots or solid deposits at the bottom of a pipe.

It should be noted that defects such as roots, infiltration and deposits are considered to be serious problems by many municipalities in North America. It has been reported that the intrusion of roots to sewers (FIG. 2) is the most important factor contributing to their blockage in North America. It has also been reported that the blockage of sewer pipes caused by root intrusion increases by 3% yearly. Naturally, roots search for a nutritious source for survival. Once a sewer pipe is found, it is considered to be a perfect environment. The roots then penetrate the pipe through any opening, such as an open or broken joint. After penetration, they grow in until they reach the flow. Once they reach the flow, they grow more and collect solids until they form a blockage. Beside roots being a major factor contributing to blockage of sewer pipes, they could also cause structural and functional failure to these pipes. This is due to their ability to uplift pipes, which could result in creation of cracks or opening of joints.

Deposits in sewer pipes (FIG. 3) have been reported to be a worldwide problem. A recent survey in the United Kingdom has revealed the presence of large amounts of deposits in their sewer pipes. Usually, deposits consist of a mixture of coarse sediments, fine sediments and organic material. The coarse and fine sediments find their way into sewer pipes through defects in manholes or joints. These deposits have been reported to cause erosion of pipes as well as loss of discharge capacity.

Infiltration of ground water into sewer pipes (FIG. 4) is a major problem that faces most municipalities. Infiltration has been reported to account for 40% of the total flow in sewer pipes. This unnecessary extra flow contributes to serious problems such as overloading of sewer pipes and wastewater treatment plants. This phenomenon has also been documented to account for an additional 10%, at least, to treatment cost. It should be noted that water infiltrates sewer pipes through defected joints, manholes or cracks.

The two common types of cracks are longitudinal and circular (Table A). These cracks are mostly caused due to two main reasons. These reasons are frequent overload and/or presence of uneven pipe support. Cracks are considered to be the preliminary stage of sewer pipe fracture. This is due to the fact that once they are developed, water could exfiltrate or infiltrate from/to the surrounding soil. If side supports are lost due to washing out of soil particles, caused by exfiltration or infiltration processes, cracks will be developed into fractures. It should also be noted that if a pipe further moves outwards, due to absence of enough side support, it eventually collapses.

Defective joints (FIG. 6) were found to be one of the main categories of defects in sewer pipes, see also FIG. 1. They are mostly caused due to loss of supporting soil. This is usually initiated by having a defective gasket. These defective gaskets allow for the infiltration or exfiltration process to take place, which will eventually cause the supporting soil to be disturbed. This disturbance of the supporting soil causes pipes to settle and their joints open. It should be noted that once open joints are created, cracks could also be initiated which could eventually result in pipe failure.

Figure 7:
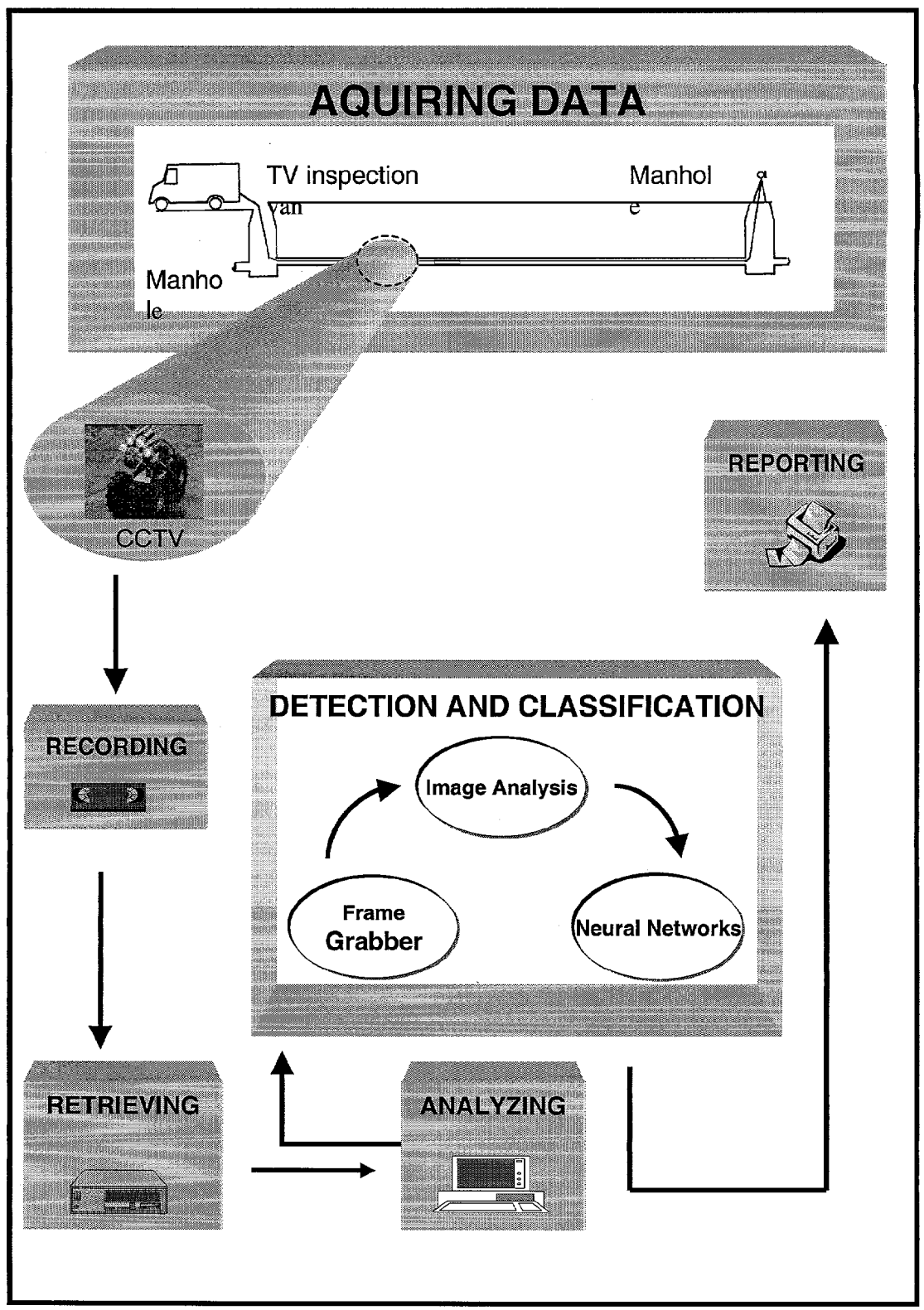
FIG. 7 shows the Proposed Automated Detection and Classification System.

FIG. 7 depicts the overall configuration of the automated inspection system. As depicted in FIG. 7, a CCTV, or a zooming, camera first scans the inner surface of a pipe and produces a videotape which is played back using a VCR. The VCR then feeds the information captured on the tape to a computer equipped with a frame grabber, image analysis and neural network software. The frame grabber captures and digitizes the frames of the acquired images. The image analysis software analyzes those digitized images and processes them in a manner so as to prepare a suitable input to a neural network. Based on those analyzed images, some feature vectors are extracted, using different image analysis techniques, and are fed to several neural networks for training. The trained networks can then be used to classify new set of defects based on their extracted features.

As can be noticed, the system utilizes a CCTV camera as its main component for scanning and collecting information about pipes. This technique of video imaging was selected to benefit from the long experience gained by municipalities and practitioner engineers in using this particular data collection device. This particular data collection device was also preferred, compared to others, due to its availability, affordable cost and proven capabilities. Utilizing the CCTV camera, as a data collection device in the developed system, also builds on the experience gained by municipalities in inspecting sewer pipes, and does not overburden them with purchasing new data collection devices that might be expensive, under development or not available in local markets. By keeping the momentum gained by municipalities in utilizing the CCTV camera, the proposed system will facilitate the detection and classification processes of most common defects in sewer pipes, namely cracks, misalignments, infiltration, cross-sectional reduction and deposits by using an automated process. The system is designed to speed up the detection and classification processes so that minimum processing time is required. This is achieved by extracting from video images all necessary and essential information required for performing its task. This will minimize the processing time to a degree that the system could be utilized in on-line inspection tasks.

Figure 8:
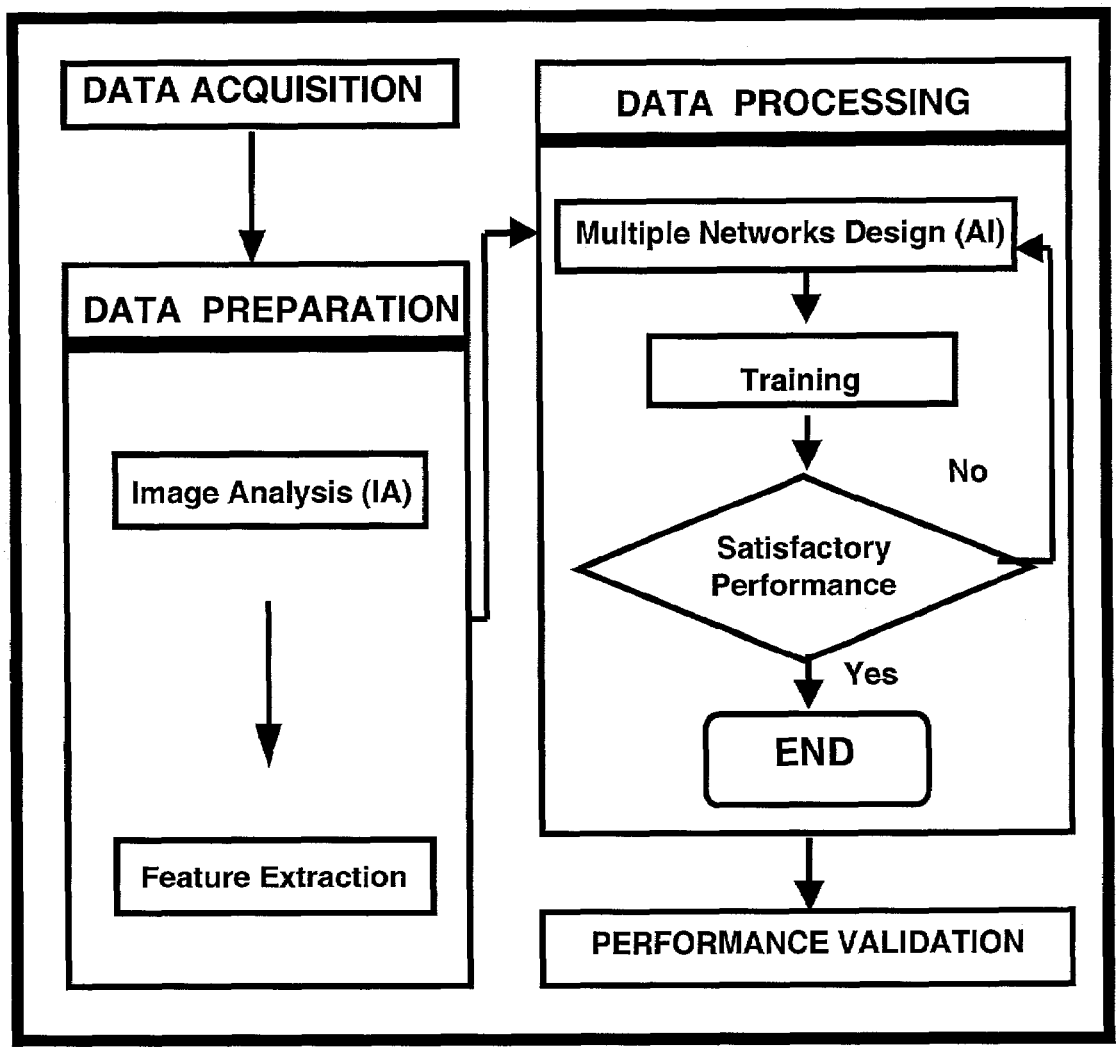
FIG. 8 shows the Methodology for Developing Automated Detection System.

FIG. 8 depicts the methodology followed in developing the automated inspection system. As can be seen, four main steps were followed: 1) data acquisition, 2) data preparation, 3) data processing and 4) performance validation. In the following sections, a detailed description of each step is presented.

Data Acquisition

A total of five videotapes were collected from several municipalities and sewer rehabilitation contractors. These videotapes depict the condition of sewer pipes in several cities such as Montreal and Hamilton, Canada. They also depict all common types of defects that exist in sewer pipes. These defects are cracks, misalignments, infiltration, deposits and cross-sectional reductions. Moreover, images depicting all various defects were extracted from these collected videotapes and presented to consultants in the domain of sewer rehabilitation for verification of their types.

Data Preparation

Neural networks are recognized for their superior performance in pattern recognition and classification capabilities. As a rule of thumb, the number of neurons in the input layer has to be minimized so that the computation and conversion speed can be maximized. Reducing the number of neurons can also help in improving the learning process of neural networks.

Data captured on video images were utilized to train neural networks on detecting and classifying various defects in sewer pipe. A typical video image may consist of 760×480 pixels. If this image is to be processed using neural networks, then at least two alternatives could be considered. First is to digitize and feed one image or frame at a time with its huge number of pixels into the neural network. The second is to extract feature vectors that represent the different objects in the image and then feed them into the neural network. It should be noted that a feature vector is defined as a set of geometrical and statistical attributes that describe an object (i.e. defect) and its surroundings in a video image.

Clearly, the first alternative is impractical since one neuron will be needed for each single pixel in the image. This requires a huge number of neurons in the input layer that could not be handled efficiently by the neural network and, accordingly, could degrade the classification performance or delay the processing time. The second alternative appears to be promising and will be considered in subsequent developments of the proposed system. This alternative has been found useful in pattern classification using neural networks. The technique basically minimizes the amount of data that has to be fed into a neural network and, accordingly, reduces significantly the number of neurons in the input layer of that network. It ultimately results in improving the learning speed as well as the classification capabilities of the network.

In preparing the data, all acquired videotapes were digitized. A commercial software package was utilized for this task. This software package is Adobe PhotoShop. Once all images have been digitized, they were processed and analyzed utilizing a commercial image analysis software package. This software package is Scion Image. Various image analysis techniques such as inverse transformation, edge detection, background subtraction, dilation and thresholding were utilized in processing and analyzing the digitized video images. It should be noted that the aim of these techniques is to detect and isolate defects from image background. Once defects were detected and isolated, they were analyzed to determine their relevant attributes (i.e. geometrical and pixels intensities). It should be noted that the process of determining object attributes is called feature extraction.

Data Processing

Selecting a Neural Network Paradigm

There are different types of neural networks, each of which is considered suitable for a certain application. Back-propagation neural networks are recognized for their superior performance in classification tasks. They are also considered the most commonly used type of neural network in civil engineering applications. It should also be noted that this type of network was previously used in developing an automated system for classification of defects in pavements and proved its superior capabilities. Accordingly, this type of network will be utilized in developing the automated system.

Network Design and Training

Contrary to developing traditional algorithmic computer programs, designing and developing neural network applications is heavily dependent on trial and error. This is due to the fact that there are a number of parameters contributing to their design and eventually, to their performance. Although there are some guidelines for selecting reasonable initial values for these parameters, there are no rules that assure selection of most suitable values before hand. Accordingly, the process involves a lot of trials until satisfactory performance is obtained. Basically, in designing neural networks, the following parameters are considered: Activation and scaling functions, Number of hidden layers, Number of neurons in hidden layers, Number of neurons in input and output layers, Learning rate coefficient, Momentum coefficient.

Prior Art techniques are utilized in selecting reasonable initial values for these parameters.

The total acquired data will be randomly divided into three sets: 60% for training, 20% for testing and another 20% for production. It should be noted that the testing set is a set of patterns that are used to test the generalization capabilities of the network while in training. In so doing, the training process temporarily stops, after a pre-specified number of training iterations (calibration interval), and computes the average error for the training set. The production set is a set of patterns that are not exposed to the network while training or testing and is used to test the performance of the trained network.

Result Validation

Once the neural networks have been designed and trained, their capabilities will be tested on a different set of defects that they were not exposed to during development. This will be achieved by utilizing the production set. It should be noted that the satisfactory performance of each developed neural network will be measured based on several parameters. These parameters are (R2), mean square error, mean absolute error, minimum absolute error, maximum absolute error, correlation coefficient and recognition rate.

Figure 9:
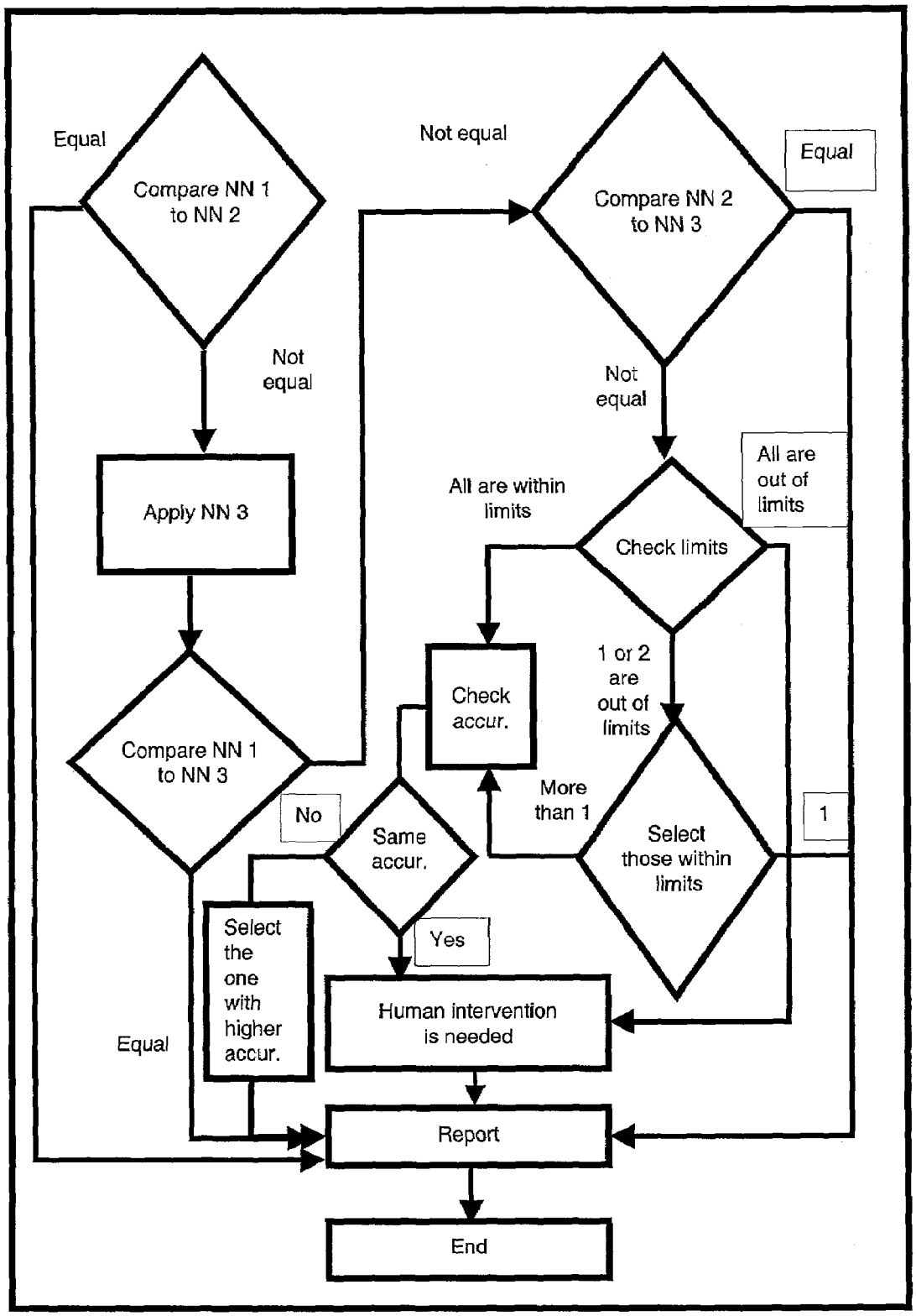
FIG. 9 shows the Algorithm of the Multiple Classifier System.
Figure 10:
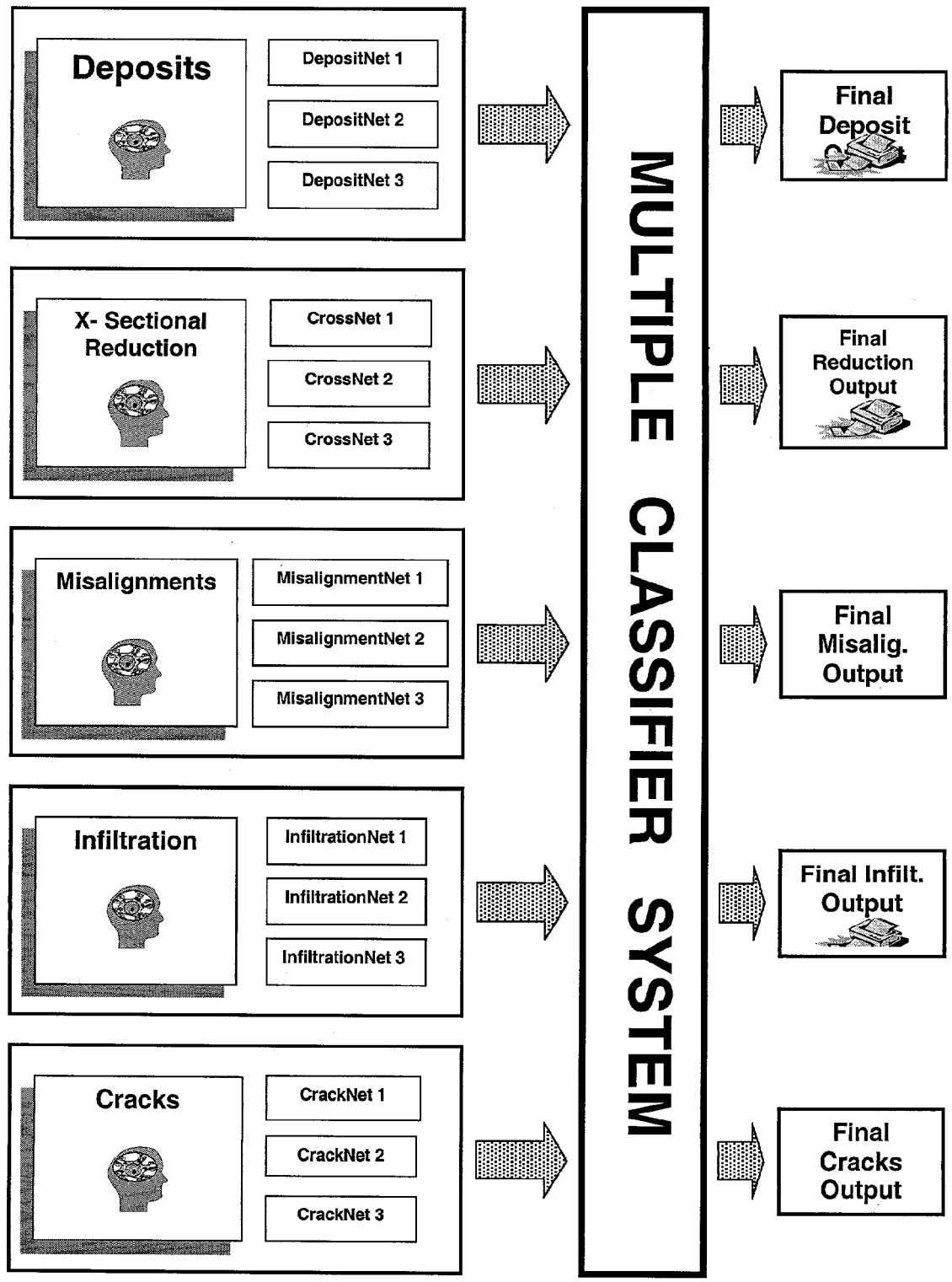
FIG. 10 shows the Utilization of the Multiple Classifier System.

In an effort to improve the overall accuracy of the developed inspection system and the user's confidence in its obtained results, three neural networks will be developed for each category of defects. These networks are designed to counter-check the results obtained from each other, embracing a multiple classifier strategy. In essence, they function in a similar way to a team of human experts. FIG. 9 depicts the proposed methodology of comparing the output of the three networks. As depicted in FIG. 9, when the multiple classifiers system is activated, it first compares the output of two networks (i.e. neural network no.1 and no.2). If their results match each other, then a report will be issued stating the classification of defect agreed upon by both networks. If their results do not match, then a third network will be applied. If the results obtained from the third network match the results obtained from any of the previously applied networks (i.e. neural network no.1 or no.2), then a report will be issued confirming the two matched classifications. If the results obtained from the three networks are different, then the defect features vector will be compared with the upper and lower boundaries of each network (i.e. the range in which the neural networks have been trained). If the defect features vector is outside the boundary limits of the three networks, then a message will be given to the user to consult a human expert to identify the actual type of defect encountered. If the features vector of the defect in question falls within the boundary limits of one network only, then the results obtained from that network will be reported. If the features vector of the defect in question falls within the boundary limits of more than one network, then the results obtained from the network with the highest accuracy (i.e. recognition rate) will be reported. If more than one network were found to have the same accuracy, then a human intervention is needed. It should be noted that the recognition rate is measured as the percentage of correctly classified cases out of a number of cases that were not encountered by the neural network during the training stage (i.e. production set). FIG. 10 depicts the utilization of the proposed multiple classifier system and its integration with the main detection and classification system.

Neural networks work in an analogous way to human experts. The more focused the expert is in a specific domain of application, the higher are the expectations to solve difficult problems. In this chapter, several classifiers (i.e. neural networks) are developed; each is considered suitable for a certain category of defects. This was considered advantageous, as opposed to one network that classifies more than one type of defect, in order to express and demonstrate the importance of specialty in classification tasks. Although diversity of networks is advantageous, it leads to a problem of guiding the detected patterns in the proper direction that will ensure that each category of defect is received by its corresponding specialized classifier. In this section, a solution strategy is presented to organize data traffic so as to guide the patterns in their proper directions and accordingly improves the system's performance.

Figure 11:
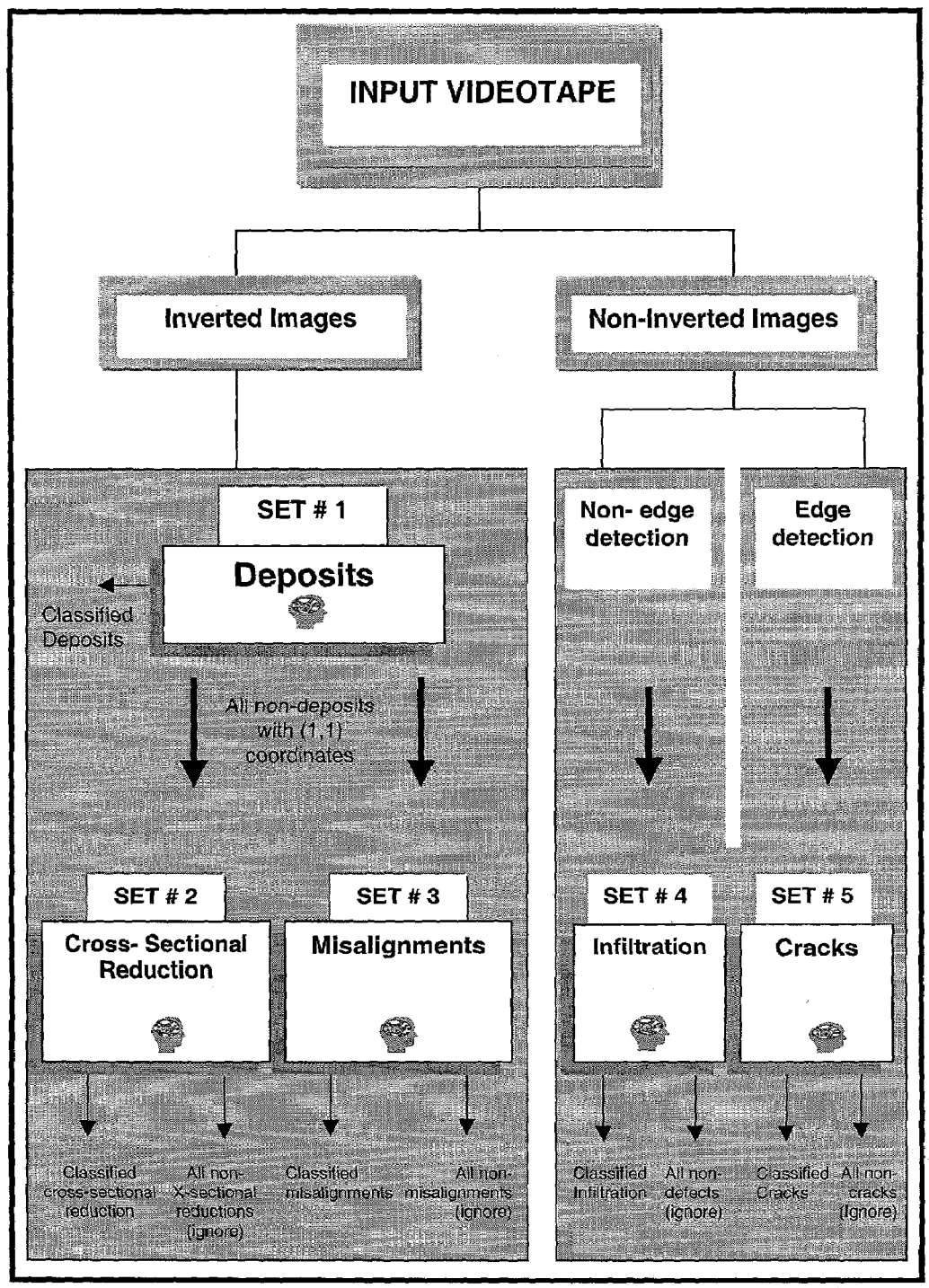
FIG. 11 shows the Solution Strategy.
Figure 12:
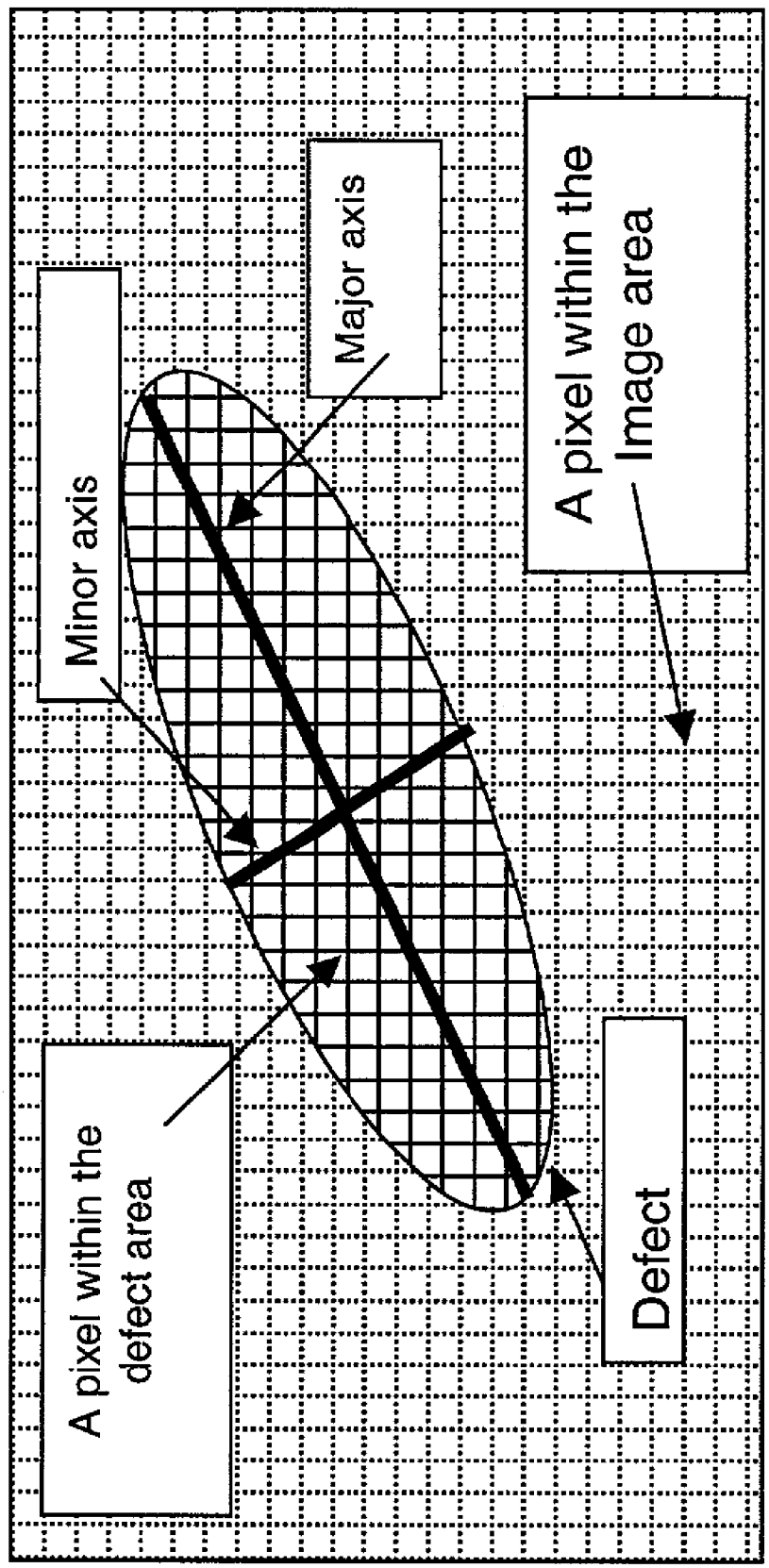
FIG. 12 shows the Geometrical Attributes of Defects.

FIG. 11 depicts the proposed solution strategy. As depicted in this figure, all images will be processed three times. In the first pass (i.e. inverted images), all images will be inverted, dilated, background subtracted, thresholded, segmented and finally analyzed. In the second pass (i.e. non-edge detection), images will be subjected to the same image processing techniques except inversion. In the third pass (i.e. edge detection), all images will be subjected to a number of operations. These operations are background subtraction, edge detection, dilation, thresholding and analysis. The sequence of these image processing operations and their associated outputs are summarized in Table B. The reason behind subjecting the same videotape to a number of passes is to benefit from all image processing techniques that are necessary to detect all categories of defects recognized by the system.

TABLE B

Sequence of Image Processing Operations and Detected Defects

| Pass # | Sequence of Operation | Detected Defects |
| --- | --- | --- |
| 1 | Inversion, dilation, background subtraction, thresholding, segmentation and analysis | Deposits, Cross-sectional reductions and misalignments |
| 2 | dilation, background subtraction, thresholding, segmentation and analysis | Infiltration |
| 3 | background subtraction, edge detection, dilation, thresholding and analysis | Cracks |

TABLE B-continued

Sequence of Image Processing Operations and Detected Defects

| Pass # | Sequence of Operation | Detected Defects |
| --- | --- | --- |

As can be seen in FIG. 11, results of the first pass (i.e. inverted images) will first be processed by set of networks number 1, specialized in detecting deposits. This set consists of three networks: DepositNet 1, DepositNet 2 and DepositNet 3. These networks will classify the input data (i.e. patterns) into two categories: "Deposits" and "Else" (i.e. non-deposits). All patterns classified as "Else" will be screened based on their X and Y coordinate and will be further processed by another two sets of networks (i.e. sets no.2 and 3), each is specialized to deal with a specific set of defects. Patterns with X and Y coordinates equal to (1, 1) will be fed into these networks specialized in classifying cross-sectional reductions and misalignments (i.e. set no. 2 and 3, respectively). It should be noted that set number 2 and 3 consist of three networks each. These networks are Cross-sectionalNet 1, Cross-sectionalNet 2, Cross-sectional 3, MisalignmentNet 1, MisalignmentNet 2 and MisalignmentNet 3. It should be noted that all patterns classified as "Else" by set #2 and 3 will be ignored since they could be non-defects or defects that are not recognized by the system.

The results of the second pass of image processing (i.e. non-edge detection) will be fed into those networks specialized in classifying infiltration (i.e. set no 4). This set consists of three networks: InfiltrationNet 1, InfiltrationNet 2 and InfiltrationNet 3. Each network is capable of classifying patterns into two categories: "Infiltration" and "Else" (i.e. non-infiltration). It should be noted that all patterns classified as "Else" will be ignored since they could be non-defects or defects that are not recognized by the system.

The results of the third pass of image processing (i.e. edge detection) will be fed into the A networks specialized in classifying cracks (i.e. set no 5): CrackNet 1, CrackNet 2 and CrackNet 3. Each network is capable of classifying patterns into two categories. These categories are "Crack" and "Else" (i.e. non-crack). It should be noted that all patterns classified as "Else" will be ignored since they could be non-defects or defects that are not recognized by the system.

As described earlier, there are five major categories of defects. These categories are cracks, misalignments, deposits, infiltration and cross-sectional reductions. Since a human expert, by definition, is specialized in a specific domain of application, and neural networks function in an analogous way to a human expert, it was believed that it would be advantageous to develop separate neural networks, each is specialized in classifying a specific type of defect. Accordingly, the methodology described previously in Section 3.4 will be utilized to develop five sets of neural networks, each consisting of three networks. The first, second, third, fourth and fifth sets will be designated to cracks, cross-sectional reductions, deposits, misalignments and infiltration, respectively. The following sections describe the development of each set of neural networks. Case examples will also be presented to demonstrate the use and capabilities of the developed neural networks.

Cracks

There are two types of cracks considered in this system, longitudinal and circular. They all posses the same attributes, except orientation (i.e. angle). Longitudinal cracks run parallel to the pipe axis, while circular ones run along the circumference of the pipe. They are characterized by distinctive features. These features are small width, large length and large length to width ratio. In order to extract these distinguishing features, image analysis techniques will be applied utilizing Scion Image software package (Scion Image 1998). Image analysis techniques will process defects so as to enhance and isolate them from their background, and finally analyze them to determine their attributes. These attributes are area, mean density, standard deviation, X-coordinate, Y-coordinate, modal density, perimeter, major axis, minor axis, angle, integrated density, modal value of background, minimum gray value, maximum gray value, the ratio of major axis length to the minor axis length, the ratio of perimeter to area and the ratio of mean gray level value of defect to mean gray level value of image. These parameters were defined above.

Figure 15:
FIG. 15 is a photograph showing Dilated Image of Cracks.
Figure 16:
FIG. 16 is a photograph showing Thresholded Image of Cracks.
Figure 13:
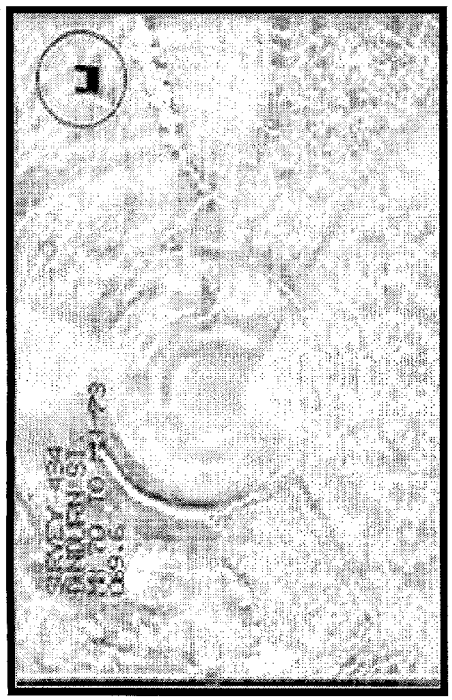
FIG. 13 is a photograph showing Background Subtracted Image of Cracks.
Figure 14:
FIG. 14 is a photograph showing Edge Detected Image of Cracks.
Figures 17, 18:
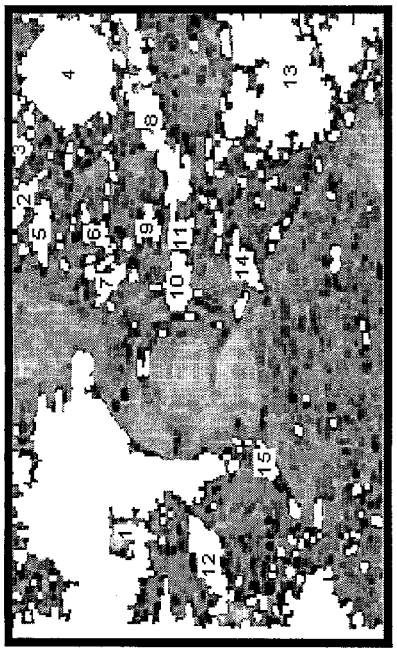
FIG. 17 is a photograph showing Segmented Image of Cracks.
FIG. 18 shows the Analysis Results of an Image Depicting Cracks.

Various image analysis techniques were tried and analyzed, aiming to enhance the image of defects and isolate them from background, such as inversion, dilation background subtraction, threshholding, smoothing, erosion and edge detection. Finding a set of techniques that could be applied to all types of cracks, regardless of their gray level value, was a challenge. This is due to the fact that some cracks were found to have a high gray level value (i.e. white or close to white) and others were found to be vice versa (i.e. black or close to black). The techniques found to yield best results are edge detection, dilation, background subtraction and threshholding. Edge detection is utilized to outline the cracks regardless of being black or white (FIG. 14). Dilation is utilized to fill in the gaps and connect discontinuous pixels (FIG. 15). This is achieved by filling in these gaps by pixels with gray level value similar to their neighborhood dark pixels. It should be noted that these gaps are created due to discontinuity of gray level values (i.e. a group of light pixels in between two groups of dark pixels). Background subtraction is utilized to isolate cracks from the background of an image (FIG. 13). This was found very helpful in obtaining good results form the thresholding operation that will follow. In this operation, all background pixels are deleted from the image and only cracks remain. Thresholding is utilized to isolate cracks and prepare them for the analysis stage (FIG. 16). Once the image has been thresholded, it becomes ready for analysis. In this step, all above described attributes are measured (FIGS. 17 and 18). It should be noted that several sequences of operation were tried and the sequence found to yield the best results is sequence number 3 as detailed in Table B.

This sequence of operations was conducted on the collected images. Three hundred and seventy one cracks were detected, isolated and analyzed. The results obtained from this analysis were utilized in developing three neural networks. The purpose of these networks is to classify cracks from non-cracks, based on their attributes calculated in the analysis process.

Based on the extracted feature vectors of various defect types, it was noticed that misalignments might have almost the same attributes as cracks. This is due to the difference in distance between the CCTV camera and each type of defect. In other words, misalignments away from the camera tend to have similar attributes to cracks closer to the camera. These similar attributes are small minor axis length, small area and large ratio of major axis length to minor axis length. The only factors that differentiate between the apparently similar attributes are the X and Y coordinates (i.e. location). It was noticed, from the collected sample of video images, that the center of an image is darker than its surrounding area. This is due to the fact that the lighting effect vanishes as the distance from the lighting source gets larger. It was also noticed that misalignments tend to be illuminated at this specific area (the center of an image). This is due to the fact that these defects tend to project from the surface of the pipe and reflect back the beam of light they are exposed to. Other defects such as cracks do not exhibit the same phenomena. This was utilized to facilitate the classification process by assigning the coordinates of objects located outside this dark area to (0, 0) (Moselhi and Shehab-Eldeen 1999 (b) & 2000 (a)).

In view of the proven capabilities of back-propagation neural networks in classification tasks and to their wide versatility in different civil engineering applications, this paradigm was utilized in developing the automated inspection (detection and classification) system. The literature review discussed in Chapter Two was carefully considered in designing neural networks. Described below are the parameters used in setting the preliminary design of networks.

Since the number of neurons in the input layer should equal the number of attributes in the feature vector that was selected to represent the input patterns, it was decided to use seventeen neurons in that layer.

Since the number of neurons in the output layer should equal the desired number of categories, the output layer of the developed network was built consisting of two neurons (i.e. one for each class of defects). These classes are "Cracks" and "Else".

In the developed network, a three-layer network was used (i.e. one hidden layer).

For the number of neurons that should be used in the hidden layer, the following equation has been applied in selecting the preliminary 30 neurons in the hidden layer.

$$N=0.5(X+Y)+\sqrt{Z} \qquad (1)$$

Where: N=Number of neurons in the hidden layer; X=Number of input parameters; Y=Number of output categories; Z=Number of patterns in training set.

Other parameters such as the type of activation & scaling functions, initial weights, learning rate and momentum factor are listed in Table C.

TABLE C

Initial Parameters Used in designing a Preliminary Neural Network for Classification of Cracks

| Parameter | Value |
|---|---|
| Network paradigm | Back-propagation |
| Number of neurons in input layer | 17 |
| Number of neurons in output layer | 2 |
| Number of neurons in hidden layer | 30 |
| Number of hidden layers | 1 |
| activation function in hidden layer | Sine |
| Activation function in output layer | Logistic |
| Initial weight | 0.4 |
| Learning rate | 0.3 |
| Momentum | 0.4 |
| Calibration interval | 50 |
| Saving of network | At the best testing set |

Figure 19:
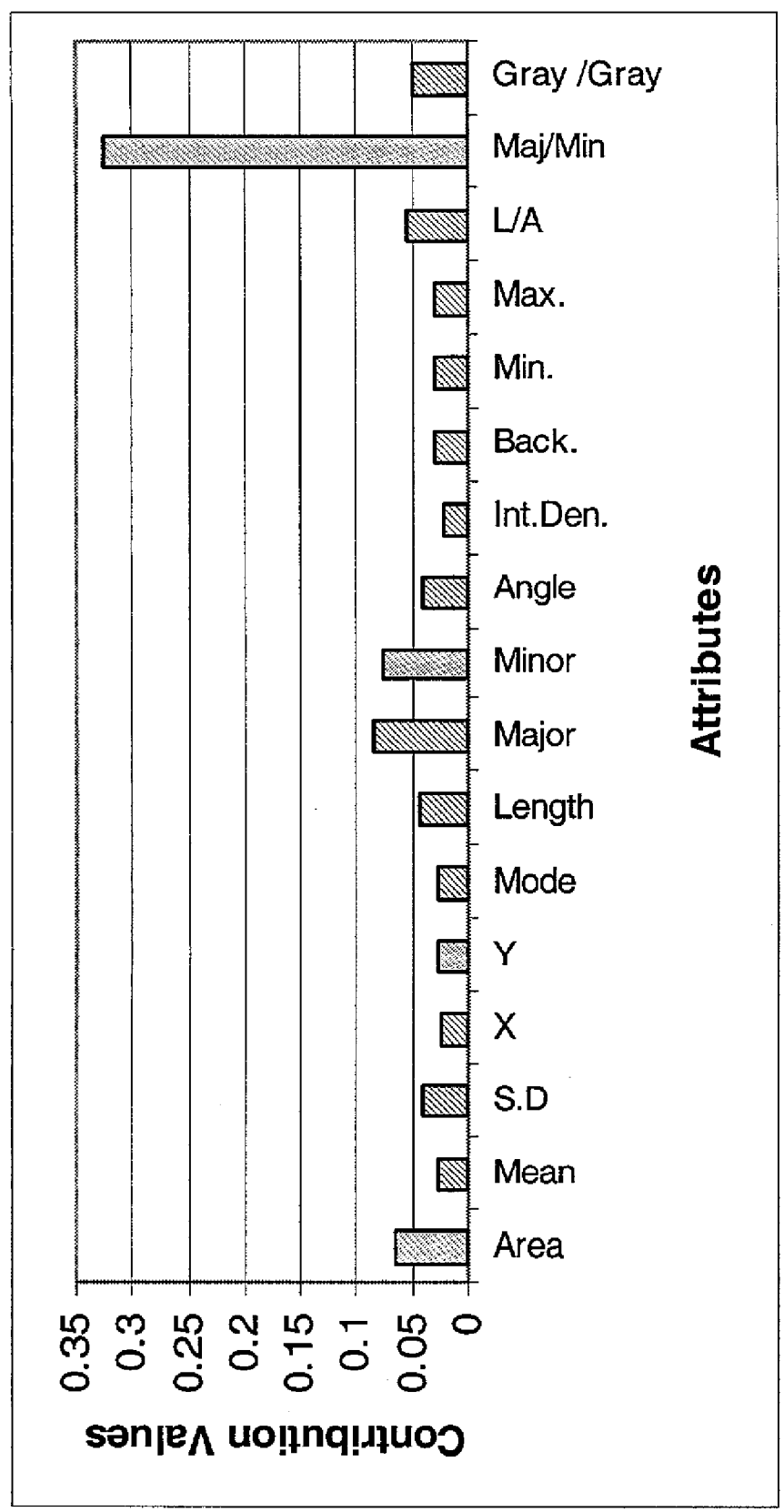
FIG. 19 shows the Contribution Values of Attributes Utilized in Designing the Preliminary Neural Network for Classification of Cracks.

The developed three-layer back-propagation network was trained to classify two categories. These categories are "Cracks" and "Else". The network was developed and trained using NeuroShell-2 software package. The process was implemented on a Pentium II computer with 233 MHz processor and 64 MB RAM. A total of 966 patterns were used in developing the network. The total number of patterns was randomly divided as follows: 580 patterns (60%) for training, 193 patterns (20%) for testing and 193 patterns (20%) as a production set. These different sets have been defined earlier in Section 3.4.3.2. It should be noted that the training algorithm was set to save the trained network at the best test set and limit the calibration interval to 50. This was done so that over-training of the network is monitored and prevented. It should be noted that over training causes the network to memorize rather than generalize (Fausett 1994). Various combinations of hidden neurons, activation and scaling functions were tried and the near optimum design was found to be 17 neurons in the input layer, 34 neurons in the hidden layer and 2 neurons in the output layer. Linear scaling, Gaussian and Logistic activation functions were selected for the input, hidden and output layers, respectively. The results obtained using the developed network are shown in Table D. It should be noted that these results are for the 193 patterns not seen by the network during training (i.e. production set). Based on this trained network, the contribution of each input variable was calculated (FIG. 19). These contributions illustrate the relative importance of each variable to the performance of the network.

TABLE D

Performance Results of a Preliminary Neural Network for Classification of Cracks

| Performance Criteria | Crack | Non-Cracks |
|---|---|---|
| $R^2$ | 0.82 | 0.82 |
| Mean squared error | 0.042 | 0.042 |
| Mean absolute error | 0.095 | 0.095 |
| Min. absolute error | 0 | 0 |
| Max. absolute error | 1.0 | 1.0 |
| Correlation coefficient (r) | 0.90 | 0.90 |
| Recognition rate | 98.6% | 93.3% |

Figure 20:
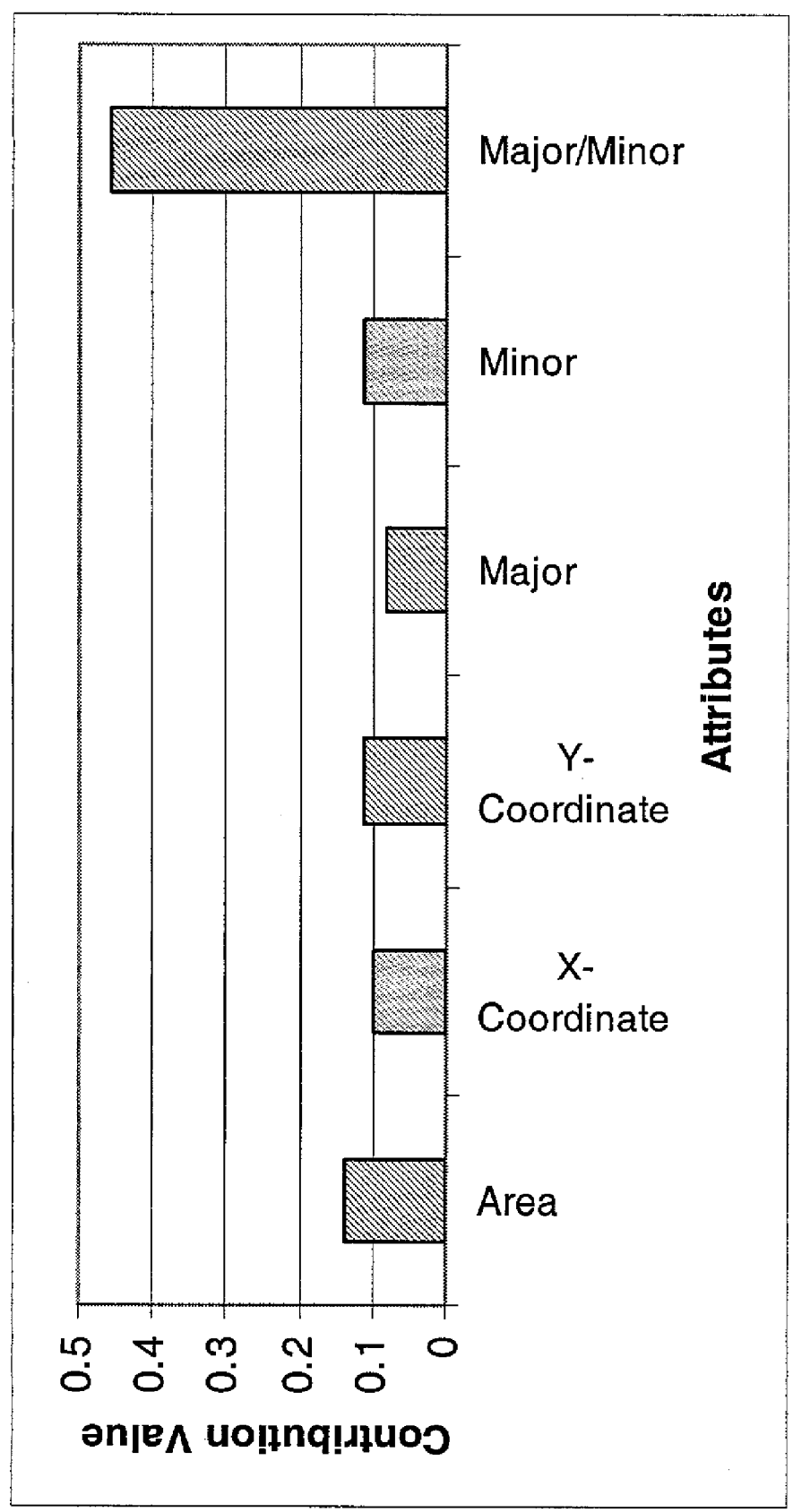
FIG. 20 shows the Contribution Values of Attributes Utilized in Designing Neural Network #1 for Classification of Cracks.

In an effort to improve the performance of the network, a sensitivity analysis was carried out to study the effect of reducing the number of attributes on the overall performance of the network. The general performance of the network was measured in accordance to the values of the coefficient of multiple determination (R2), the correlation coefficient (r) and recognition rate. In this analysis, several networks with different input attributes were developed and their performance was compared. Based on the analysis of the results obtained, 6 attributes were used in the input layer of the developed network (Moselhi and Shehab-Eldeen 2000 (a)). These attributes are area, X-coordinate, Y-coordinate, major axis length, minor axis length and the ratio of major axis length to the minor axis length. FIG. 20 depicts the contribution values for the selected attributes. The developed network (i.e. CrackNet 1) was tested on the production set (193 cases, not seen by the network during training). The results shown in Table E depict noticeable improvement in the performance of the developed network. Table F also lists the final parameters that were considered in designing this network.

TABLE E

Performance Results of CrackNet 1

| Performance Parameters | Crack | Non-Cracks |
|---|---|---|
| $R^2$ | 0.92 | 0.92 |
| Mean squared error | 0.016 | 0.016 |
| Mean absolute error | 0.047 | 0.047 |
| Min. absolute error | 0 | 0 |
| Max. absolute error | 0.82 | 0.82 |
| Correlation coefficient (r) | .96 | 0.96 |
| Recognition rate | 97.2% | 100% |

TABLE F

Final Parameters Used in Designing CrackNet 1

| Parameter | Value |
|---|---|
| Network paradigm | Back-propagation |
| activation function in hidden layer | Gaussian |
| Activation function in output layer | Logistic |
| Number of neurons in input layer | 6 |
| Number of neurons in output layer | 2 |
| Number of neurons in hidden layer | 31 |
| Number of hidden layers | 1 |
| Initial weight | 0.7 |
| Learning rate | 0.2 |
| Momentum | 0.2 |
| Calibration interval | 50 |
| Saving of network | At the best testing set |

Figure 21:
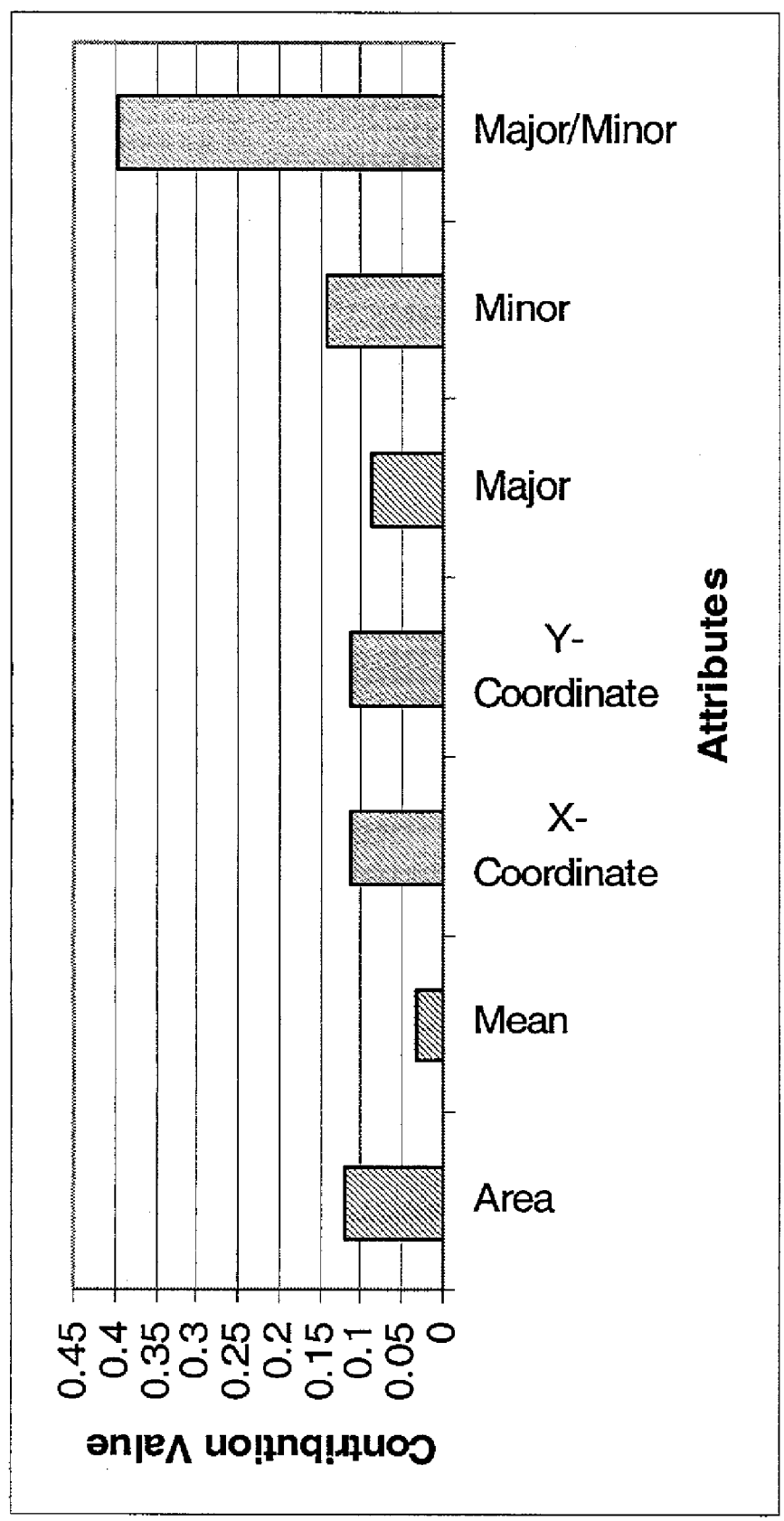
FIG. 21 shows the Contribution Values for the Selected Attributes Utilized in Designing CrackNet 2.
Figure 22:
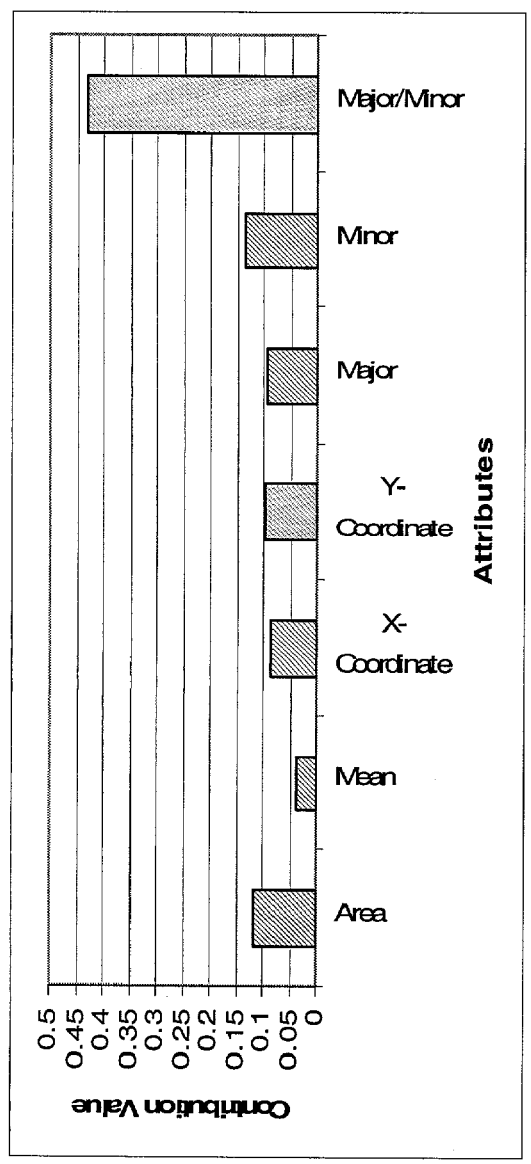
FIG. 22 shows the Contribution Values for the Selected Attributes Utilized in Designing CrackNet 3.

As can be noticed, all attributes considered by CrackNet 1 are geometrical. Although these geometrical attributes were found to be sufficient for the classification task, it was felt that introducing attributes related to intensity of pixels would be advantageous. This is due to the fact that any photographed object is described by two main parameters: geometry and color. If one of them is missing, an incomplete description could be expected. Accordingly, another sensitivity analysis was conducted aiming at introducing as many attributes as possible related to intensity of pixels. The challenge was to keep the performance of the newly developed neural networks as high and as close as possible to performance of the network that considers geometrical attributes only. The results of this sensitivity analysis revealed that introducing the mean gray level value will not dramatically affect the performance of classification (Tables G and I). Tables G and I show the performance of CrackNet 2 and CrackNet 3, respectively. The contribution values of attributes for these two developed networks are shown in FIGS. 21 and 22. Tables H and J list also the parameters utilized in designing and developing these two networks.

TABLE G

Performance Results of CrackNet 2

| Performance Parameters | Crack | Non-Cracks |
|---|---|---|
| $R^2$ | 0.90 | 0.90 |
| Mean squared error | 0.022 | 0.022 |
| Mean absolute error | 0.049 | 0.049 |
| Min. absolute error | 0 | 0 |
| Max. absolute error | 1.0 | 1.0 |
| Correlation coefficient (r) | .95 | 0.95 |
| Recognition rate | 98.6% | 98% |

TABLE H

Final Parameters used in designing CrackNet 2

| Parameter | Value |
| --- | --- |
| Network paradigm | Back-propagation |
| activation function in hidden layer | Gaussian |
| Activation function in output layer | Logistic |
| Number of neurons in input layer | 7 |
| Number of neurons in output layer | 2 |
| Number of neurons in hidden layer | 41 |
| Number of hidden layers | 1 |
| Initial weight | 0.7 |
| Learning rate | 0.2 |
| Momentum | 0.2 |
| Calibration interval | 50 |
| Saving of network | At the best testing set |

TABLE I

Performance Results of CrackNet 3

| Performance Parameters | Crack | Non-Cracks |
| --- | --- | --- |
| $R^2$ | 0.87 | 0.87 |
| Mean squared error | 0.029 | 0.029 |
| Mean absolute error | 0.059 | 0.058 |
| Min. absolute error | 0 | 0 |
| Max. absolute error | 1.0 | 1.0 |
| Correlation coefficient (r) | 0.93 | 0.93 |
| Recognition rate | 94% | 98.6% |

TABLE J

Final Parameters Used in Designing CrackNet 3

| Parameter | Value |
| --- | --- |
| Network paradigm | Back-propagation |
| activation function in hidden layer | Gaussian |
| Activation function in output layer | Logistic |
| Number of neurons in input layer | 7 |
| Number of neurons in output layer | 2 |
| Number of neurons in hidden layer | 25 |
| Number of hidden layers | 1 |
| Initial weight | 0.7 |
| Learning rate | 0.2 |
| Momentum | 0.2 |
| Calibration interval | 50 |
| Saving of network | At the best testing set |

Figure 5:
FIG. 5 is a photograph showing Cracks.
Figure 23:
FIG. 23 is a photograph showing Segmented Image of a Case Example on Cracks.

To demonstrate the use and capabilities of the developed neural networks, the image shown in FIG. 5 was considered. As can be noticed, this image depicts longitudinal cracks. To detect and classify these defects, the image was processed in the same manner as shown in FIGS. 13 to 18. It should be noted that the segmented image is shown below for easy reference (FIG. 23). As can be noticed, the segmented image depicts 15 objects. The parameters of these objects are shown in FIG. 18. Based on location, all objects were assigned (0, 0) and (1, 1) for their X and Y coordinates. These objects were then fed into the already trained neural networks for classification purpose. The results obtained from a sample network are shown in FIG. 24.

Figure 24:
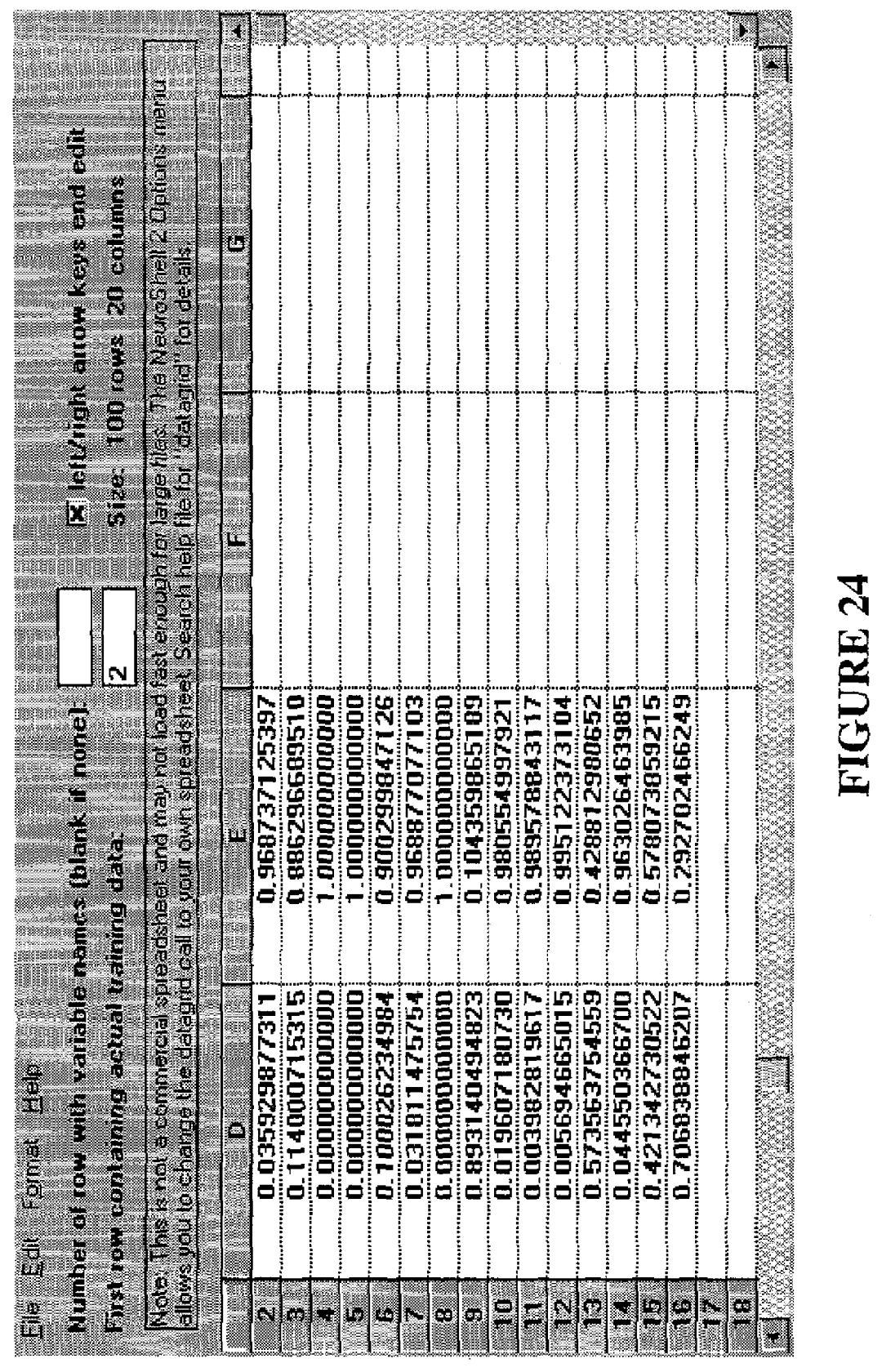
Figure 25:
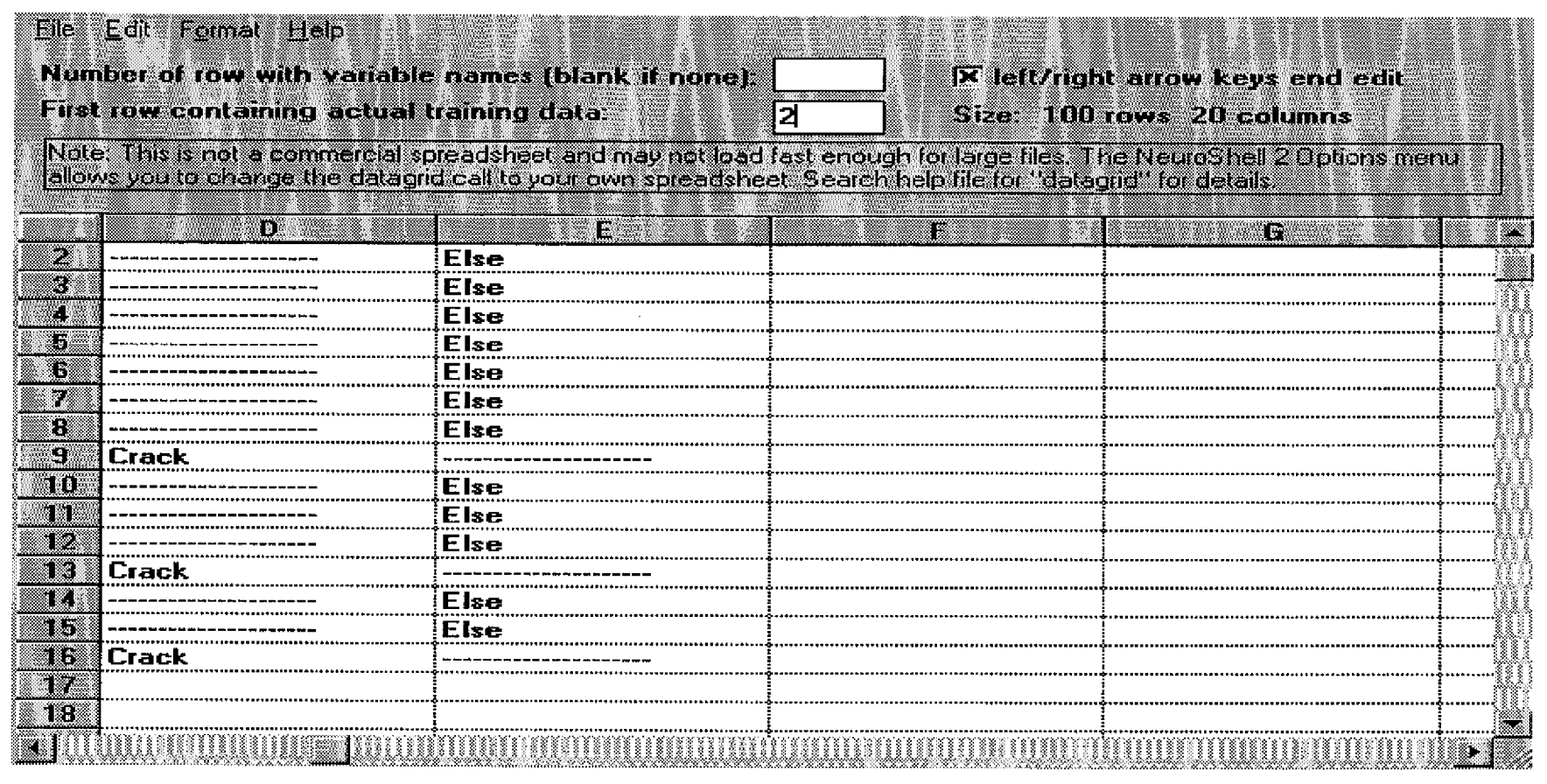

As can be noticed from FIG. 24, the output values range from 0 to 1. These values can be considered as the probability that a certain object belongs to either of the two categories recognized by the developed network (i.e. Cracks and Else). For example, the probability of object number 6 being classified as a Crack and Else is 10% and 90%, respectively. A threshold value of 50% was considered sufficient for positive classification. As such, if the probability that a certain object belongs to a certain category exceeds 50%, then this object is considered to fall in that category. Although a default value of 50% was used for classification, the developed system allows the user to specify such a threshold value. After defining the selected threshold value to the developed network, the data was processed and the final output results were obtained (FIG. 25). By comparing objects in FIG. 23 and results shown in FIG. 25, it can be noticed that the developed neural network was able to classify all objects, as being "Cracks" or "Else", with 100% and 92.3% accuracy, respectively.

Infiltration

The infiltration category includes several defects: sign of infiltration, sign of infiltration at the joint, water infiltration, water infiltration at the joint and mineral accumulation around the joints. They all share the same effect of having a wetted area on the wall of pipe. This wetted area is characterized by distinctive attributes, such as dark color compared to surroundings, relatively large width and length. In order to extract these distinguishing features and other attributes that will prove their contribution to the classification process, image analysis techniques were applied. Various image analysis techniques were tried, but the techniques found to yield the best results are summarized in group number 2 shown in Table B. It could be noticed that the inversion process was not applied to images depicting defects falling under the infiltration category. This is due to the reason that their color, being darker than the surroundings, creates enough contrast for further operations.

Figure 26:
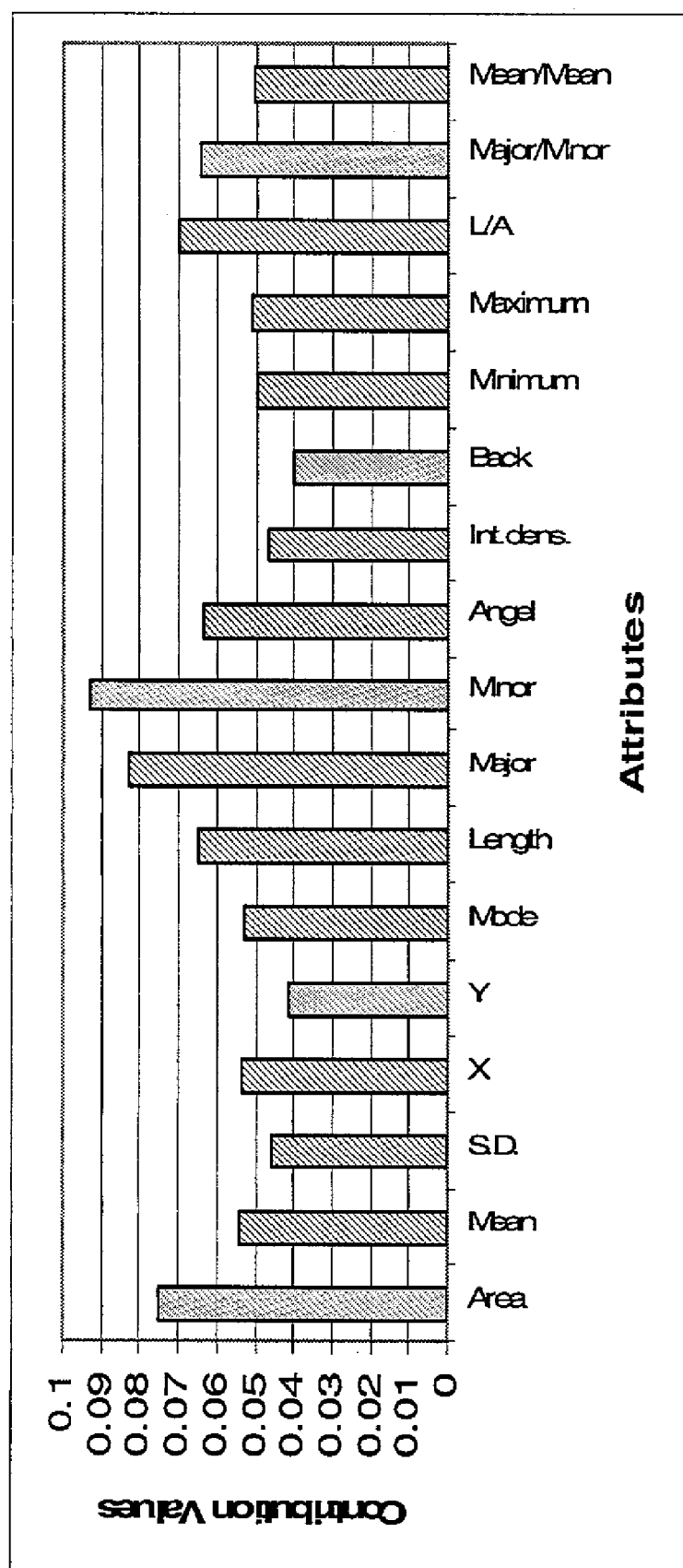
FIG. 26 shows the Contribution Values of Attributes Utilized in Designing InfiltrationNet 1.
Figure 29:
FIG. 29 is a photograph showing Thresholded Image of Infiltration.

Similar to the methodology used for the design and training of classifiers for cracks, three neural networks were developed for classification of infiltration (i.e. Infiltration-Net 1, 2 and 3). In the development of these three classifiers, a total of 868 patterns were used. The developed networks were trained to classify two categories. These categories are "Infiltration" and "Else" (i.e. non-infiltration). It should be noted that the total number of patterns was randomly divided as follows: 540 patterns (60%) for training, 174 patterns (20%) for testing and 174 patterns (20%) as a production set. The extracted features from these patterns were first utilized to develop a back-propagation neural network (i.e. InfiltrationNet 1). The results obtained from InfiltrationNet 1 are summarized in Table K. It should be noted that these results are for the 174 patterns not seen by the network during training (i.e. production set). The contribution values of attributes utilized in developing this network are shown in FIG. 26.

Although the results obtained from InfiltrationNet 1 are considered to be in the high range, an effort was made to minimize the number of attributes while keeping such high performance unchanged. This was done to reduce the processing time as much as possible. This is due to the fact that as input parameters decrease, processing time also decreases. Accordingly, two more neural networks (i.e. InfiltrationNet 2 and 3) were developed in a similar way to that discussed in Section 3.5.2. The results for the two networks are shown in Tables L and M. As can be seen from these tables a noticeable reduction in the input parameters was achieved while keeping the high performance of network #1 almost the same. The design parameters considered in developing the three networks are shown in Tables A-1 to A-3 in Appendix A.

TABLE K

Performance Results of InfiltrationNet 1

| Performance Parameters | Infiltration | Non-infiltration |
|---|---|---|
| $R^2$ | 0.8245 | 0.8245 |
| Mean squared error | 0.013 | 0.013 |
| Mean absolute error | 0.025 | 0.025 |
| Min. absolute error | 0 | 0 |
| Max. absolute error | 0.96 | 0.96 |
| Correlation coefficient (r) | .9093 | 0.9092 |
| Recognition rate | 92.8% | 100% |

TABLE L

Performance Results of InfiltrationNet 2

| Performance Criteria | Infiltration | Non-infiltration |
|---|---|---|
| $R^2$ | 0.9206 | 0.9205 |
| Mean squared error | 0.003 | 0.003 |
| Mean absolute error | 0.024 | 0.024 |
| Min. absolute error | 0 | 0 |
| Max. absolute error | 0.335 | 0.334 |
| Correlation coefficient (r) | 0.9684 | 0.9684 |
| Recognition rate | 100% | 100% |

TABLE M

Performance Results of InfiltrationNet 3

| Performance Parameters | Infiltration | Non-infiltration |
|---|---|---|
| $R^2$ | 0.9023 | 0.9022 |
| Mean squared error | 0.004 | 0.004 |
| Mean absolute error | 0.018 | 0.018 |
| Min. absolute error | 0 | 0 |
| Max. absolute error | 0.741 | 0.738 |
| Correlation coefficient (r) | .95 | 0.95 |
| Recognition rate | 100% | 99.4% |

Figure 4:
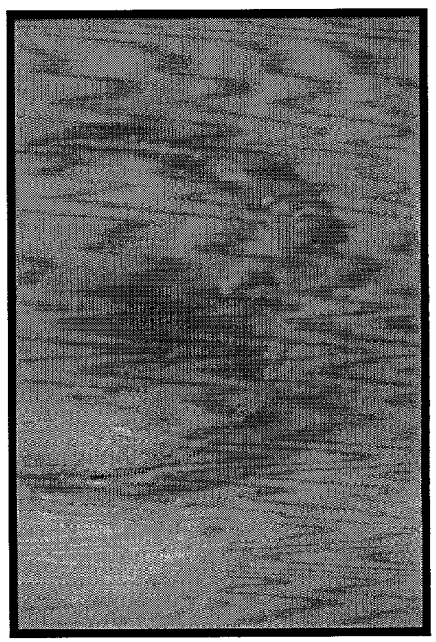
FIG. 4 is a photograph showing Infiltration.
Figure 30:
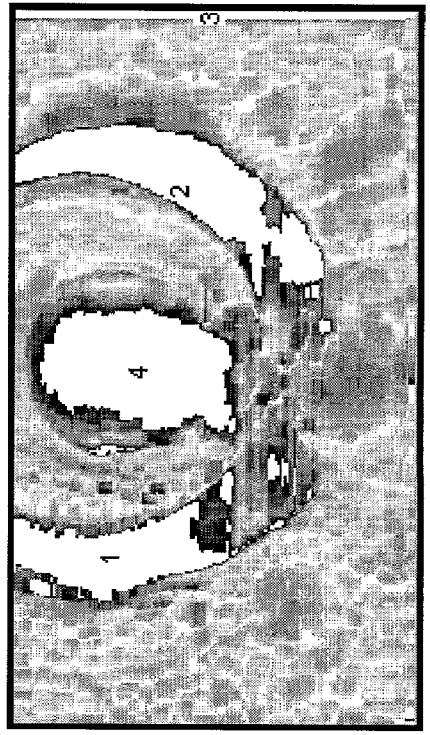
FIG. 30 is a photograph showing Segmented Image of Infiltration.
Figure 27:
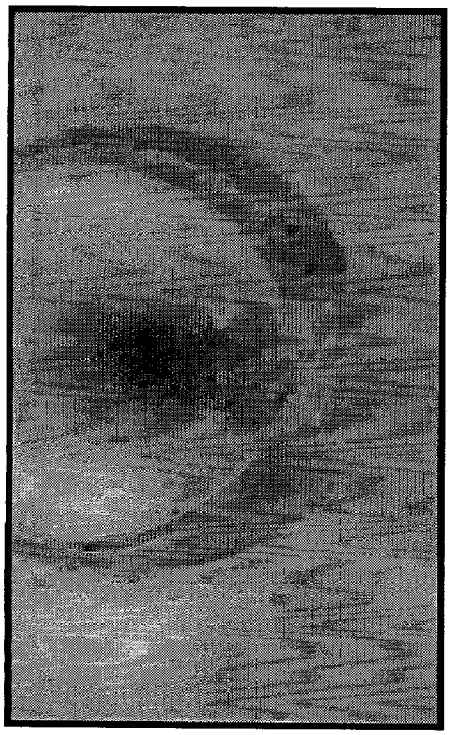
FIG. 27 is a photograph showing Dilated Image of Infiltration.
Figure 28:
FIG. 28 is a photograph showing Background subtracted Image of Infiltration.
Figure 31:
FIG. 31 shows the Analysis Results of an Image Depicting Infiltration.
Figure 32:
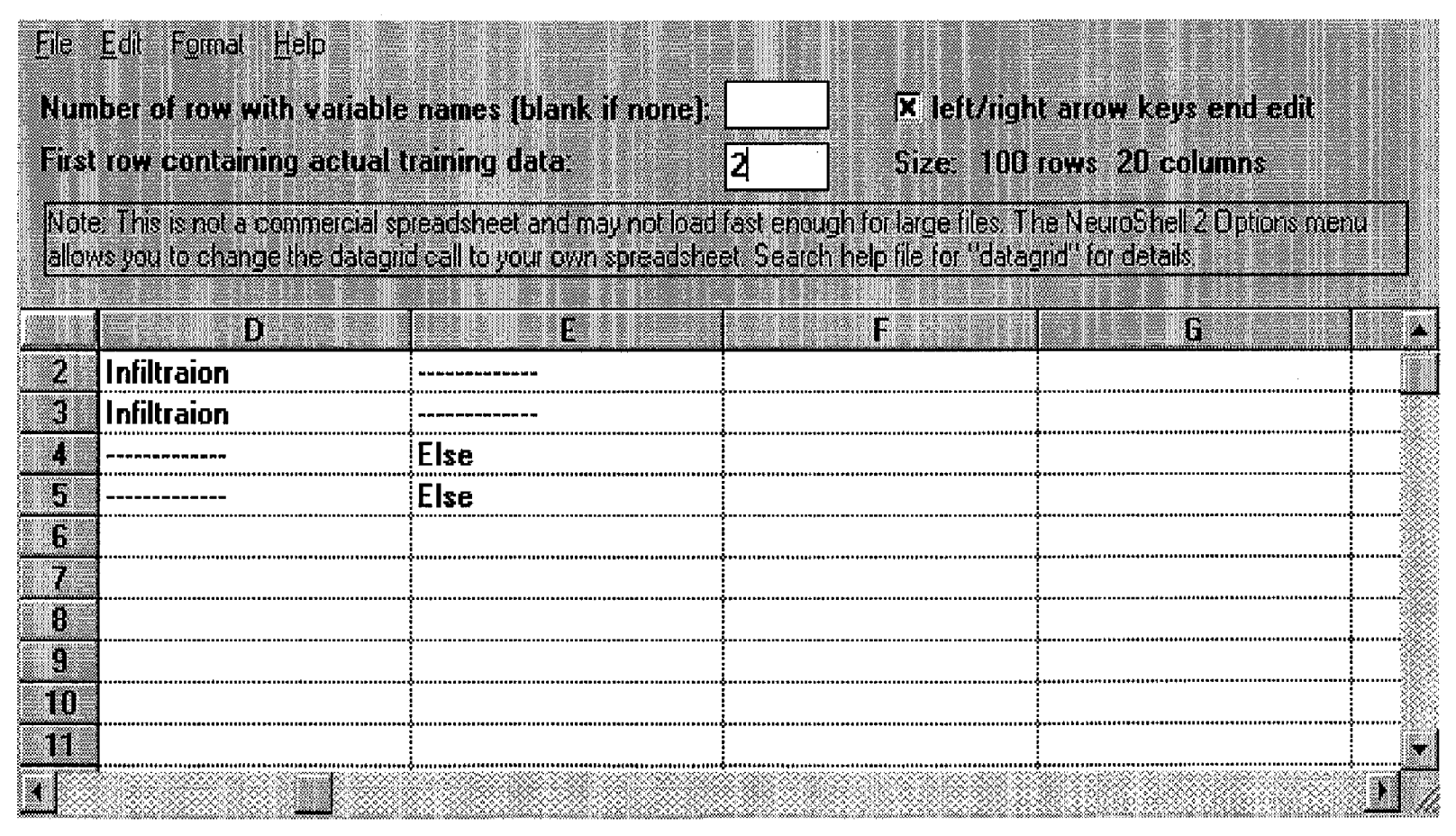

To demonstrate the use and capabilities of the developed neural networks in this category, the image shown in FIG. 4 was considered. As can be noticed form this figure, the image depicts infiltration. To detect and classify this defect, the image was processed following the sequence of operations summarized in Table B. The results of this process are shown in FIGS. 27 to 30. As can be seen in FIG. 30, the image depicts four objects. Objects number 1 and 2 are infiltration, while objects number 3 and 4 are not. The attributes of these objects, which are shown in FIG. 31, were then fed into the already trained neural networks for classification. A sample of obtained results are shown in FIG. 32. It should be noted that a threshold value of 50% was considered for positive classification.

Deposits

The deposits category includes all materials that buildup on the bottom of a pipe. Regardless of their source being organic or non-organic, they all share one common feature: their location. Their location is at the invert level of pipes (i.e. bottom of pipe). In order to extract this distinguishing feature and other features that will prove their contributions to the classification process, image analysis techniques were applied.

Various image analysis techniques were analyzed and tried to enhance images of defects in order to isolate deposits from their background. The techniques found to yield the best results are detailed in group number 1 shown in Table B. These techniques were applied on all collected images that showed defects within the deposits group. Based on the extracted features obtained from the analysis of collected images, it was noticed that deposits might share some attributes with other defects such as cross-sectional reductions. These attributes are large minor axis length, relatively large area and small ratio of major axis length to minor axis length. The only factors that differentiate between the apparently similar attributes are the X and Y coordinates (i.e. location). It was noticed also from the collected sample of video images that the location of cross-sectional reductions is in the central area of the pipe. This is in contrast to the location of deposits, which are at the bottom of the pipe. These observations have been utilized to facilitate the classification process by assigning the coordinates of objects located at the bottom of pipe to (2, 2).

Using a set of 760 patterns, a set of three neural networks was developed to classify deposits (i.e. DepositNet 1, 2 and 3). This was carried out following the same methodology described in the two previous sections (Sections 3.5.2 and 3.5.3). The developed networks were trained to classify two categories: "Deposits" and "Else" (i.e. Non deposits). It should be noted that the total number of patterns was randomly divided as follows: 456 patterns (60%) for training, 152 patterns (20%) for testing and 152 patterns (20%) as a production set. It should also be noted that the training algorithm was set to save the trained network at the best test set and limit the calibration interval to 50 to prevent and monitor over-training.

Figure 33:
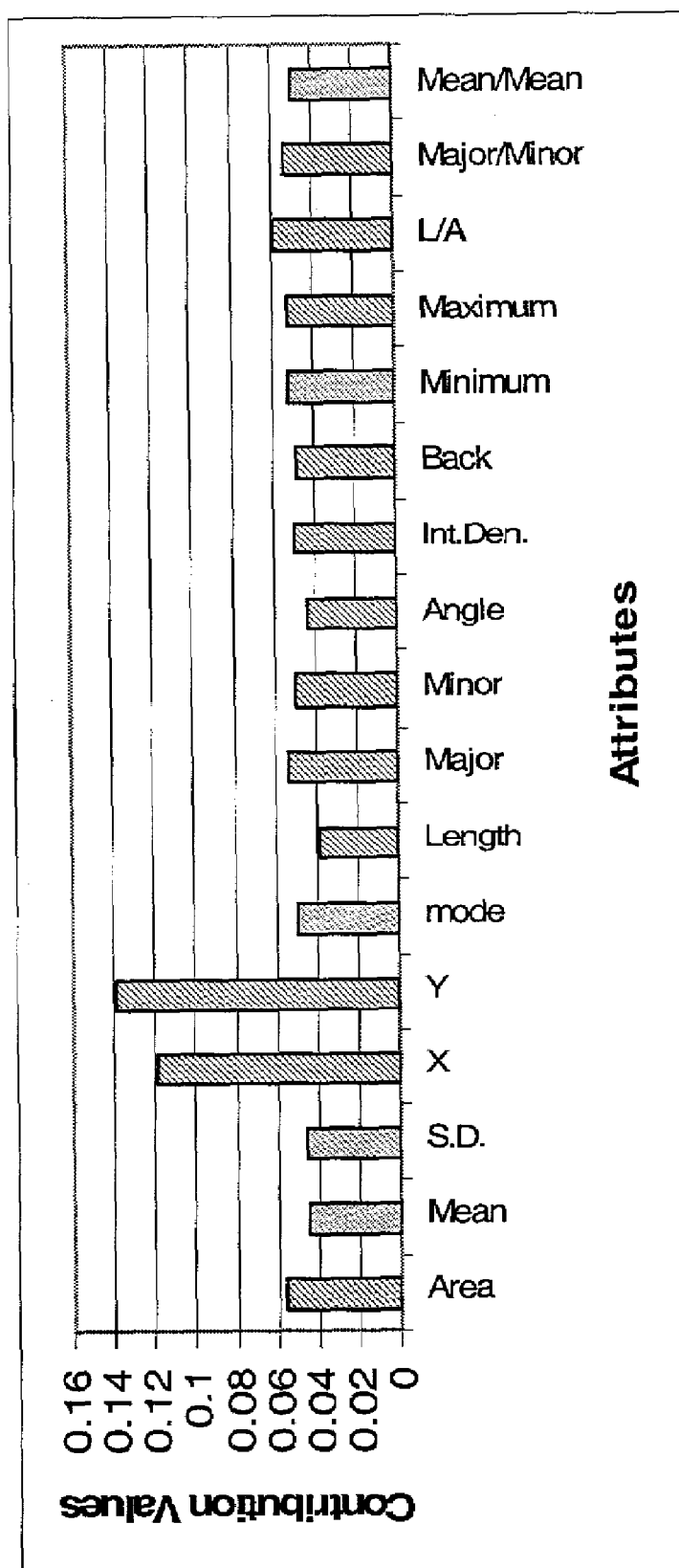
FIG. 33 shows the Contribution Values of Attributes Utilized in Designing DepositNet 1.
Figure 35:
FIG. 35 is a photograph showing Background Subtracted Image of Deposits.
Figure 37:
FIG. 37 is a photograph showing Thresholded Image of Deposits.
Figure 34:
FIG. 34 is a photograph showing Inverted Image of Deposits.
Figure 36:
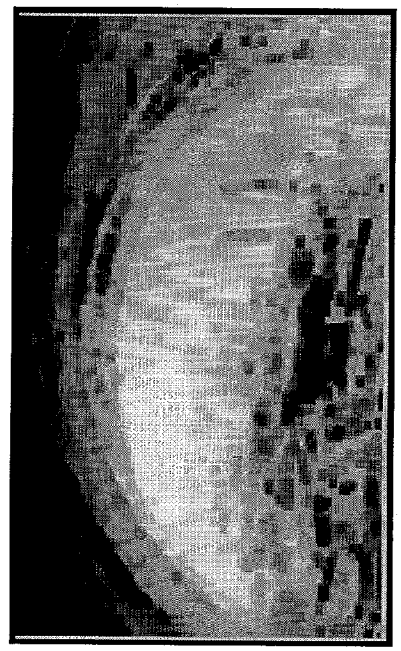
FIG. 36 is a photograph showing Dilated Image of Deposits.
Figure 38:
FIG. 38 is a photograph showing Segmented Image of Deposits.

In developing DepositNet 1, various combinations of hidden neurons, activation and scaling functions were tried and the near optimum design was found to be 17 neurons in the input layer, 40 neurons in the hidden layer and 2 neurons in the output layer. The results obtained using this developed network are shown in Table N. It should be noted that these results are for the 152 patterns not seen by the network during training (i.e. production set). The contribution values of all attributes utilized in developing this network are shown in FIG. 33.

Although the results obtained from DepositNet 1 are in the high range, an effort was made to minimize the number of attributes while keeping such high performance unchanged. This was done to reduce the processing time as much as possible. Accordingly, two more neural networks were developed (i.e. DepositNet 2 and 3). The results for these two networks are shown in Tables O and P. It should be noted that these results are for the 152 patterns that were not presented to the network while training (i.e. the production set). As can be seen from Tables O and P, a noticeable reduction in the input parameters was achieved while keeping the high performance almost the same. The design parameters considered in developing the three networks are listed in Tables A-4 to A-6 in Appendix A.

TABLE N

Performance Results of DepositNet 1

| Performance Criteria | Non-Deposits | Deposits |
|---|---|---|
| $R^2$ | 0.9912 | 0.9915 |
| Mean squared error | 0.0 | 0.0 |
| Mean absolute error | 0.005 | 0.005 |
| Min. absolute error | 0 | 0 |
| Max. absolute error | 0.106 | 0.112 |
| Correlation coefficient (r) | 0.9985 | 0.9988 |
| Recognition rate | 100% | 100% |

TABLE O

Performance Results of DepositNet 2

| Performance Criteria | Non-Deposits | Deposits |
| --- | --- | --- |
| $R^2$ | 0.9981 | 0.9983 |
| Mean squared error | 0.0 | 0.0 |
| Mean absolute error | 0.002 | 0.002 |
| Min. absolute error | 0 | 0 |
| Max. absolute error | 0.050 | 0.046 |
| Correlation coefficient (r) | 0.9999 | 0.9999 |
| Recognition rate | 100% | 100% |

TABLE P

Performance Results of DepositNet 3

| Performance Criteria | Non-deposits | Deposits |
| --- | --- | --- |
| $R^2$ | 0.9903 | 0.9854 |
| Mean squared error | 0.0 | 0.0 |
| Mean absolute error | 0.002 | 0.002 |
| Min. absolute error | 0 | 0 |
| Max. absolute error | 0.166 | 0.204 |
| Correlation coefficient (r) | 0.9952 | 0.9928 |
| Recognition rate | 100% | 100% |

Figure 3:
FIG. 3 is a photograph showing Dirt Deposits.
Figure 39:
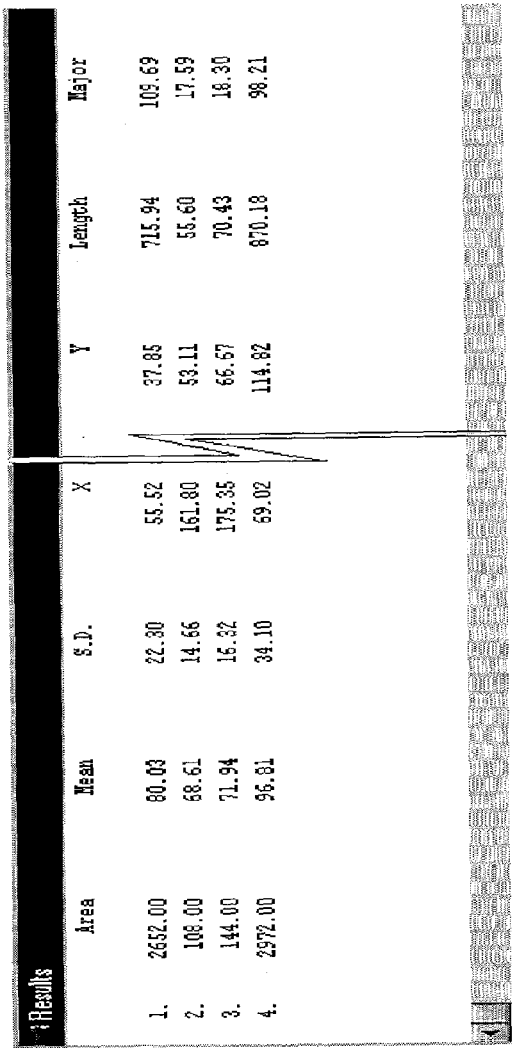
FIG. 39 shows the Analysis Results of an Image Depicting Deposits.
Figure 40:
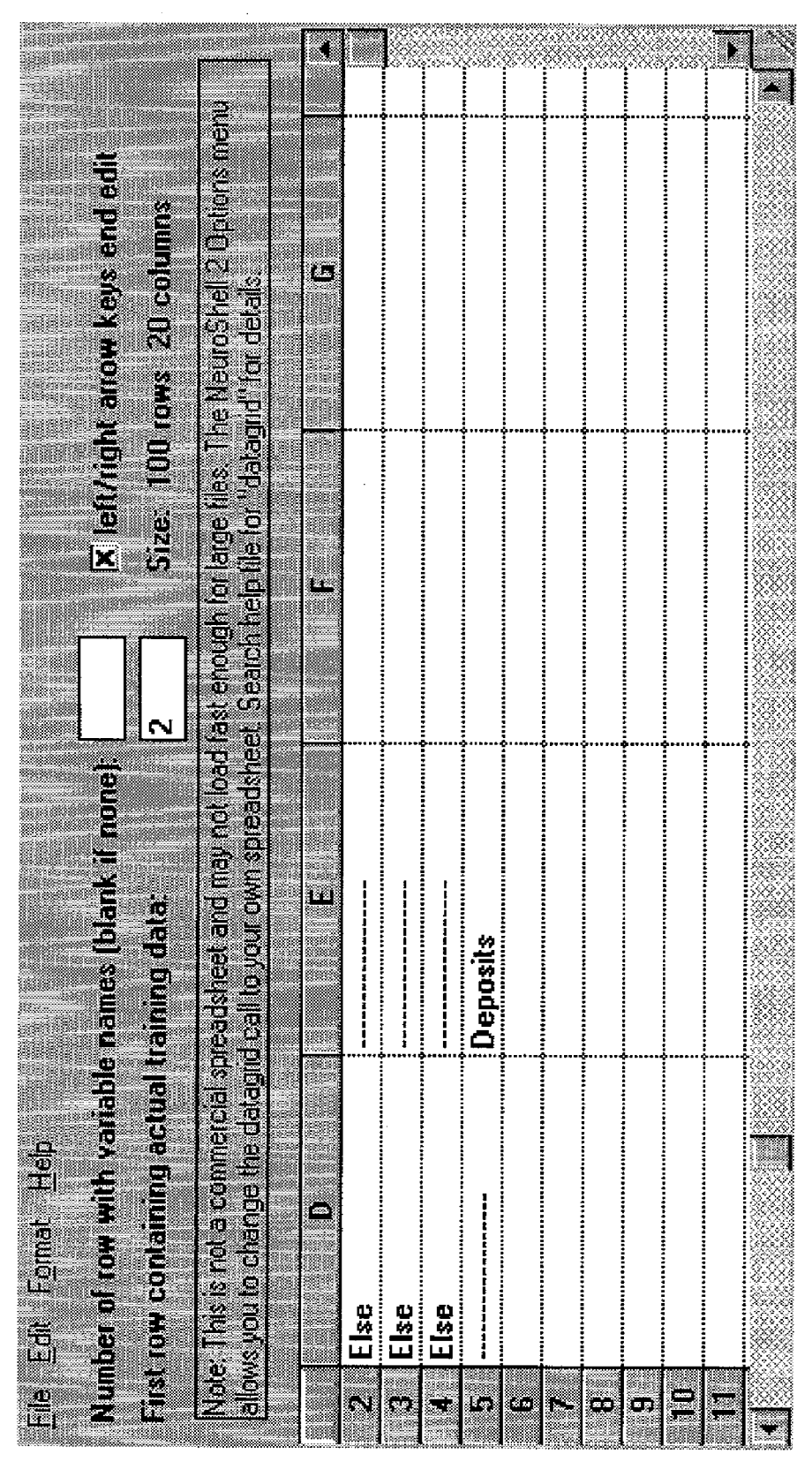

To demonstrate the use and capabilities of the developed neural networks, the image shown in FIG. 3 was considered. As can be seen, the image depicts a number of objects. These Objects are deposits and a number of non-defects. To detect and classify these objects, the image was processed in the same manner as explained earlier. The results of this process are shown in FIGS. 34 to 38. The extracted feature vectors shown in FIG. 39 were then fed into the already trained neural networks for classification. The results obtained from a sample network are shown in FIG. 40. It should be noted that a threshold value of 50% was considered for positive classification.

Cross-sectional Reductions

The cross-sectional reductions category includes all materials that obstruct flow in pipes. Regardless of their nature, roots or buildup of deposits, they all share a common feature: location. Their location is at the central area of pipes. To detect and classify this particular type of defect, similar techniques to those utilized in detecting and classifying deposits were utilized (i.e. sequence #1 in Table B).

A sample of 273 cross-sectional reductions and non-cross-sectional reductions was analyzed. Based on the extracted feature vectors from this analysis, it was noticed that cross-sectional reductions might have similar attributes to those obtained from other types of defects such as deposits. This is due to the difference in distance between the CCTV camera and each type of defects. The only factors that differentiate between the apparently similar attributes are the x and y coordinates (i.e. location). It was noticed from the collected sample of video images that the center of an image is always darker than its surrounding areas. This is due to the fact that the lighting effect vanishes as the distance from the lighting source gets greater. It was also noticed that cross-sectional deductions tend to be illuminated at this specific area (the center of an image). This is due to the fact that these defects tend to project from the surface of the pipe and reflect back the beam of light they are exposed to. These observations have been utilized to facilitate the classification process by assigning the coordinates of objects located in center of images to (1, 1).

Figure 41:
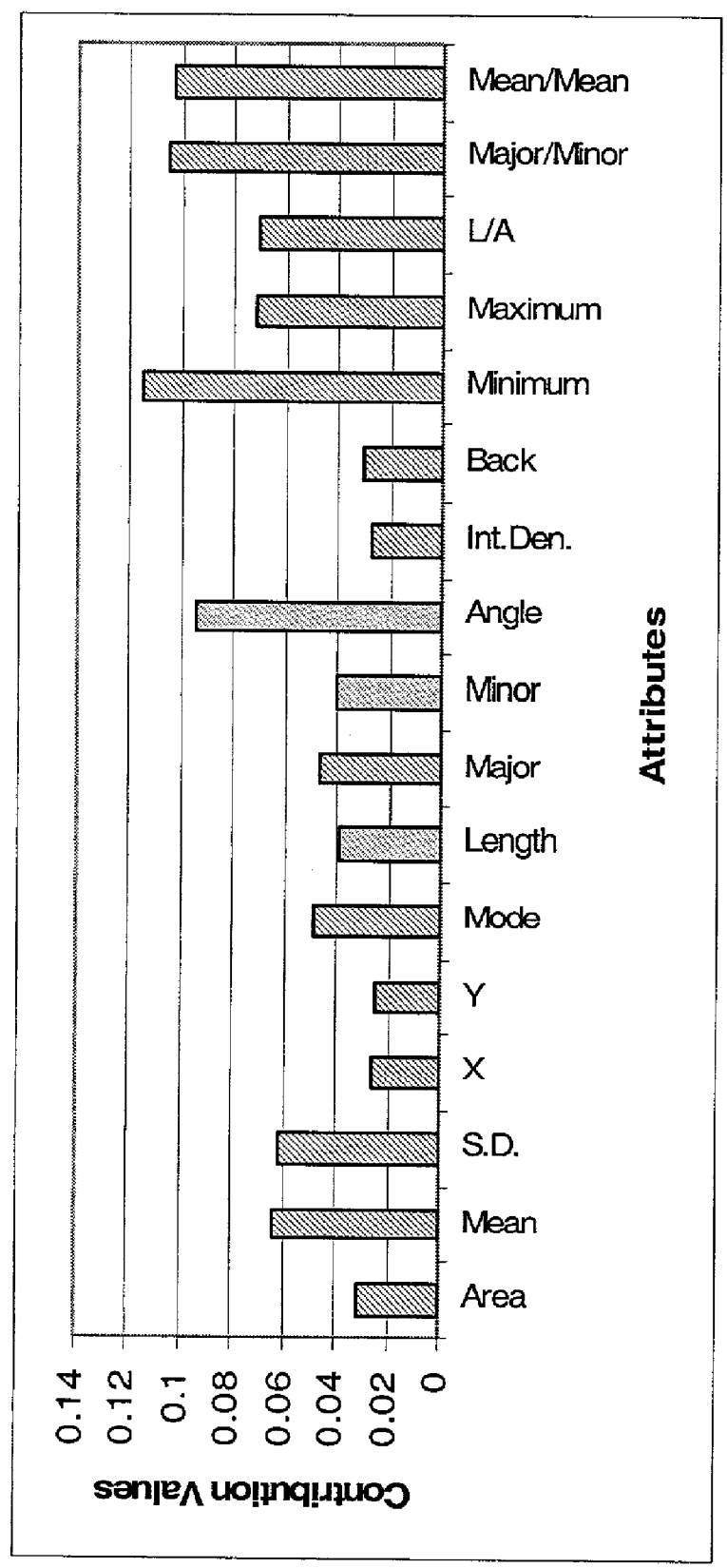
FIG. 41 shows the Contribution Values for all Attributes Utilized in Designing a Preliminary Neural Network for Classification of Cross-sectional Reductions.
Figure 43:
FIG. 43 is a photograph showing Dilated Image of cross-sectional Reductions.
Figure 45:
FIG. 45 is a photograph showing Thresholded Image of Cross-sectional Reductions.
Figure 42:
FIG. 42 is a photograph showing Inverted Image of cross-sectional Reductions.
Figure 44:
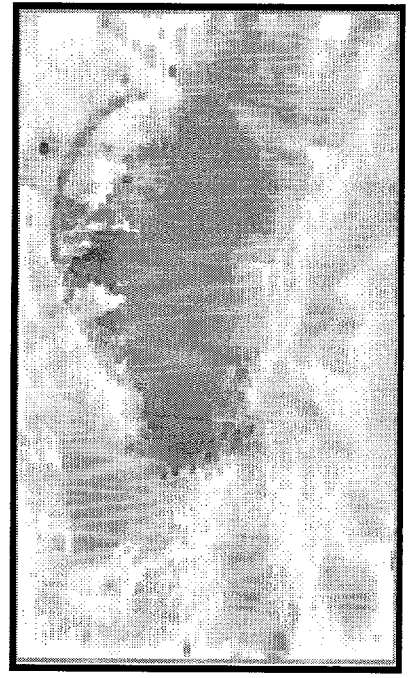
FIG. 44 is a photograph showing Background subtracted Image of Cross-sectional Reductions.
Figure 46:
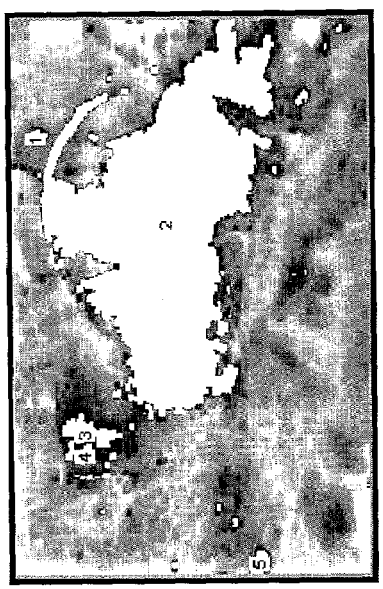
FIG. 46 is a photograph showing Segmented Image of Cross-sectional Reductions.
Figure 47:
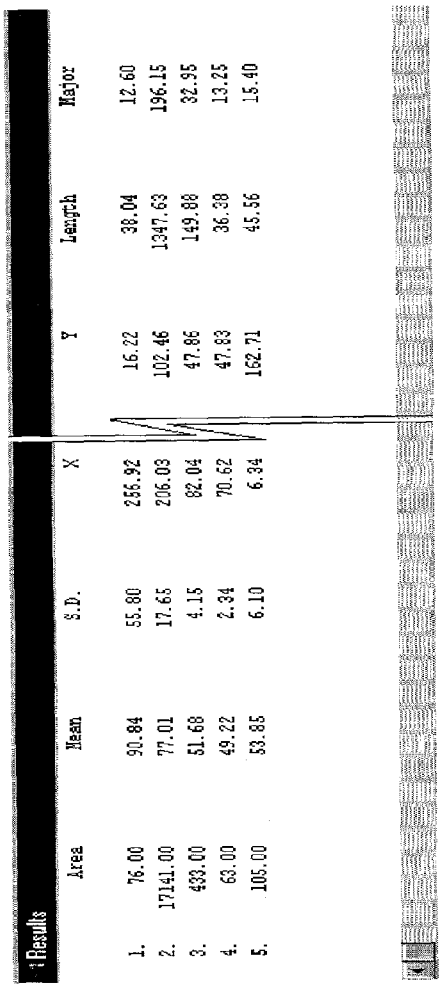
FIG. 47 shows the Analysis Results of an Image Depicting Cross-sectional Reductions.

The results obtained from the analysis conducted on the collected images were utilized to develop a back-propagation neural network. The developed network was trained to classify two categories: "Cross-sectional reduction" and "Else" (i.e. Non-cross-sectional reductions). The results obtained using this developed network are shown in Table Q. It should be noted that these results are for the 54 patterns not seen by the network during training (i.e. production set). The contribution values of attributes utilized in developing this network are shown in FIG. 41.

In an effort to improve the performance of this developed network, three neural networks were developed in a similar method to that explained in Section 3.5.2 (i.e.

CrossNet 1, 2 and 3). The results of these networks are shown in Tables R, S and T. It should be noted that these results are based on the production set. The final design parameters considered in designing these networks are listed in Tables A-7 to A-10 in Appendix A.

TABLE Q

Performance Results of a Preliminary Neural Network for Classification of Cross-Sections Reductions

| Performance Criteria | Cross-sectional reduction | Non-cross-sectional reductions |
| --- | --- | --- |
| $R^2$ | 0.8319 | 0.8288 |
| Mean squared error | 0.023 | 0.024 |
| Mean absolute error | 0.053 | 0.053 |
| Min. absolute error | 0 | 0 |
| Max. absolute error | 0.808 | 0.824 |
| Correlation coefficient (r) | 0.9125 | 0.9107 |
| Recognition rate | 88% | 97.8% |

TABLE R

Performance Results of CrossNet 1

| Performance Criteria | Cross-sectional reductions | Non-cross-sectional reductions |
| --- | --- | --- |
| $R^2$ | 0.8203 | 0.8257 |
| Mean squared error | 0.025 | 0.024 |
| Mean absolute error | 0.058 | 0.052 |
| Min. absolute error | 0 | 0 |
| Max. absolute error | 0.826 | 0.823 |
| Correlation coefficient (r) | 0.9064 | 0.9096 |
| Recognition rate | 88% | 100% |

TABLE S

Performance Results of CrossNet 2

| Performance Criteria | Cross-sectional reductions | Non-cross-sectional reductions |
| --- | --- | --- |
| $R^2$ | 0.8679 | 0.8600 |
| Mean squared error | 0.020 | 0.021 |
| Mean absolute error | 0.072 | 0.075 |
| Min. absolute error | 0 | 0 |
| Max. absolute error | 0.614 | 0.621 |
| Correlation coefficient (r) | 0.9375 | 0.9375 |
| Recognition rate | 90% | 94% |

TABLE T

Performance Results of CrossNet 3

| Performance Criteria | Cross-sectional reductions | Non-cross-sectional reductions |
|---|---|---|
| $R^2$ | 0.9072 | 0.9091 |
| Mean squared error | 0.013 | 0.013 |
| Mean absolute error | 0.049 | 0.049 |
| Min. absolute error | 0 | 0 |
| Max. absolute error | 0.640 | 0.626 |
| Correlation coefficient (r) | 0.9553 | 0.9564 |
| Recognition rate | 88% | 100% |

Figure 2:
FIG. 2 is a photograph showing Root Intrusion.
Figure 48:
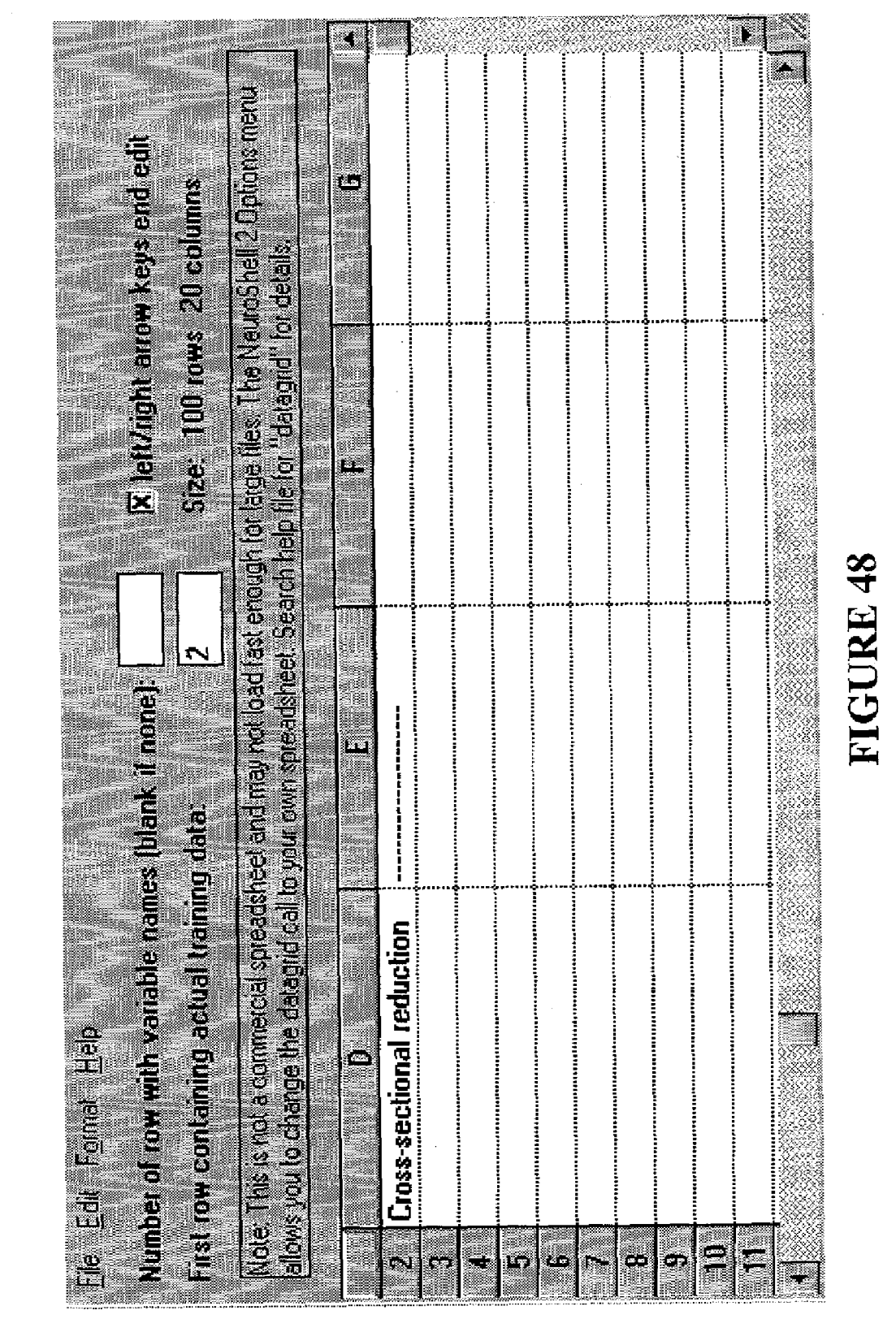

To demonstrate the use and capabilities of the developed neural networks, the image shown in FIG. 2 was considered. As can be seen, the image depicts a cross-sectional reduction in a form of roots. To detect and classify this defect, the image was processed as shown in FIGS. 42 to 47. As can be noticed, the segmented image depicts five objects. Object number 2 is a root intrusion, while objects 1, 3, 4 and 5 are not. Based on location, all objects were assigned (0, 0) and (1, 1) for their X and Y coordinates. These objects with (1, 1) (i.e. located inside the central area of pipe) were then fed into the already trained neural networks for classification. The results of classification for a sample network are shown in FIG. 48.

Misalignments

The misalignment category includes several defects. These defects are offset joint over 3 cm, open joint over 5 cm, opposite slope, visible soil, sagging pipes, right lateral deviation, left lateral deviation and visible rubber gasket at the joint. They all share the same effect of having a crescent shape at the joints. This crescent shape is characterized by distinctive attributes, such as relatively small area and bright color. In order to extract this distinguishing features and other features that will prove their contributions to the classification process, image analysis techniques were applied. These image analysis techniques are the same as those utilized in detecting and classifying deposits and cross-sectional reductions (i.e. sequence #1 in Table B).

A sample of 275 patterns was analyzed and their feature vectors were extracted. Based on this analysis, it was noticed that misalignments might have similar attributes to those obtained from other defects such as cracks. This is due to the difference in distance between the CCTV camera and each type of defect. In other words, misalignments away from the camera tend to have similar attributes to cracks closer to the camera. Those similar attributes are small minor axis length, small area and large ratio of major axis length to minor axis length. The only factors that differentiate between the apparently similar attributes are the x and y coordinates (i.e. location). For example, it was noticed from the collected sample of video images that the center of an image is always darker than its surrounding areas. As has been explained earlier in the case of cross-sectional reductions, misalignments are also illuminated at this specific area of pipes. This is due to the reason that these two objects are projected from the surface of pipes, and they both reflect back the beam of light they are exposed to. Other defects such as cracks do not exhibit the same phenomena. This was utilized to facilitate the classification process by assigning the coordinates of objects located in this dark spot to (1, 1).

The collected sample of video images was then utilized to develop a back-propagation neural network. The developed network was trained to classify two categories: "Misalignments" and "Else". The results obtained using the developed network are shown in Table U. It should be noted that these results are for the 55 patterns not seen by the network during training (i.e. production set). The contribution of each attribute is shown in FIG. 49. In an effort to improve the performance of this network, three neural networks were developed in a similar way to that explained in Section 3.5.2 (i.e. MisalignmentNet 1, 2 and 3). The results obtained from these networks are shown in Tables V, W and X. It should be noted that these results are based on the production set. The final design parameters considered in designing and developing these networks are listed in Tables A-11 to A-14 in Appendix A.

TABLE U

Performance Results of a Preliminary Neural Network for Classification of Misalignments

| Performance Criteria | Misalignments | Non-misalignments |
|---|---|---|
| $R^2$ | 0.8319 | 0.8288 |
| Mean squared error | 0.023 | 0.024 |
| Mean absolute error | 0.053 | 0.053 |
| Min. absolute error | 0 | 0 |
| Max. absolute error | 0.808 | 0.824 |
| Correlation coefficient (r) | 0.9125 | 0.9107 |
| Recognition rate | 88% | 97.8% |

TABLE V

Performance Results of MisalignmentNet 1

| Performance Criteria | Misalignments | Non-misalignments |
|---|---|---|
| $R^2$ | 0.8776 | 0.8823 |
| Mean squared error | 0.018 | 0.018 |
| Mean absolute error | 0.051 | 0.053 |
| Min. absolute error | 0 | 0 |
| Max. absolute error | 0.599 | 0.574 |
| Correlation coefficient (r) | 0.9378 | 0.9405 |
| Recognition rate | 90% | 97.8% |

TABLE W

Performance Results of MisalignmentNet 2

| Performance Criteria | Misalignments | Non-misalignments |
|---|---|---|
| $R^2$ | 0.9458 | 0.9484 |
| Mean squared error | 0.008 | 0.008 |
| Mean absolute error | 0.031 | 0.030 |
| Min. absolute error | 0 | 0 |
| Max. absolute error | 0.430 | 0.421 |
| Correlation coefficient (r) | 0.9749 | 0.9761 |
| Recognition rate | 100% | 100% |

TABLE X

Performance Results of MisalignmentNet 3

| Performance Criteria | Misalignments | Non-misalignments |
|---|---|---|
| $R^2$ | 0.8514 | 0.8550 |
| Mean squared error | 0.022 | 0.022 |
| Mean absolute error | 0.059 | 0.058 |
| Min. absolute error | 0 | 0 |
| Max. absolute error | 0.767 | 0.758 |
| Correlation coefficient (r) | 0.9254 | 0.9272 |
| Recognition rate | 100% | 97.8% |

Figure 6:
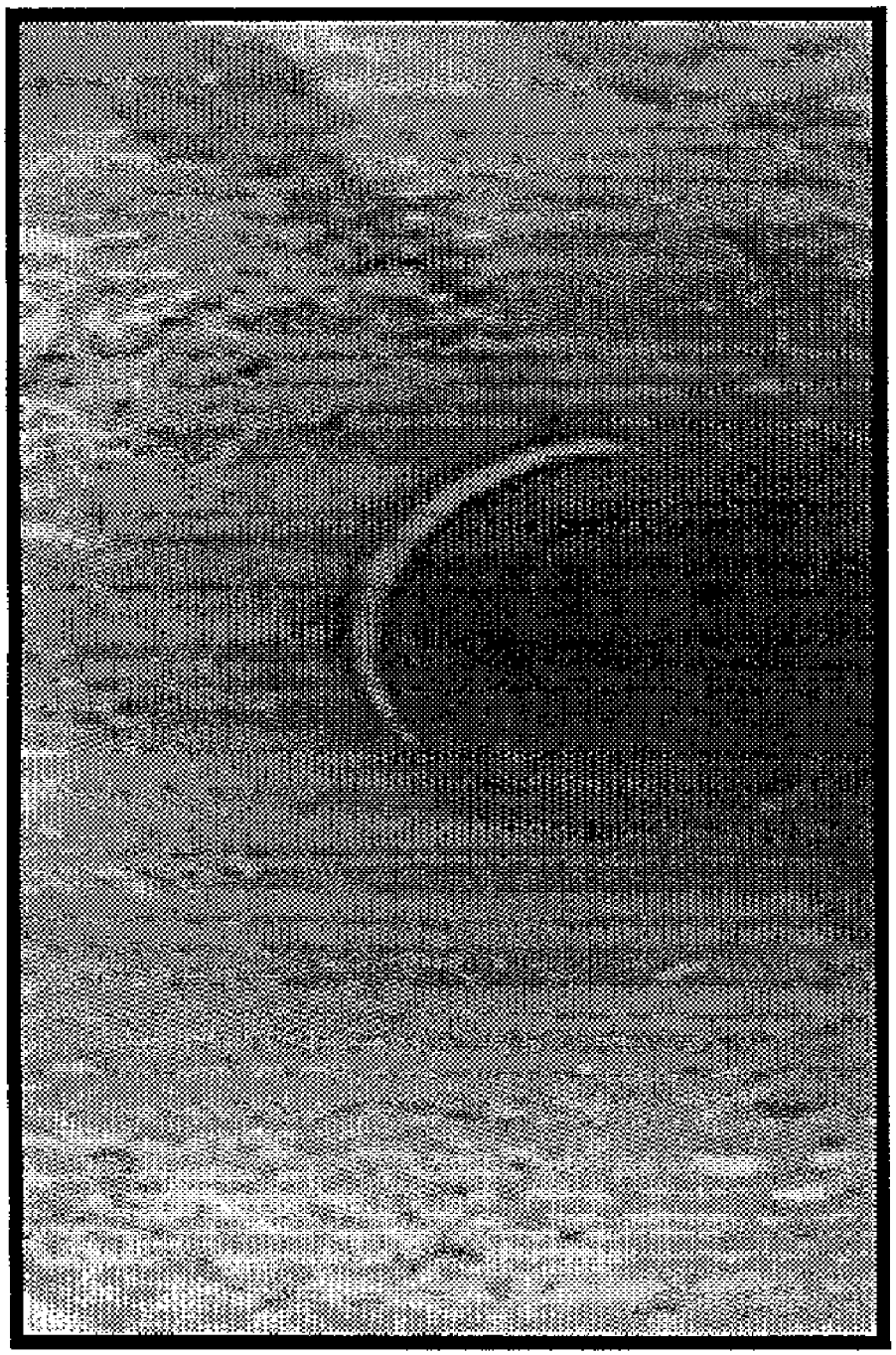
FIG. 6 is a photograph showing Misalignments.

To demonstrate the use and capabilities of the developed neural networks, the image shown in FIG. 6 was considered. As can be seen, the image depicts a number of objects. These objects are misalignments and non-misalignments. To detect and classify these objects, the image was processed in the same manner as was shown in FIGS. 50 to 55. As can be noticed, the segmented image depicts 22 objects. Object number 10 is a misalignment, while other objects are not. Based on location, all objects were assigned (0, 0) and (1, 1) for their X and Y coordinates. Objects with (1, 1) were then fed into the already trained neural networks for classification. The results of classification for a sample network are shown in FIG. 56.

Example Application on the Multiple Classifier System and Solution Strategy

To demonstrate the use and capabilities of the proposed multiple classifier system and solution strategy, images shown in FIG. 2 to 6 were considered. As can be seen cross-sectional reductions in a form of roots, deposits, infiltration, cracks and misalignments are depicted in FIGS. 2, 3, 4, 5 and 6, respectively. To classify these defects, the images were processed three times. In the first pass, the images were processed by sequence of operation number 1 shown in Table B. The purpose of this pass is to detect and classify deposits, cross-sectional reductions and misalignments. The segmented images of these images are shown in FIGS. 57 to 61 below. As can be noticed from FIGS. 57, 58, 59, 60 and 61, 4, 22, 5, 14 and 6 objects were detected, respectively. The extracted features of the images were processed using DepositNet 1, DepositNet 2 and DepositNet 3. The results of these networks are shown in FIGS. 62 to 64. As can be noticed, all developed networks were able to classify "Deposits" and "Else" with 100% accuracy. The multiple classifier system was then applied to counter-check the results obtained from the different neural networks. The results obtained from the multiple classifier system are shown in FIG. 65. As shown in FIG. 65, the overall performance of the system, with respect to "Deposits" and "Else", is concluded to be 100% for the considered sample of patterns.

All non-deposits were then segregated based on their locations. Those with (1, 1) coordinates were fed into CrossNet 1, CrossNet 2 and CrossNet 3 for classification of cross-sectional reductions. The results of these networks are shown in FIGS. 66 to 68. As can be noticed, CrossNet 1 was able to classify "Cross-sectional reductions" and "Else" with 100% and 0% accuracy, respectively. On the other hand, CrossNet 2 and CrossNet 3 classified both categories with 100% accuracy. To counter-check the results obtained from the different neural networks, the multiple classifier system was applied (FIG. 69). As shown in FIG. 69, the overall classification performance of the system is concluded to be 100% for "Cross-sectional reduction" and "Else". This is due to the fact that the misclassification that was reported by CrossNet 1 was confirmed by neither CrossNet 2 nor CrossNet 3.

Further, the same file (i.e. those defects with (1, 1) coordinates) was also fed into MisalignmentNet 1, MisalignmentNet 2 and MisalignmentNet 3. The purpose of this step is to classify misalignments. The results of this process are shown in FIGS. 70 to 72. As can be noticed, MisalignmentNet 1 was able to classify "Misalignment" and "Else" with 100% and 0% accuracy, respectively. On the other hand, MisalignmentNet 2 and MisalignmentNet 3 classified both categories with 100% accuracy. By considering the results shown in FIG. 73, the overall classification performance of the system is concluded to be 100% for "Misalignment" and "Else". This is due to the fact that the misclassification that was reported by MisalignmentNet 1 was confirmed by neither MisalignmentNet 2 nor MisalignmentNet 3.

To detect and classify infiltration, the images were processed using sequence of operations number 2 rather than number 1 used in the first pass (Table B). The segmented images are shown in FIGS. 74 to 78 below. As can be noticed from FIGS. 74, 75, 76, 77 and 78, 6, 7, 7, 3 and 4 objects were detected, respectively. The extracted features of these images were then processed using InfiltrationNet 1. The results of this network are shown in FIG. 79. By comparing objects in FIGS. 74 to 78 and results shown in FIG. 79, it can be noticed that the developed neural network was able to classify "Infiltration" and "Else" 100% and 96% accuracy, respectively.

The same process was repeated utilizing InfiltrationNet 2 and InfiltrationNet 3 networks. The outputs of these two networks are shown in FIGS. 80 to 81. As can be noticed from FIG. 80, InfiltrationNet 2 was able to classify "Infiltration" and "Else" with 100% and 92% accuracy, respectively. On the other hand, InfiltrationNet 3 was able to classify the same categories with 100% and 96% accuracy, respectively (FIG. 81). By considering the results obtained from the three classifiers, it can be concluded that the overall performance of the system is 100% for "Infiltration" and 100% for "Else" categories, respectively. This is due to the fact that no object was misclassified by more than one neural network (FIG. 82).

To detect and classify cracks, the images were processed for the third time. In this pass, the images were processed by applying sequence of operations number 3 (Table B). The segmented images of these images are shown in FIGS. 83 to 87 below. As can be noticed from FIG. 83, 84, 85, 86 and 87, 15, 4, 2, 2 and 9 objects were detected, respectively. The extracted features of these images were then fed into CrackNet 1. The results of this neural network are shown in FIG. 88. By comparing objects in FIGS. 83 to 87 and results shown in FIG. 88, it can be noticed that the developed neural network was able to classify "Cracks" and "Else" 100% and 93.3% accuracy, respectively.

The same process was repeated utilizing CrackNet 2 and CrackNet 3 neural networks. The outputs of these two networks are shown in FIGS. 89 and 90. As can be noticed from FIG. 89, CrackNet 2 was able to classify "Cracks" and "Else" with 100% and 90% accuracy, respectively. On the other hand, CrackNet 3 was able to classify the same categories with 100% and 96% accuracy, respectively (FIG. 90). By considering the results obtained from the three classifiers, it can be concluded that the overall performance of the system is 100% for "Crack" and 93.3% for "Else" categories, respectively (FIG. 91).

A typical rehabilitation process of underground sewer pipes usually starts by collecting information about the project requirements and constraints (i.e. diameter, type of defect and cost). This set of information is then processed to select the most suitable rehabilitation method(s) that satisfy the project and the decision-maker's requirements. As discussed in Chapter 1, currently, this selection process is done utilizing the decision-maker's experience without computer assisted tools. Due to the rapidly expanding field of sewer rehabilitation, selection in this manner may suffer from the limited knowledge and/or experience of the decision-maker and could result in overlooking technically feasible and cost effective methods.

This chapter describes a developed system for selecting the most suitable rehabilitation technique(s) for those defects recognized by the automated inspection system (Shehab-Eldeen and Moselhi 2000 & 2001). The system can assist municipal engineers and contractors in selecting the most suitable trenchless rehabilitation technique that satisfies job conditions and user's requirements. The system is also believed to help new and less experienced engineers to benefit from the experience gained by others. In this rehabilitation system, the user is required to input a set of information that describes the project and user's requirements. Based on this input data, the system utilizes two modules, namely database management system (DBMS) and decision support system (DSS), to select the product(s) and method(s), along with their supplier(s), that satisfy the project and user's requirements.

Rehabilitation of sewer pipes poses a major challenge to most municipalities. This challenge is demonstrated by two main tasks. The first is to satisfy all constraints that are imposed by specific job conditions and/or user requirements, and the second is to select the most suitable rehabilitation technique that satisfies those constraints. Various rehabilitation techniques are available in the market, each is considered suitable for certain job/user requirements. To recommend a suitable rehabilitation technique, it is necessary to consider all contributing attributes that help in performing the selection process. Given the availability of large number of rehabilitation techniques and their associated contributing attributes, the importance of developing a system that eases the challenging task of selecting a suitable rehabilitation technique for specific job conditions and/or user requirements can not be overemphasized.

To assist municipality engineers in carrying out this challenging task, an automated rehabilitation system has been developed. The system consists of two main modules, a DBMS and a DSS, developed in Microsoft Access and Visual Basic environments, respectively. FIG. 92 depicts the main modules of the developed system. As depicted in FIG. 92, the selection process of a suitable rehabilitation technique starts by feeding the system with a report on the status of defects. If the report indicates no sign of defects, then the rehabilitation system will not be executed and a report will be issued accordingly. Otherwise the user will be required to input necessary information, such as pipe diameter and degree of bends, to activate the DBMS module. Upon processing the input data by the DBMS, the system will suggest a suitable method for rehabilitation. If the system suggests one method only, then a report will be issued accordingly. But, if more than one method is suggested, then the DSS module will be activated to rank all suggested methods based on multi-attributed criteria. The following sections describe each module.

Database Management System (DBMS)

Developing a database encompasses the utilization of database management systems (DBMS) to support the process of defining, constructing and manipulating data (Elmasri and Navathe 1994). Defining a database involves specifying the data types and their associated constraints (i.e. text, number and format). Constructing a database is the process of building a conceptual model showing all entities and attributes, transferring this conceptual model to a physical one (i.e. tables and relationships) and populating the database tables with all required information, and defining relationships among them. Manipulating a database includes designing and building a supporting search system (i.e. query) that retrieves specific information based on user needs. There are different database models, of which the relational model is the most commonly used in engineering applications (Udo-Inyang and Chen 1997 and Johnson 1997). This model was utilized to design and build the database of the rehabilitation system. In this model, the data are organized in tables. These tables are related to each other by different types of relationships such as one-many, many-one and many-many.

Various rehabilitation techniques are available in the market, each of which is considered suitable for certain job/user requirements. To recommend a suitable rehabilitation technique, it is necessary to consider all contributing attributes that help in performing the selection process. Based on the discussion presented in Section 2.7, a number of contributing attributes were considered. These attributes could be grouped into three main categories (see Table 4–1). These categories are technical requirements, contractual requirements and cost effectiveness. Technical requirements are defined as those attributes that determine the feasibility of the rehabilitation technique being considered and are independent of any personal preference or contractual obligations. They include type of repair, diameter of pipe, degree of bends, ability to improve hydraulic characteristics, distance between access points, ability to accommodate future differential settlement. Contractual requirements include attributes that ensure compliance of the rehabilitation technique with all terms and conditions of contract. They include duration of project, by-pass requirements, number of years in business of supplier and length of product installed, life expectancy, locality of suppliers, type of access to the original pipe (i.e. the host-pipe), method of service connections, degree of innovation. Cost effectiveness is defined as the ability of the technique to fulfill the budgetary limitations of a certain project.

TABLE 4.1

Selection Attributes

| | UNITS AND LIMITS |
|---|---|
| GROUP I: TECHNICAL REQUIREMENTS | |
| Type of repair | "Structural" or "Non-structural" |
| Diameter of pipe | 2.5 (cm)–350 (cm) |
| Degree of bends | 0°–90° |
| Ability to improve hydraulic characteristics | "Improved" or "Not improved" |
| Distance between access points | Unlimited (m) |
| Ability to accommodate future differential settlement | "Yes" or "No" |
| Group II: CONTRACTUAL REQUIREMENTS | |
| Duration of project | Unlimited (Weeks) |
| By-pass requirements | "Yes" or "No" |
| Years in business and length of product installed | Unlimited (Year) and unlimited (km), respectively |
| Life expectancy | Unlimited (year) |
| Locality of suppliers | "Yes" or "No" |
| Type of access to the original pipe | "Manhole" or "Manhole & excavation pits" |
| Method of service Connections | "Excavation pits are not required" or "Excavation pits are required" |
| Degree of innovation | 1–5, indicating poor and excellent, respectively |
| Group III: COST EFFECTIVENESS | |
| Cost of product | Unlimited ($/cm of diameter/m of length) |

The conceptual design of a database is usually represented utilizing an entity relationship (ER) diagram, as shown in FIG. 94 (Johnson 1997). It provides a comprehensive description of the database structure, highlighting its entities and attributes. As depicted in FIG. 94, the ER diagram consists of eight main entities: type of defect, products, ability to accommodate future differential settlement, method of lateral connection, by-pass requirements, diameter, type of repair and ability to improve hydraulic characteristics. The attributes associated with type of defect are I.D. and name. Attributes associated with products are I.D., distance between access points, years in business of supplier, length of product installed, design life, access type, duration, innovation, locality, cost and name of product. Attributes associated with diameter are I.D. and diameter. Attributes associated with hydraulic characteristics are I.D. and improvement. Attributes associated with settlement are I.D. and settlement. Attributes associated with type of repair are I.D. and structural requirements. Attributes associated with lateral connections are I.D. and lateral connection requirements and attributes associated with by-pass are I.D. and by-pass requirements. As could be noticed from FIG. 94, entities representing type of defect, ability to accommodate future differential settlement, method of service connection, by-pass requirements, diameter, type of repair and ability to improve hydraulic characteristics are connected by many-to-many relationships to the Products' table.

In order to implement the design suggested in the previously described ER diagram, each entity was mapped into a table. Each table was structured and its related attributes were added. Each attribute was then assigned its data-type (i.e. text or numeric) and constraints. A sample of this process is shown, for the "Products" table, in FIG. 93. Similarly, all entities and attributes were mapped into tables, with each table having its own function. The descriptions of various tables are listed in Table 4–2.

TABLE 4.2

Description of Various Tables in the Database

| TABLE'S NAME | DESCRIPTION |
| --- | --- |
| Products | Contains relevant technical, contractual and cost information about different rehabilitation techniques. |
| Type of defect | Contains information about the ability of various rehabilitation techniques to repair various types of defects. |
| Settlement | Contains information about the ability of various rehabilitation techniques to accommodate differential settlements. |
| Lateral connection | Contains information about the ability of each rehabilitation technique to reconnect laterals to the rehabilitated pipe without digging. |
| By-pass requirements | Contains information about the ability of each rehabilitation technique to be applied while the original pipe is service. |
| Diameter | Contains the range of diameters for various products. |
| Type of repair | Contains information about the applicability of various rehabilitation techniques for repairing structural/non-structural defects. |
| Hydraulics | Contains information about the effectiveness of various rehabilitation techniques to improve the hydraulic characteristics of the host-pipe. |
| Junction | Connect "Products" and "Defects" tables through their primary keys. |
| Junction 1 | Connect "Products" and "Diameter" tables through their primary keys. |
| Junction 2 | Connect "Products" and "Hydraulics" tables through their primary keys. |
| Junction 3 | Connect "Products" and "Structural requirements" tables through their primary keys. |
| Junction 4 | Connect "Products" and "By-pass requirements" tables through their primary keys. |

TABLE 4.2-continued

Description of Various Tables in the Database

| TABLE'S NAME | DESCRIPTION |
| --- | --- |
| Junction 5 | Connect "Products" and "Settlement" tables through their primary keys. |
| Junction 6 | Connect "Products" and "Service connection" tables through their primary keys. |

The schema of the developed database is shown in FIG. 95. As depicted in this Figure, the developed database includes eight main tables and seven junction tables that describe all entities, attributes and relationships described in the ER diagram. The eight main tables represent the eight entities highlighted in the ER diagram: type of defect, products, ability to accommodate future differential settlement, method of lateral connection, by-pass requirements, diameter, type of repair and ability to improve hydraulic characteristics. It should be noted that the attributes associated with each entity are also shown in FIG. 94. As could be noticed from this figure, tables representing type of defect, ability to accommodate future settlement, method of lateral connection, by-pass requirements, diameter, type of repair and ability to improve hydraulic characteristics are connected by many-to-many relationships to the Products' table. It should be noted that Access (Freeman 1997) does not directly support this type of relationship, except through the creation of what is known as junction tables (see FIG. 95). Basically, these junctions work as intermediate tables that are related to the two main tables with many-to-one relationships. The information utilized to populate the database was acquired from 13 interviews with the manufacturers and suppliers of various methods of repair. It should also be noted that the information delivered by suppliers for attributes such as cost, duration and ability to accommodate future settlement is based on average conditions and could be changed based on any particular project requirements.

To facilitate data entry and retrieval of information by users, a user-friendly form was designed (FIGS. 96 & 97). These forms were developed in Visual Basic environment. As Shown in FIG. 97, the form consists of two sections: 1) input data and 2) output results. The input data section contains all technical, contractual and cost required information to run a query designed to search for the most suitable rehabilitation technique(s). The output results section contains the name of product(s) and suppliers' coordinates (i.e. telephone number). The suppliers' coordinates could be utilized in forwarding a request for a detailed quotation and/or analysis of the project, if needed. The form is designed with scroll-down menus to facilitate data entry.

Decision Support System (DSS)

As depicted in FIG. 92, the DSS will be activated only if more than one rehabilitation technique is suggested. The DSS utilizes multi-attribute utility theory (MAUT), which proved its effectiveness in comparing alternatives in a multi-attributed decision environment (Moselhi and Deb 1993 and Moselhi and Sigurdardottir 1998). In this method, the overall utility value of alternatives is expressed as follows (Keeney and Raiffa 1976):

$$U_i = \sum_{j=1}^{n} W_j U_{ij} \qquad (4.1)$$

In which: $W_j$=The relative weight assigned to the $j^{th}$ attribute; $U_{ij}$=The value of the $j^{th}$ attribute utility function (i.e. the utility value) associated with the $i^{th}$ method of rehabilitation (i.e. the alternative being considered).

As can be noticed from Equation 4–1, there are two basic parameters necessary for calculating the overall utility values: the relative weight associated with each attribute (i.e. its priority or relative importance among all considered attributes), and the value of the utility function for each attribute. The relative weight is decided based on a pair-wise comparison of all attributes. This pair-wise comparison is performed on a scale of 1–9 (Table 4–3) and follows the process introduced by Saaty (1982).

TABLE 4.3

Pair-wise Comparison Scale (Saaty 1982)

| SCALE | DEFINITION |
|---|---|
| 1 | Equal importance of both attributes |
| 3 | Weak importance of one attribute over the other |
| 5 | Strong importance of one attribute over the other |
| 7 | Demonstrated importance of one attribute over the other |
| 9 | Absolute importance of one attribute over the other |
| 2, 4, 6, 8 | Intermediate values between two adjacent judgments |

In conducting the pair-wise comparisons, it is important to be consistent in assigning the relative importance among the attributes. In other words, if attribute "A" is 4 times more important that Attribute "B", and Attribute "B" is twice as important as attribute "C", then, if the user is consistent, attribute "A" should be 8 times more important than attribute "C". If during the assignment of relative importance, attribute "C" was assigned a relative importance more than attribute "A", or alternatively, attribute "A" was assigned a relative importance more than 8 compared to attribute "C", then inconsistent assignment of importance was performed. This inconsistency could adversely affect the quality of the decision made, and ultimately the suitability of the selected rehabilitation technique. Accordingly, the consistency of relative importance should be monitored to prevent misleading conclusions. This consistency is monitored through evaluation of the consistency ratio (CR). The method of evaluation of CR is presented in Appendix B. It should be noted that values of CR in excess of 10% suggest inconsistent values entered by the user.

The utility functions of attributes are constructed based on the desirable values for each attribute. In so doing, utility values of 1.0 and 0.0 are assigned to the most and least desirable values, respectively. Intermediate utility values are assigned to express the degree of satisfaction of the decision maker as each attribute takes values between the two extremes.

In implementing the above described decision support technique, the developed system was designed in a manner that requires the user to specify the attributes for each project being considered (FIG. 98). The decision is based on a maximum of 6 major attributes. These attributes are cost, duration, innovation, number of years in business, number of kilometers installed and life expectancy. The user can select a subset from that list of attributes for evaluating the various alternatives being considered. This design was implemented to expand the flexibility of the system and to accommodate different users' requirements. Once the user has specified the combination of attributes he would like to consider in his decision analysis, the system gets into an interactive dialogue designed to elicit the user preference. This dialogue is conducted through prompting the user to a set of questions. It should be noted that each dialogue consists of five questions. These questions are designed to elicit the user preference with respect to the most, least and intermediate values related to the attribute in question. A sample of these questions is shown in FIG. 99. It should also be noted that this dialogue is executed for each attribute selected by the user.

After the system has determined various points representing user preference for each attribute, it generates various functions representing these points. These functions are linear, logarithmic, exponential, power, polynomial with second and third degrees. (FIG. 100). It should be noted that the coefficient of multiple determination (R2) is also calculated for each function. Once the system generates all possible functions, it prompts the user to select the one best depicting his preference. This is achieved by comparing the values of R2 (FIG. 101). The selected functions are used later to determine the user's satisfaction as these attributes take values between the most and least desirable values.

Upon constructing the utility functions and calculating the various utility values of attributes, the system then establishes the relative weights for the decision criteria. In so doing, the system gives the choice to the user as to use pre-defined weights, or, alternatively, let the system calculate them automatically (FIG. 102). This flexible design was made to accommodate different user requirements and to reduce the program execution time in case of frequent uses. In case the user selects the first choice (i.e. use pre-defined set of weights), the system prompts the user to specify the file name in which the weights are saved, or, alternatively, to feed in weights of his choice (FIGS. 103 and 104). But, if the user selects the second choice (i.e. the system is to calculate the weights), then the system prompts the user to a relative importance screen, in which he has to feed in the relative importance factors (FIG. 105). It should be noted that these relative importance factors are based on a scale of 1–9. Since the relative importance factors are in a matrix form (i.e. the screen shown in FIG. 105), the user is required to fill in one triangle only (i.e. above or bellow the diagonal), and the other one is generated automatically. This was done to facilitate and ease the process of data entry. Once the relative importance factors have been decided by the user, the system calculates the weights of various attributes (FIG. 106). As can be noticed From FIG. 106, the CR is calculated for consistency monitoring. In case the CR value exceeds 10%, indicating inconsistency in assigning relative importance factors, the user is given the choice to revise his input data. Once the various weights of attributes are calculated, the system calculates the overall utility values using Equation 4-1 (FIG. 107).

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

TABLE A-1

Final Parameters Used in Designing InfiltrationNet 1

| Parameter | Value |
|---|---|
| Network paradigm | Back-propagation |
| Number of neurons in input layer | 17 |
| Number of neurons in output layer | 2 |
| Number of neurons in hidden layer | 35 |
| Number of hidden layers | 1 |
| activation function in hidden layer | Gaussian |
| Activation function in output layer | Logistic |
| Initial weight | 1.2 |
| Learning rate | 0.2 |
| Momentum | 0.2 |
| Calibration interval | 50 |
| Saving of network | At the best testing set |

TABLE A-2

Final Parameters Used in Designing InfiltrationNet 2

| Parameter | Value |
|---|---|
| Network paradigm | Back-propagation |
| activation function in hidden layer | Gaussian |
| Activation function in output layer | Logistic |
| Initial weight | 0.3 |
| Learning rate | 0.1 |
| Momentum | 0.1 |
| Number of neurons in hidden layer | 39 |
| Number of neurons in input layer | 8 |
| Number of neurons in output layer | 2 |
| Calibration interval | 50 |
| Saving of network | At the best testing set |
| Number of hidden layers | 1 |

TABLE A-3

Final Parameters Used in Designing InfiltrationNet 3

| Parameter | Value |
|---|---|
| Network paradigm | Back-propagation |
| activation function in hidden layers | Gaussian |
| Activation function in output layer | Logistic |
| Initial weight | 0.7 |
| Learning rate | 0.2 |
| Momentum | 0.2 |
| Number of neurons in hidden layer # 1 | 32 |

TABLE A-3-continued

Final Parameters Used in Designing InfiltrationNet 3

| Parameter | Value |
|---|---|
| Number of neurons in hidden layer # 2 | 47 |
| Number of neurons in input layer | 8 |
| Number of neurons in output layer | 2 |
| Calibration interval | 50 |
| Saving of network | At the best testing set |
| Number of hidden layers | 2 |

TABLE A-4

Final Parameters used in Designing DepositNet 1

| Parameter | Value |
|---|---|
| Network paradigm | Back-propagation |
| Number of neurons in input layer | 17 |
| Number of neurons in output layer | 2 |
| Number of neurons in hidden layer | 40 |
| Number of hidden layers | 1 |
| activation function in hidden layer | Gaussian |
| Activation function in output layer | Logistic |
| Initial weight | 0.3 |
| Learning rate | 0.1 |
| Momentum | 0.1 |
| Calibration interval | 50 |
| Saving of network | At the best testing set |

TABLE A-5

Final Parameters Used in Designing DepositNet 2

| Parameter | Value |
|---|---|
| Network paradigm | Back-propagation |
| Number of neurons in input layer | 10 |
| Number of neurons in output layer | 2 |
| Number of neurons in hidden layer | 28 |
| Number of hidden layers | 1 |
| activation function in hidden layer | Gaussian |
| Activation function in output layer | Logistic |
| Initial weight | 0.3 |
| Learning rate | 0.1 |
| Momentum | 0.1 |
| Calibration interval | 50 |
| Saving of network | At the best testing set |

TABLE A-6

Final Parameters Used in Designing DepositNet 3

| Parameter | Value |
|---|---|
| Network paradigm | Back-propagation |
| Number of neurons in input layer | 10 |
| Number of neurons in output layer | 2 |
| Number of neurons in hidden layer | 49 |
| Number of hidden layers | 1 |
| activation function in hidden layer | Gaussian |
| Activation function in output layer | Logistic |
| Initial weight | 0.3 |
| Learning rate | 0.1 |
| Momentum | 0.1 |
| Calibration interval | 50 |
| Saving of network | At the best testing set |

TABLE A-7

Initial Parameters Used in Designing a Preliminary Neural Network for Classification of Cross-sectional Reductions

| Parameter | Value |
|---|---|
| Network paradigm | Back-propagation |
| Number of neurons in input layer | 17 |
| Number of neurons in output layer | 2 |
| Number of neurons in hidden layer | 19 |
| Number of hidden layers | 1 |
| activation function in hidden layer | Sine |
| Activation function in output layer | Logistic |
| Initial weight | 0.2 |
| Learning rate | 0.5 |
| Momentum | 0.1 |
| Calibration interval | 50 |
| Saving of network | At the best testing set |

TABLE A-8

Final Parameters Used in Designing CrossNet 1

| Parameter | Value |
|---|---|
| Network paradigm | Back-propagation |
| Number of neurons in input layer | 13 |
| Number of neurons in output layer | 2 |
| Number of neurons in hidden layer | 39 |
| Number of hidden layers | 1 |
| activation function in hidden layer | Gaussian |
| Activation function in output layer | Logistic |
| Initial weight | 0.3 |
| Learning rate | 0.2 |
| Momentum | 0.2 |
| Calibration interval | 50 |
| Saving of network | At the best testing set |

TABLE A-9

Final Parameters Used in Designing CrossNet 2

| Parameter | Value |
|---|---|
| Network paradigm | Back-propagation |
| Number of neurons in input layer | 13 |
| Number of neurons in output layer | 2 |
| Number of neurons in hidden layer | 21 |
| Number of hidden layers | 1 |
| activation function in hidden layer | Gaussian |
| Activation function in output layer | Logistic |
| Initial weight | 0.3 |
| Learning rate | 0.1 |
| Momentum | 0.1 |
| Calibration interval | 50 |
| Saving of network | At the best testing set |

TABLE A-10

Final Parameters Used in Designing CrossNet 3

| Parameter | Value |
|---|---|
| Network paradigm | Back-propagation |
| Number of neurons in input layer | 13 |
| Number of neurons in output layer | 2 |
| Number of neurons in hidden layer | 22 |
| Number of hidden layers | 1 |
| activation function in hidden layer | Gaussian |
| Activation function in output layer | Logistic |
| Initial weight | 1.2 |
| Learning rate | 0.2 |
| Momentum | 0.2 |
| Calibration interval | 50 |
| Saving of network | At the best testing set |

TABLE A-11

Initial Parameters Used in Designing a Preliminary Neural Network for Classification of Misalignments

| Parameter | Value |
|---|---|
| Network paradigm | Back-propagation |
| Number of neurons in input layer | 17 |
| Number of neurons in output layer | 2 |
| Number of neurons in hidden layer | 19 |
| Number of hidden layers | 1 |
| Activation function in hidden layer | Sine |
| Activation function in output layer | Logistic |
| Initial weight | 0.2 |
| Learning rate | 0.5 |
| Momentum | 0.1 |
| Calibration interval | 50 |
| Saving of network | At the best testing set |

TABLE A-12

Final Parameters Used in Designing AlignmentNet 1

| Parameter | Value |
|---|---|
| Network paradigm | Back-propagation |
| Number of neurons in input layer | 11 |
| Number of neurons in output layer | 2 |
| Number of neurons in hidden layer | 32 |
| Number of hidden layers | 1 |
| activation function in hidden layer | Gaussian |
| Activation function in output layer | Logistic |
| Initial weight | 1.2 |
| Learning rate | 0.2 |
| Momentum | 0.2 |
| Calibration interval | 50 |
| Saving of network | At the best testing set |

TABLE A-13

Final Parameters Used in Designing AlignmentNet 2

| Parameter | Value |
|---|---|
| Network paradigm | Back-propagation |
| Number of neurons in input layer | 11 |
| Number of neurons in output layer | 2 |
| Number of neurons in hidden layer | 35 |
| Number of hidden layers | 1 |
| activation function in hidden layer | Gaussian |
| Activation function in output layer | Logistic |
| Initial weight | 1.2 |
| Learning rate | 0.2 |
| Momentum | 0.2 |
| Calibration interval | 50 |
| Saving of network | At the best testing set |

TABLE A-14

Final Parameters Used in Designing AlignmentNet 3

| Parameter | Value |
| --- | --- |
| Network paradigm | Back-propagation |
| Number of neurons in input layer | 11 |
| Number of neurons in output layer | 2 |
| Number of neurons in hidden layer | 37 |
| Number of hidden layers | 1 |
| activation function in hidden layer | Gaussian |
| Activation function in output layer | Logistic |
| Initial weight | 1.2 |
| Learning rate | 0.2 |
| Momentum | 0.2 |
| Calibration interval | 50 |
| Saving of network | At the best testing set |

TABLE A-15

Final Parameters Used in Designing ModCrossNet 1

| Parameter | Value |
| --- | --- |
| Network paradigm | Back-propagation |
| Number of neurons in input layer | 5 |
| Number of neurons in output layer | 2 |
| Number of neurons in hidden layer | 32 |
| Number of hidden layers | 1 |
| activation function in hidden layer | Gaussian |
| Activation function in output layer | Logistic |
| Initial weight | 0.7 |
| Learning rate | 0.1 |
| Momentum | 0.3 |
| Calibration interval | 50 |
| Saving of network | At the best testing set |

TABLE A-16

Performance Results of ModCrossNet 1

| Performance Criteria | X-sectional Red. | Non X-sect. Red. |
| --- | --- | --- |
| $R^2$ | 0.8429 | 0.8420 |
| Mean squared error | 0.036 | 0.036 |
| Mean absolute error | 0.111 | 0.109 |
| Min. absolute error | 0 | 0 |
| Max. absolute error | 0.608 | 0.615 |
| Correlation coefficient (r) | 0.9239 | 0.9229 |
| Recognition rate | 85.7% | 100% |

TABLE A-17

Final Parameters Used in Designing of ModCrossNet 2

| Parameter | Value |
| --- | --- |
| Network paradigm | Back-propagation |
| Number of neurons in input layer | 5 |
| Number of neurons in output layer | 2 |
| Number of neurons in hidden layer | 39 |
| Number of hidden layers | 1 |
| activation function in hidden layer | Gussian |
| Activation function in output layer | Logistic |
| Initial weight | 0.6 |
| Learning rate | 0.2 |
| Momentum | 0.4 |
| Calibration interval | 50 |
| Saving of network | At the best testing set |

TABLE A-18

Performance Results of ModCrossNet 2

| Performance Criteria | X-sectional Red. | Non X-sect. Red. |
| --- | --- | --- |
| $R^2$ | 0.9061 | 0.9071 |
| Mean squared error | 0.021 | 0.021 |
| Mean absolute error | 0.083 | 0.083 |
| Min. absolute error | 0 | 0 |
| Max. absolute error | 0.279 | 0.268 |
| Correlation coefficient (r) | 0.9573 | 0.9581 |
| Recognition rate | 100% | 100% |

TABLE A-19

Final Parameters Used in Designing ModCrossNet 3

| Parameter | Value |
| --- | --- |
| Network paradigm | Back-propagation |
| Number of neurons in input layer | 5 |
| Number of neurons in output layer | 2 |
| Number of neurons in hidden layer | 36 |
| Number of hidden layers | 1 |
| activation function in hidden layer | Gussian |
| Activation function in output layer | Logistic |
| Initial weight | 0.7 |
| Learning rate | 0.2 |
| Momentum | 0.3 |
| Calibration interval | 50 |
| Saving of network | At the best testing set |

TABLE A-20

Performance Results of ModCrossNet 3

| Performance Criteria | X-sectional Red. | Non X-sect. Red. |
| --- | --- | --- |
| $R^2$ | 0.9880 | 0.9859 |
| Mean squared error | 0.003 | 0.003 |
| Mean absolute error | 0.028 | 0.031 |
| Min. absolute error | 0 | 0 |
| Max. absolute error | 0.112 | 0.126 |
| Correlation coefficient (r) | 0.9965 | 0.9958 |
| Recognition rate | 100% | 100% |

Appendix B: Calculation of Consistency Ratio (CR)

$CR = CI/\text{random consistency}$

Where $CI = \lambda_{max} - N/(N-1)$ $\lambda_{max}$: Eigenvalue value of the matrix containing weights associated with all attributes N: number of considered attributes Random consistency: a random number that is a function of number of attributes, and accordingly the size of matrix (see Table 43)(Saaty 1982).

TABLE 43

Random Consistency Values

| Size of Matrix | Random Value |
| --- | --- |
| 1 | 0 |
| 2 | 0 |
| 3 | 0.58 |
| 4 | 0.9 |
| 5 | 1.12 |

TABLE 43-continued

Random Consistency Values

| Size of Matrix | Random Value |
| --- | --- |
| 6 | 1.24 |
| 7 | 1.32 |
| 8 | 1.41 |
| 9 | 1.45 |
| 10 | 1.49 |

What is claimed is:

1. A method for detecting a plurality of defects in an item under inspection comprising:
acquiring at least one image of said item;
providing a plurality of neural networks, at least one of said plurality of neural networks corresponding to each one of said plurality of defects to be detected, wherein each one of said plurality of defects is selected from at least one of cross-sectional reductions, misalignments, infiltration, and cracks;
processing said at least one image to produce a processed image having objects isolated from an image background of said image; and
inputting said processed image into said plurality of neural networks to obtain information concerning corresponding defects.

2. A method as claimed in claim 1, further comprising issuing a report using said information concerning said defects.

3. A method as claimed in claim 2, further comprising recommending a rehabilitation technique based on said report and a set of attributes of said item under inspection.

4. A method as claimed in claim 3, wherein said attributes are part of a group comprising technical requirements, contractual requirements, and cost effectiveness.

5. A method as claimed in claim 3, wherein a plurality of rehabilitation techniques are recommended.

6. A method as claimed in claim 5, further comprising ranking said plurality of recommended rehabilitation techniques.

7. A method as claimed in claim 1, wherein said plurality of neural networks further comprises sets of neural networks used for counter-checking results, each one of said sets of similar neural networks corresponding to each one of said plurality of defects to be detected.

8. A method as claimed in claim 1, wherein each set of neural networks comprises at least three neural networks used for counter-checking results.

9. A method as claimed in claim 1, wherein processing said at least one image further comprises processing said at least one image according to a selected set of image analysis techniques, said set of image analysis techniques selected as a function of said defects to be detected.

10. A method as claimed in claim 9, wherein n sets of neural networks are used to detect n types of defects.

11. A method as claimed in claim 10, wherein:
said item under inspection is a sewer pipe;
n corresponds to 5; and
said plurality of defects are deposits, cross-sectional reductions, misalignments, infiltration, and cracks.

12. A method as claimed in claim 11, wherein deposits, cross-sectional reductions, and milsalignments correspond to a first set of image analysis techniques, infiltration corresponds to a second set of image analysis techniques, and cracks correspond to a third set of image analysis techniques.

13. A method as claimed in claim 12, wherein said first set of image analysis techniques comprises the operations of inversion, dilation, background subtraction, thresholding, segmentation, and analysis.

14. A method as claimed in claim 12, wherein said second set of image analysis techniques comprises the operations of dilation, background subtraction, thresholding, segmentation, and analysis.

15. A method as claimed in claim 12, wherein said third set of image analysis techniques comprises the operations of background subtraction, edge detection, dilation, thresholding, and analysis.

16. A method as claimed in claim 15, wherein said videotape is digitized.

17. A method as claimed in claim 1, wherein said neural networks are back-propagation neural networks.

18. A method as claimed in claim 1, wherein said acquiring an image comprises using a closed circuit television camera and a videotape.

19. A method as claimed in claim 1, further comprising determining a position of said objects in said item under inspection.

20. A method for detecting a selected defect in an item under inspection comprising:
acquiring an image of said item;
providing a neural network for detecting said selected defect, wherein said selected defect is selected from at least one of deposits, cross-sectional reductions, misalignments, infiltration, and cracks;
selecting a set of image analysis techniques as a function of said selected defect;
processing said image according to said selected set of image analysis techniques for said selected defect to produce a processed image having objects isolated from an image background of said image;
inputting said processed image to said neural network to obtain information corresponding to said selected defect.

21. A method as claimed in claim 20, further comprising issuing a report based on outputs produced by said neural network.

22. A method as claimed in claim 21, further comprising recommending a rehabilitation technique based on said report and a set of attributes of said item under inspection.

23. A method as claimed in claim 22, wherein said attributes are part of a group comprising technical requirements, contractual requirements, and cost effectiveness.

24. A method as claimed in claim 22, wherein a plurality of rehabilitation techniques are recommended.

25. A method as claimed in claim 24, further comprising ranking said plurality of recommended rehabilitation techniques.

26. A method as claimed in claim 20, wherein said providing a neural network further comprises providing a set of neural networks, said set of neural networks being used for counter-checking results.

27. A method as claimed in claim 26, wherein said set of neural networks comprises three neural networks.

28. A method as claimed in claim 20, wherein deposits, cross-sectional reductions, and misalignments correspond to a first set of image analysis techniques, infiltration corresponds to a second set of image analysis techniques, and cracks correspond to a third set of image analysis techniques.

29. A method as claimed in claim 28, wherein said first set of image analysis techniques comprises the operations of inversion, dilation, background subtraction, thresholding, segmentation, and analysis.

30. A method as claimed in claim 28, wherein said second set of image analysis techniques comprises the operations of dilation, background subtraction, thresholding, segmentation, and analysis.

31. A method as claimed in claim 28, wherein said third set of image analysis techniques comprises the operations of background subtraction, edge detection, dilation, thresholding, and analysis.

32. A method as claimed in claim 20, wherein said neural network is a back-propagation neural network.

33. A method as claimed in claim 20, wherein said acquiring an image comprises using a closed circuit television camera and a videotape.

34. A method as claimed in claim 33, wherein said videotape is digitized.

35. A method as claimed in claim 20, further comprising determining a position of said objects in said item under inspection.

* * * * *